(12) United States Patent
Shema-Yaacoby et al.

(10) Patent No.: US 11,479,805 B2
(45) Date of Patent: Oct. 25, 2022

(54) COMBINATORIAL SINGLE MOLECULE ANALYSIS OF CHROMATIN

(71) Applicants: The General Hospital Corporation, Boston, MA (US); SEQLL LLC, Woburn, MA (US)

(72) Inventors: Efrat Shema-Yaacoby, Brookline, MA (US); Bradley Bernstein, Cambridge, MA (US); Daniel Jones, Boston, MA (US)

(73) Assignees: The General Hospital Corporation, Boston, MA (US); SEQLL LLC, Woburn, MA (US)

( * ) Notice: Subject to any disclaimer, the term of this patent is extended or adjusted under 35 U.S.C. 154(b) by 779 days.

(21) Appl. No.: 15/754,222

(22) PCT Filed: Aug. 19, 2016

(86) PCT No.: PCT/US2016/047747
§ 371 (c)(1),
(2) Date: Feb. 21, 2018

(87) PCT Pub. No.: WO2017/034970
PCT Pub. Date: Mar. 2, 2017

(65) Prior Publication Data
US 2019/0284603 A1 Sep. 19, 2019

Related U.S. Application Data

(60) Provisional application No. 62/296,422, filed on Feb. 17, 2016, provisional application No. 62/208,287, filed on Aug. 21, 2015.

(51) Int. Cl.
*C12Q 1/6806* (2018.01)
*G01N 33/68* (2006.01)
*C12Q 1/68* (2018.01)

(52) U.S. Cl.
CPC .......... *C12Q 1/6806* (2013.01); *C12Q 1/68* (2013.01); *G01N 33/6878* (2013.01)

(58) Field of Classification Search
CPC ..... C12Q 1/6806; C12Q 1/68; G01N 33/6878
See application file for complete search history.

(56) References Cited

U.S. PATENT DOCUMENTS

| | | | |
|---|---|---|---|
| 2011/0136676 A1* | 6/2011 | Greene | B01L 3/502761 506/4 |
| 2012/0244532 A1* | 9/2012 | Craighead | B01L 3/502761 435/6.11 |
| 2013/0203605 A1* | 8/2013 | Shendure | C12N 15/1093 506/2 |
| 2015/0057163 A1* | 2/2015 | Rotem | C12Q 1/6869 506/2 |

FOREIGN PATENT DOCUMENTS

| | | | |
|---|---|---|---|
| WO | 2013078470 | 5/2013 | |
| WO | 2013184930 | 12/2013 | |
| WO | 2014108810 | 7/2014 | |
| WO | WO-2014108810 A2 * | 7/2014 | ....... C12Q 2521/543 |
| WO | WO-2014190214 A1 * | 11/2014 | ........... C12Q 1/6804 |
| WO | 2014205296 | 12/2014 | |
| WO | 2016061517 | 4/2016 | |

OTHER PUBLICATIONS

Szekvolgyi et al. ("Chip-on-beads: Flow-cytometric evaluation of chromatin immunoprecipitation." Cytometry Part A: The Journal of the International Society for Analytical Cytology 69.10 (2006): 1086-1091) (Year: 2006).*
Nishida et al.( "Genome-wide maps of mononucleosomes and dinucleosomes containing hyperacetylated histones of Aspergillus fumigatus." PloS one 5.3 (2010): e9916; 8 pages). (Year: 2010).*
Chapman-Rothe et al.( "Chromatin H3K27me3/H3K4me3 histone marks define gene sets in high-grade serous ovarian cancer that distinguish malignant, tumour-sustaining and chemo-resistant ovarian tumour cells." Oncogene 32.38 (2013): 4586-4592). (Year: 2013).*
Zierhut, Christian, et al. "Nucleosomal regulation of chromatin composition and nuclear assembly revealed by histone depletion." Nature structural & molecular biology 21.7 (2014): 617. (Year: 2014).*
Luo et al. ("Nucleosomes accelerate transcription factor dissociation." Nucleic acids research 42.5 (2014): 3017-3027; published Dec. 2013). (Year: 2013).*
Luo 2013 supplementary materials (Year: 2013).*
International Search Report dated Dec. 19, 2016, which issued during prosecution of International Application No. PCT/US2016/047747.

(Continued)

*Primary Examiner* — Sahana S Kaup
(74) *Attorney, Agent, or Firm* — Melissa Hunter-Ensor; Nicholas R. Ballor; Greenberg Traurig, LLP

(57) ABSTRACT

The present invention provides for single-molecule profiling of combinatorial protein modifications and single-molecule profiling of combinatorial protein modifications combined with single-molecule sequencing of protein/nucleic acids complexes. High-throughput single-molecule imaging was applied to decode combinatorial modifications on millions of individual nucleosomes from pluripotent stem cells and lineage-committed cells. Applicants identified bivalent nucleosomes with concomitant repressive and activating marks, as well as other combinatorial modification states whose prevalence varies with developmental potency. Applying genetic and chemical perturbations of chromatin enzymes show a preferential affect on nucleosomes harboring specific modification states. The present invention also combines this proteomic platform with single-molecule DNA sequencing technology to simultaneously determine the modification states and genomic positions of individual nucleosomes. This novel single-molecule technology can be used to address fundamental questions in chromatin biology and epigenetic regulation leading to novel therapeutics and diagnostics.

24 Claims, 18 Drawing Sheets
Specification includes a Sequence Listing.

(56) References Cited

OTHER PUBLICATIONS

Shema, et al. "Single-molecule decoding of combinatorially modified nucleosomes", Science, 2016, 352 (6286):717-721 including Supplementary Materials.
Gomez, et al. "Detection of histone modifications at specific gene loci in single cells in histological sections (+Online methods)", Nature Methods, 2013, 10(2):171-177.
Gomez, et al. "Detection of histone modifications at specific gene loci in single cells in histological sections—Supplementary Figures and Table 1", Nature Methods, 2013, doi:10.1038/nmeth.2332.
Buenrostro Jason, et al. "Transposition of native chromatin for fast and sensitive epigenomic profiling of open chromatin, DNA-binding proteins and nucleosome position (+ online methods)", Nature Methods, 2013, 10 (12):1213-1218, including Supplemental Material.
Nguyen, et al. "Accelerated chromatic biochemistry using DNA-barcoded nucleosome libraries (+ online methods)", Nature Methods, 2014, 834-840.
Toshitsugu, et al. "Efficient isolation of specific genomic regions and identification of associated proteins by engineered DNA-biding molecule-mediated chromatin immunoprecipitation (enCHIP) using CRISPR", Biochemical and Biophysical Research Communications, 2013, 439:132-136.
Tomschik, et al. "Fast, long-range, reversible conformational fluctuations in nucleosomes revealed by single-pair fluorescence resonance energy transfer" Proceeding of the National Academy of Sciences, 2005, 102(9):3278-3283.
Adli et al., "Genornewide Chromatin Maps Derived from Limited Numbers of Hematopoietic Progenitors," Nature Methods, Aug. 2010, vol. 7, No. 8, pp. 615-618.
Bannister et al., "Regulation of chromatin by histone modifications," Cell Research, 2011, vol. 21, pp. 381-395.
Bernstein et al., "A Bivalent Chromatin Structure Marks Key Developmental Genes in Embryonic Stem Cells," Cell, Apr. 21, 2006, vol. 125, pp. 315-326.
Campos et al., "Histones: Annotating Chromatin," Annual Review of Genetics, 2009, vol. 43, pp. 559-599.
Chabbert et al., "A high-throughput ChIP-Seq for large-scale chromatin studies," Molecular Systems Biology, 2015, vol. 11, Article No. 777, pp. 1-14.
Collas, Philippe, "The Current State of Chromatin Immunoprecipitation," Molecular Biotechnology, Jan. 14, 2010, vol. 45, pp. 87-100.
Ernst et al., "Systematic analysis of chromatin state dynamics in nine human cell types," Nature, May 5, 2011, vol. 473, No. 7345, pp. 43-49.
Ferrari et al., "Polycomb-Dependent H3K27me1 and H3K27me2 Regulate Active Transcription and Enhancer Fidelity," Molecular Cell, Jan. 9, 2014, vol. 53, pp. 49-62.
Gilmour et al., "Detecting protein-DNA interactions in vivo: Distribution of RNA polymerase on specific bacterial genes," Proceedings of the National Academy of Sciences of the United States of America, Jul. 1984, vol. 81, pp. 4275-4279.
Goren et al., "Chromatin Profiling by Directly Sequencing Small Quantities of Immunoprecipitated DNA," Nature Methods, Jan. 2010, vol. 7, No. 1, pp. 47-49.
Jenuwein et al., "Translating the Histone Code," Science, Aug. 10, 2001, vol. 293, pp. 1074-1080.
Johnson et al., "Chromatin: Receiver and Quarterback for Cellular Signals," Cell, Feb. 14, 2013, vol. 152, pp. 685-689.
Jung et al., "Quantitative Mass Spectrometry of Histones H3.2 and H3.3 in Suz12-deficient Mouse Embryonic Stem Cells Reveals Distinct, Dynamic Post-translational Modifications at Lys-27 and Lys-36," Molecular & Cellular Proteomics, 2010, vol. 9, pp. 838-850.
Kouzarides, Tony, "Chromatin Modifications and Their Function," Cell, Feb. 23, 2007, vol. 128, pp. 693-705.
Kuo et al., "In Vivo Cross-Linking and Immunoprecipitation for Studying Dynamic Protein:DNA Associations in a Chromatin Environment," Methods, Nov. 1999, vol. 19, No. 3, pp. 425-433.
Lara-Astiaso et al., "Chromatin state dynamics during blood formation," Science, Aug. 22, 2014, vol. 345, No. 6199, pp. 943-949.
Lee et al., "The Language of Histone Crosstalk," Cell, Sep. 3, 2010, vol. 142, pp. 682-685.
Mikkelsen et al., "Genome-wide maps of chromatin state in pluripotent and lineage-committed cells," Nature, Aug. 2, 2007, vol. 448, No. 7153, pp. 553-560.
O'Neill et al., "Epigenetic characterization of the early embryo with a chromatin immunoprecipitation protocol applicable to small cell populations," Nature Genetics, Jul. 2006, vol. 38, No. 7, pp. 835-841.
Rivera et al., "Mapping Human Epigenomes," Cell, Sep. 26, 2013, vol. 155, pp. 39-55.
Rotem et al., "Single-cell ChIP-seq reveals cell subpopulations defined by chromatin state." Nature Biotechnology, Nov. 2015, vol. 33, No. 11, pp. 1165-1172.
Sarma et al., "Historic Variants Meet Their Match," Nature Reviews Molecular Cell Biology, Feb. 2005, vol. 6, pp. 139-149.
Schones et al., "Genome-wide approaches to studying chromatin modifications," Nature Reviews Genetics, Mar. 2008, vol. 9, pp. 179-191.
Schreiber et al., "Signaling Network Model of Chromatin," Cell, Dec. 13, 2002, vol. 111, pp. 771-778.
Sidoli et al., "Properly reading the historic code by MS-based proteomics," Proteomics, 2015; vol. 15, pp. 2901-2902.
Solomon et al., "Mapping Protein-DNA Interactions In Vivo with Formaldehyde: Evidence That Histone H4 Is Retained on a Highly Transcribed Gene," Cell, Jun. 17, 1988, vol. 53, Iss. 6, pp. 937-947.
Thurman et al., "The accessible chromatin landscape of the human genome," Nature, Sep. 6, 2012, vol. 489, pp. 75-82.
Van Galen et al., "A Multiplexed System for Quantitative Comparisons of Chromatin Landscapes," Molecular Cell, Jan. 7, 2016, vol. 61, pp. 170-180.
Zheng et al., "Low-Cell-Number Epigenome Profiling Aids the Study of Lens Aging and Hematopoiesis," Cell Reports, Nov. 17, 2015, vol. 13, pp. 1505-1518.
Zhou et al., "Charting histone modifications and the functional organization of mammalian genomes," Nature Reviews Genetics, Jan. 2011, vol. 12, pp. 7-18.

* cited by examiner

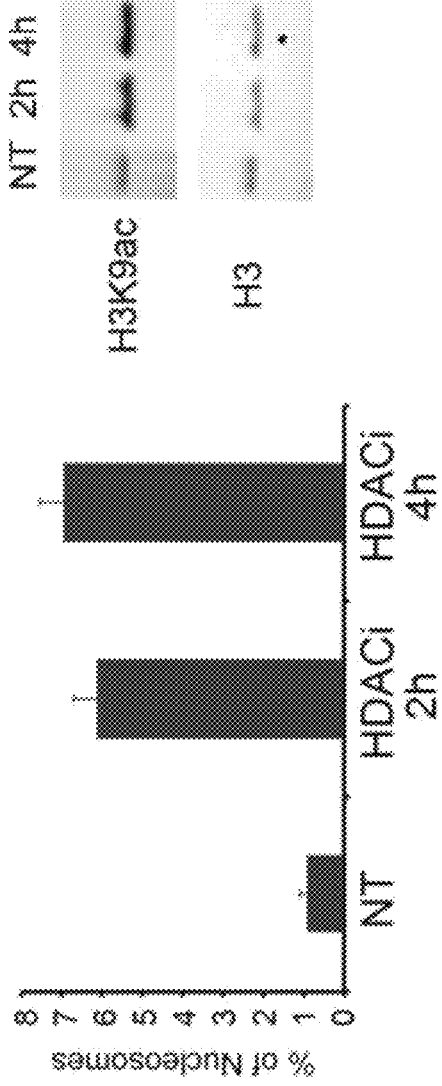
FIG. 1B
FIG. 1C
FIG. 1D
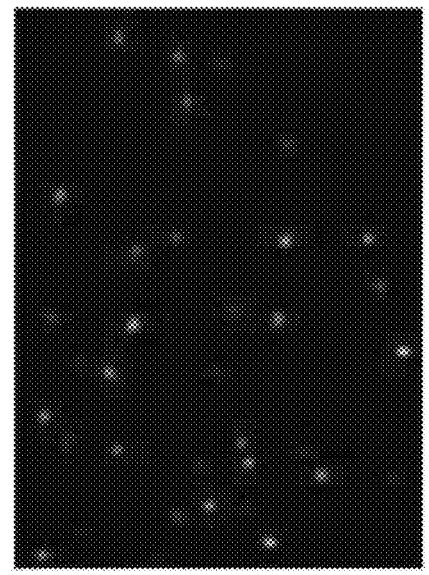
FIG. 1E
FIG. 1F

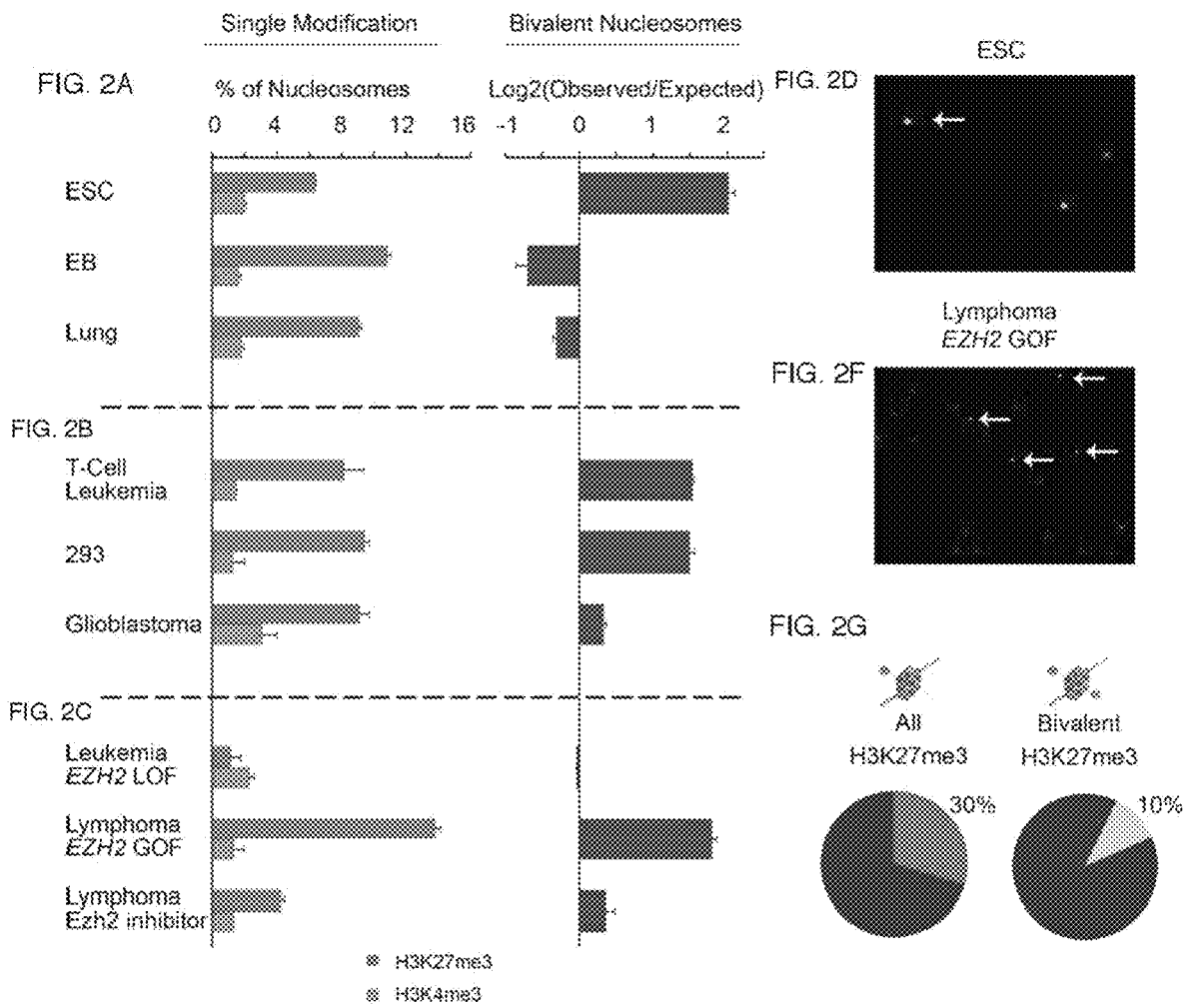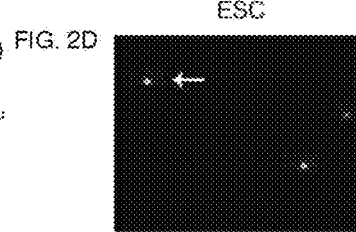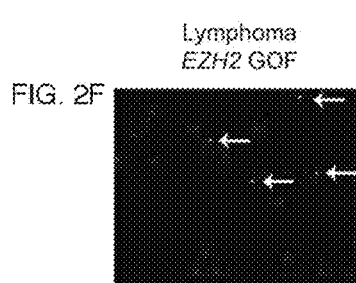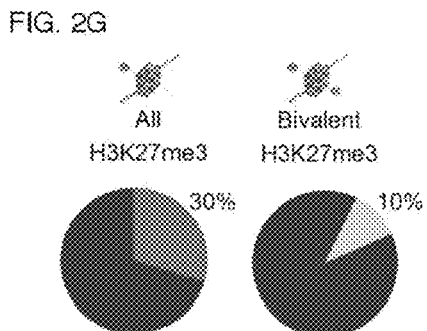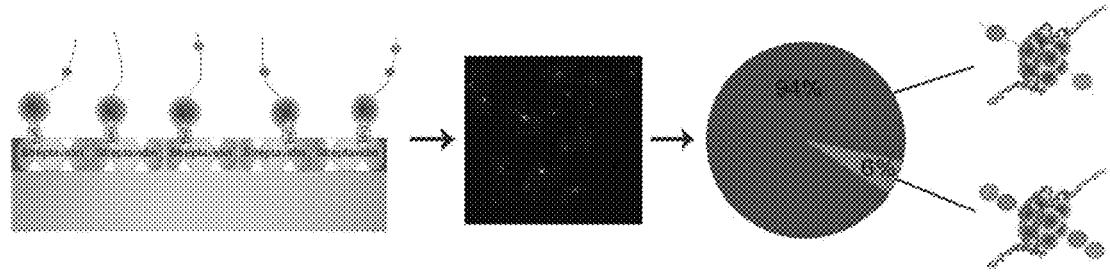

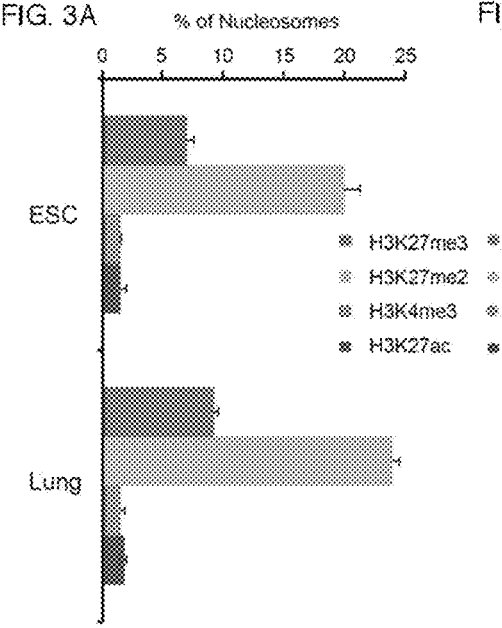
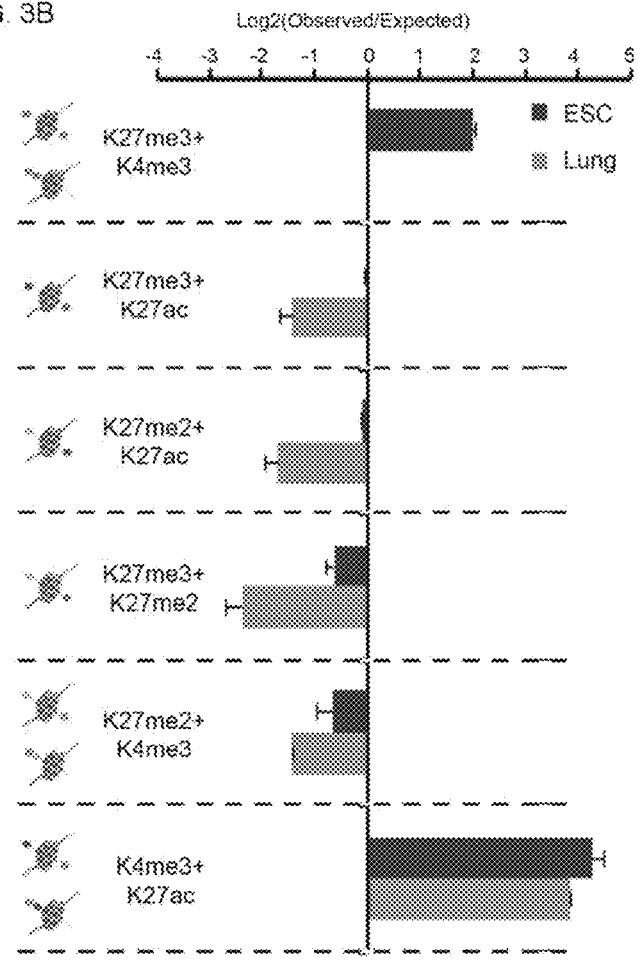
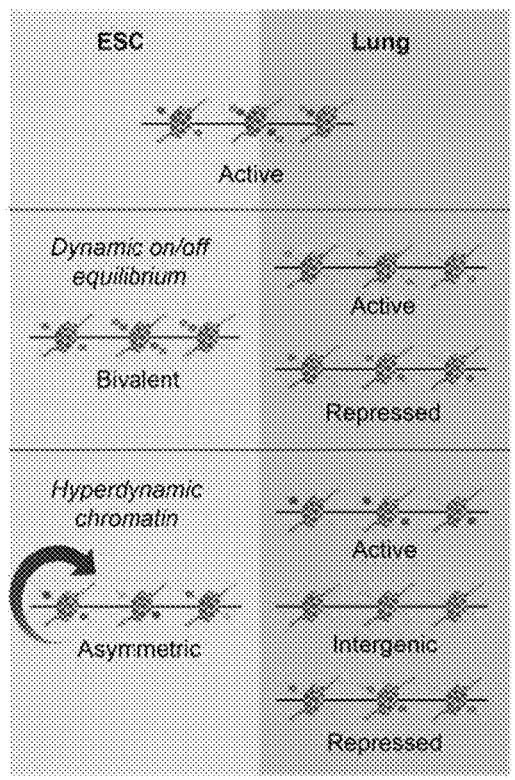
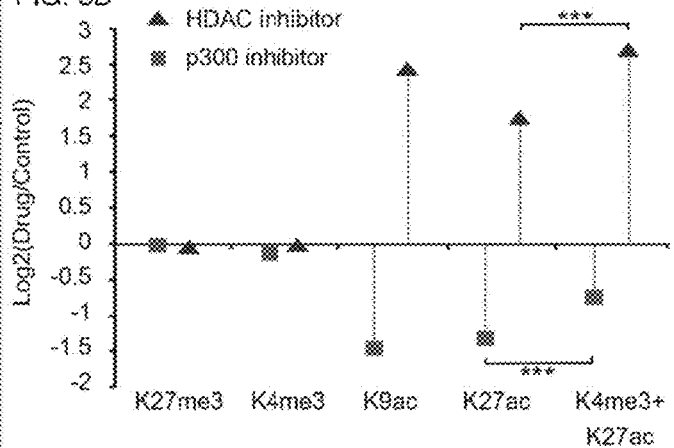

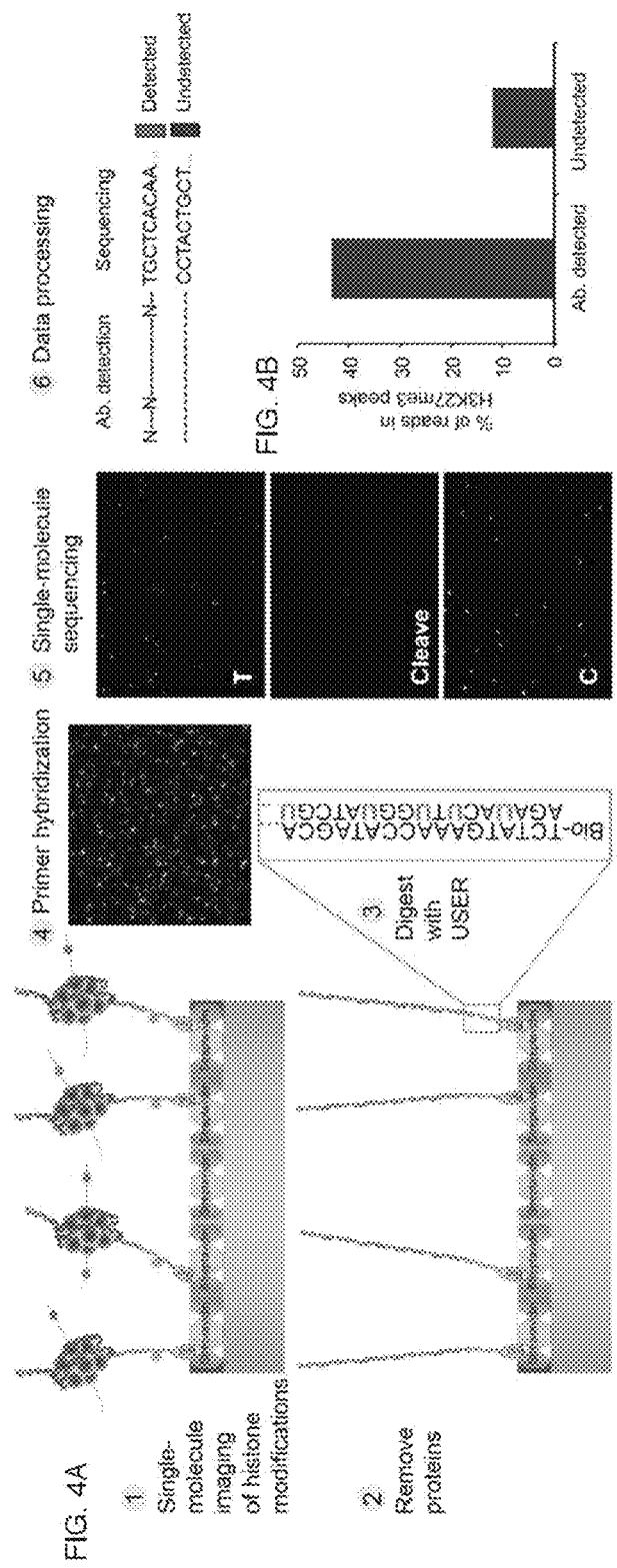

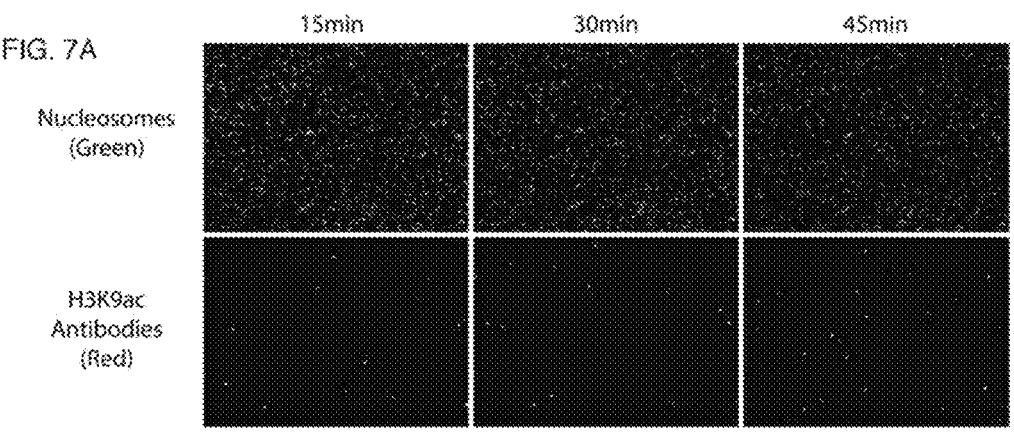
FIG. 7A
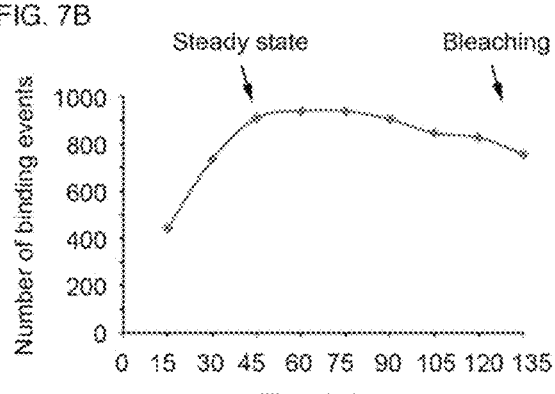
FIG. 7B
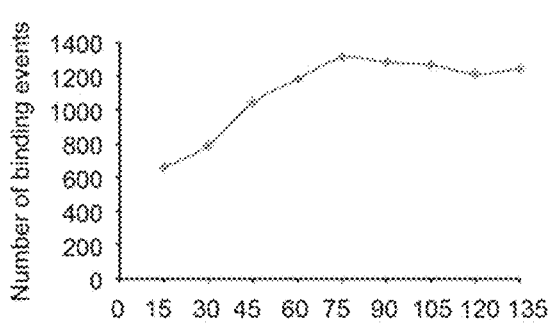
FIG. 7C
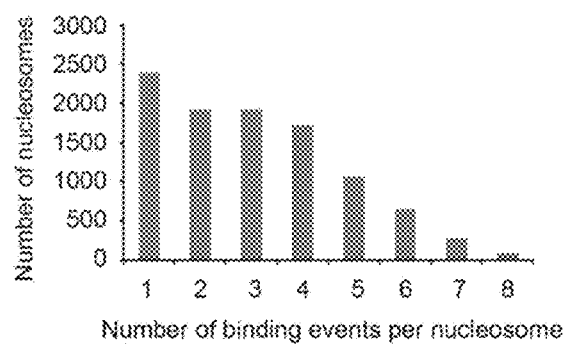
FIG. 7D
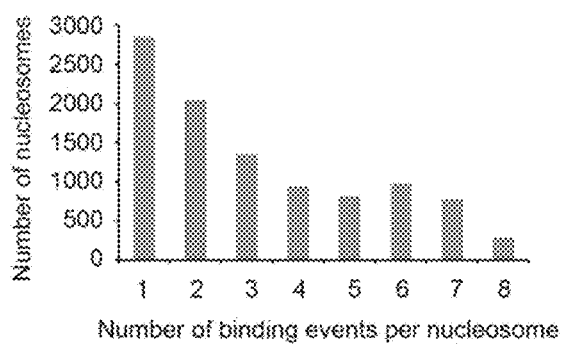
FIG. 7E
FIG. 7F
| Time  | 30 | 45 | 60 | 75 | 90 | 105 | 120 | 135 |
|-------|----|----|----|----|----|-----|-----|-----|
| Nuc 1 |    | ●  | ●  |    |    |     |     |     |
| Nuc 2 | ●  |    |    |    |    |     | ●   | ●   |
| Nuc 3 |    |    |    | ●  |    |     |     |     |
| Nuc 4 | ●  |    |    | ●  | ●  |     | ●   |     |
| Nuc 5 |    |    | ●  |    |    | ●   |     |     |

FIG. 14A
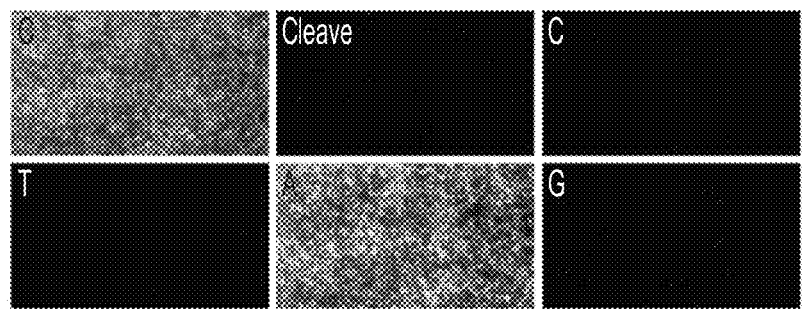
FIG. 14B
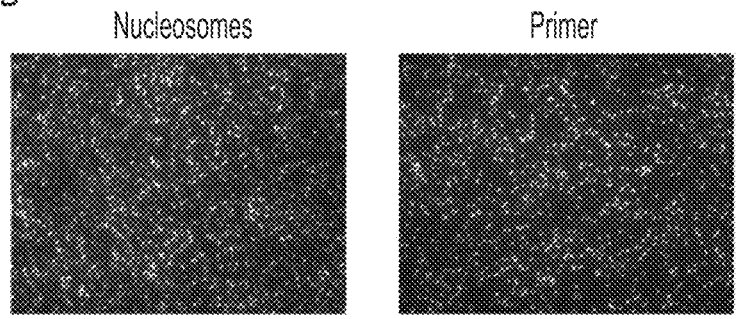
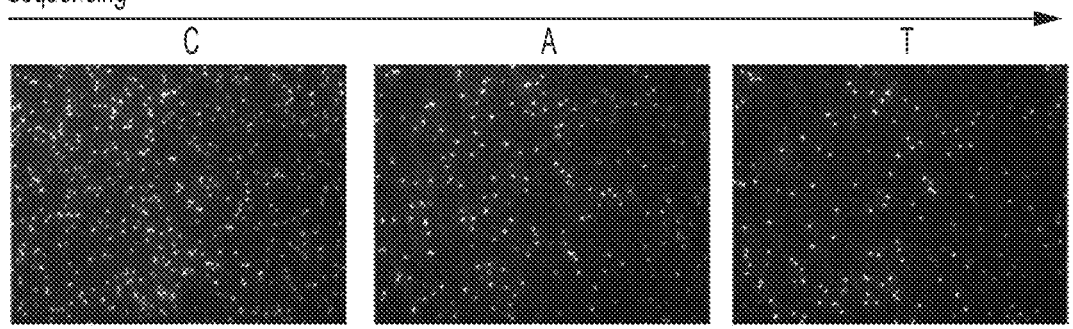

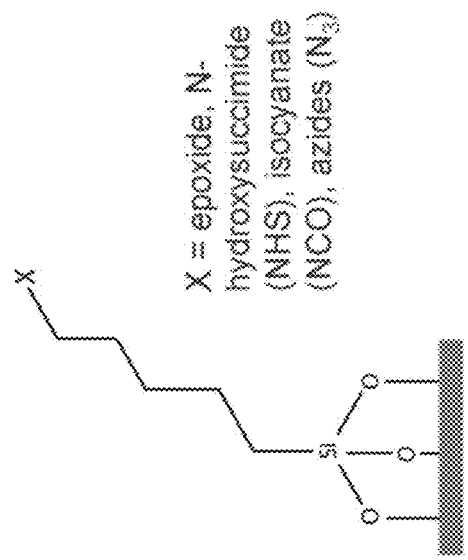
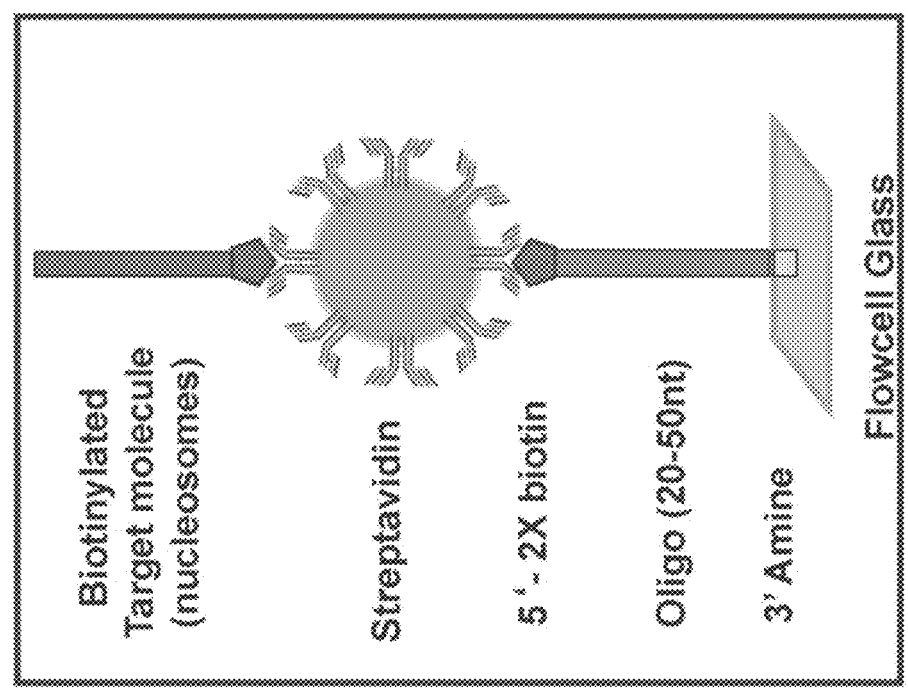
FIG. 16

SEQUENCE LISTING

<160> NUMBER OF SEQ ID NOS: 12

<210> SEQ ID NO 1
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
agatcggaag a                                                          11

<210> SEQ ID NO 2
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
agatcggaag a                                                          11

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ttaacacgac gctcttccga tct                                             23

<210> SEQ ID NO 4
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ttaaccgatc acttctacga taccaaagta tct                                  33

<210> SEQ ID NO 5

```
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
agauacutug guaucguaga agugaucggt taa                               33

<210> SEQ ID NO 6
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
agatactttg gtatcgtaga agtgatcggt ta                                32

<210> SEQ ID NO 7
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
cttgaggccg gtaatacgac tcactatagg ggttcagagt tctacagtgg aaaaaaaaaa  60
aaaaaaaaaa aaaaaaaaaa aaaaaaaaaa                                   90

<210> SEQ ID NO 8
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Leu Ala Thr Lys Ala Ala Arg Lys Ser Ala Pro Ala Thr Gly Gly
1               5                   10                  15

Val Lys Lys

<210> SEQ ID NO 9
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
tctatgaaac catagca                                                 17

<210> SEQ ID NO 10
```

```
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
ugctauggut ucauaga                                              17

<210> SEQ ID NO 11
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gcgtcgtgtt aa                                                   12

<210> SEQ ID NO 12
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gcgtcgtgtt aa                                                   12
```

COMBINATORIAL SINGLE MOLECULE ANALYSIS OF CHROMATIN

RELATED APPLICATIONS AND INCORPORATION BY REFERENCE

This application is a U.S. National Stage Application under 35 U.S.C. § 371 of International Patent Application No. PCT/US16/47747, which was filed on Aug. 19, 2016. This application claims priority to and benefit of U.S. provisional application Ser. Nos. 62/208,287, filed Aug. 21, 2015 and 62/296,422, filed Feb. 17, 2016.

The foregoing applications, and all documents cited therein or during their prosecution ("appln cited documents") and all documents cited or referenced in the appln cited documents, and all documents cited or referenced herein ("herein cited documents"), and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. HG006991 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 17, 2016, is named 46783.99.2135_SL.txt and is 3,803 bytes in size.

FIELD OF THE INVENTION

The present invention relates to methods for single-molecule profiling of combinatorial protein modifications and single-molecule profiling of combinatorial protein modifications combined with single-molecule sequencing of protein/nucleic acid complexes.

BACKGROUND OF THE INVENTION

Genes and genomic elements are packaged by chromatin structures that regulate their accessibility and activity in a cell type-specific manner (45,46). The fundamental building block of chromatin is the nucleosome, composed of ~146 bp of DNA wrapped around an octamer of histone proteins. A nucleosome can include combinations of core histones and histone variants (Sarma, K. and Reinberg, D., 2005. Histone variants meet their match. Nature Reviews Molecular Cell Biology 6, 139-149). Histones are heavily modified by covalent attachment of various chemical groups at specific amino acid positions (1-3). These modifications are an integral component of the epigenetic control of genome function, enabling the manifestation of unique cellular phenotypes in multicellular organisms, which harbor identical genomic sequences. The identification of >100 modifications has led to the hypothesis that combinatorial marks specify distinct regulatory outcomes (the 'histone code') (4), but this hypothesis has been difficult to test due to technical issues. However, understanding of the histone code and other models (5) has been constrained by the limited ability to detect, quantify and map combinatorially-modified nucleosomes. Chromatin immunoprecipitation (ChIP), a predominant method in chromatin biology, can identify the genomic location of a specific modification, but cannot effectively distinguish whether coincident marks co-exist on the same nucleosome, or originate from different alleles or cells. Mass spectrometry can only compare marks if they are adjacent on the same histone peptide and does not address genomic location (6-8). Although alternative approaches (9), such as flowing nucleosomes through nanochannels (10), show promise, they have limited throughput and/or do not provide genomic information.

Chromatin modifications can be mapped genome-wide by coupling chromatin immunoprecipitation and sequencing (ChIP-seq). The resulting 'chromatin state' maps based on genome-wide patterns of multiple modifications are a powerful means for identifying functional genomic elements, such as promoters, enhancers, insulators, and repressed loci (34, 46-49). The approach is complementary to techniques that measure DNA accessibility (50,51), but provides more specific information regarding the likely functions of detected elements. Chromatin state maps have uncovered a wide range of gene regulatory mechanisms that underlie normal development or disease processes. Essentially all existing methods for mapping chromatin modifications or transcription factors (transcription factors) rely on ChIP, in which antibodies are used to enrich chromatin harboring particular epitopes. The approach has been improved over the years (52,53), but remains rooted in methods described nearly 30 years ago (54,55).

ChIP has major limitations. First, the IP step yields a relative enrichment of the target epitope, and thus cannot provide any absolute quantification of modification levels or transcription factor occupancy. Second, while ChIP-seq can identify the genomic locations of a single modification or transcription factor separately, it cannot distinguish combinatorial modifications or co-occupancy on the same nucleosome and cannot distinguish whether a single modification or transcription factor originate from different alleles or cells. Nor can it directly relate histone marks to DNA methylation. Third, ChIP requires large amounts of input and the resulting data reflect a composite average over many cells and alleles. Hence, even coupled to the latest sequencing technologies, ChIP-based tools provide only qualitative insight into the patterns of an individual modification or transcription factor, and fall short of comparing their absolute levels and inter-relationships. These limitations hinder progress towards understanding human genome regulation because genes and genomic elements are defined and controlled by combinatorial chromatin states and dynamic interactions between transcription factors and chromatin regulators. Moreover, it is now evident that populations of cells are highly heterogeneous, requiring new technologies to study single cells and single molecules.

Thus there is a need for novel methods that would enable monitoring of the combinatorial pattern of histone modifications, nucleosome composition, transcription factor occupancy, and genomic location of single nucleosome particles to advance the understanding of gene regulation.

Citation or identification of any document in this application is not an admission that such document is available as prior art to the present invention.

SUMMARY OF THE INVENTION

It is an objective of the present invention to provide a robust single-molecule imaging system for chromatin mapping and functional genomics that overcomes inherent limitations of ChIP-seq with methods for (1) ascertaining the combinatorial modification states and genome-wide positions of individual chromatin molecules; (2) multiplexed analysis of small samples and single cells; and (3) exploring co-occupancy of transcription factors (TF) and chromatin modifications over gene regulatory elements in systematic fashion.

Protein-nucleic acid interactions are essential for regulation of the genome and cell function. It is another objective of the present invention to provide a robust single-molecule imaging system with methods for ascertaining combinatorial protein-nucleic acids interactions, such as RNA protein interactions.

Histone modifications are critical for the epigenetic control of genome function. Moreover, perturbations in chromatin regulators and histone modifications are strongly linked to human cancer. Therefore, it is an objective of the present invention to provide a novel single-molecule-based method to study the impact of the perturbation of individual chromatin regulators.

It is another objective of the present invention to provide methods to identify the interaction between nucleic acids and one or more of, e.g., a chromatin regulator, a methyltransferase, an acetylase, a deacetylase, a kinase, a phosphatase, a transcription factor, a transcription repressor, a transcription co-repressor, a transcription activator, a transcription co-activator, co-repressors, a silencer, a nuclear hormone receptor, one or more histones or a chromatin associated protein.

It is one objective of the present invention to provide methods to identify the protein or proteins associated with one or more DNA or RNA sequences.

It is another objective of the present invention to provide methods to study dynamic changes in the combinatorial pattern of histone modifications during embryonic stem cell differentiation and cellular transformation.

It is another objective of the present invention to provide a new technology to study the contribution of epigenetic mechanisms to cancer initiation and progression.

It is another objective of the present invention to provide for methods of screening drug targets and drug candidates based on changes in the combinatorial pattern of histone modifications.

In a first aspect, the present invention provides a method for analyzing chromatin isolated from cells. The method comprises: covalently linking an oligonucleotide sequence to a plurality of isolated chromatin fragments, wherein the oligonucleotide sequence is configured to bind to a capture molecule; purifying the isolated chromatin fragments linked to an oligonucleotide sequence by size exclusion; binding the purified chromatin fragments to a solid support comprising the capture molecule; incubating the solid support with a first set of at least one labeling ligand with specific binding affinity for a target molecule and wherein the labeling ligand includes a marker; and imaging the solid support, whereby the isolated chromatin fragments comprising the target molecule are visualized.

The oligonucleotide sequence may be any length, wherein the Tm of the sequence is 50, 51, 52, 52, 53, 54, 55, 56, 57, 58, 59, 60, 61, 62, 63, 64, or 65° C. Preferably, the Tm is between 55-60° C. The oligonucleotide sequence may comprise one strand that contains at least one uracil base. In a preferred embodiment, only one strand of the oligonucleotide sequence contains uracil. The oligonucleotide sequence may contain a binding molecule bound to one strand that binds to a capture molecule. The oligonucleotide sequence ligated to the isolated chromatin fragment may then be bound to the capture molecule on the solid surface. The binding molecule is on the opposite strand from the strand containing uracil. In preferred embodiments, the binding molecule bound to the oligonucleotide sequence may be biotin and the capture molecule streptavidin. In other preferred embodiments, the binding molecule may comprise ssDNA and the capture molecule is a complementary ssDNA. In one embodiment, the biotin is attached to the 3' end of the oligonucleotide sequence. In one embodiment, the 3' end of the oligonucleotide sequence has an additional ssDNA sequence. Not being bound by a theory, the 3' end of the strand of the oligonucleotide sequence comprising biotin or a 3' ssDNA sequence can be bound to the solid surface by the capture molecule and sequenced by hybridization of a primer, such that the primer is extended in a 5' to 3' direction. In another embodiment, the oligonucleotide sequence may include a sequence, wherein when the oligonucleotide sequence becomes ligated to itself a restriction enzyme site is created. In a preferred embodiment, the restriction enzyme site is for PacI. In one embodiment, the oligonucleotide sequence is phosphorylated at the 5' end of the strand attached to the binding molecule.

The oligonucleotide sequence may contain a marker. The marker may be a fluorescent marker. The marker may be attached to the oligonucleotide sequence via a disulfide bond that can be cleaved to release the marker. In one embodiment, the method further comprises imaging the solid support after binding of the isolated chromatin fragment to the capture molecule on the solid support, whereby the location of isolated chromatin fragments is determined. The method may further comprise cleaving of the marker from the oligonucleotide sequence and washing the solid support. The location of each isolated chromatin fragment bound to the solid support is now recorded in the image and the marker is no longer required. Not being bound by a theory, the image can be overlaid with subsequent images to link chromatin modifications to single isolated chromatin fragments. Not being bound by a theory, the location of isolated chromatin fragments on the solid support are determined.

The method may further comprise an additional step after imaging of the target molecules bound to the isolated chromatin fragments comprising washing the first labelling ligands from the solid support; incubating the solid support with a second set of at least one labeling ligand with specific binding affinity for a target molecule and wherein the labeling ligand includes a marker; and imaging the solid support, whereby the isolated chromatin fragments comprising the target molecule bound by the second set of labeling ligands are visualized. Not being bound by a theory, the solid support can be washed multiple times and the isolated chromatin fragments can be incubated with a plurality of labeling ligands.

In a preferred embodiment, the target molecule comprises first and second target molecules, wherein the first labeling ligand has specific binding affinity for the first target molecule and the first labeling ligand includes a first marker; wherein the second labeling ligand has specific binding affinity for the second target molecule and the second labeling ligand includes a second marker; whereby the first and second target molecules are multiplex-visualized.

In another preferred embodiment, the target molecule comprises first, second and third target molecules, wherein the first labeling ligand has specific binding affinity for the first target molecule and the first labeling ligand includes a first marker; wherein the second labeling ligand has specific binding affinity for the second target molecule and the second labeling ligand includes a second marker; wherein the third labeling ligand has specific binding affinity for the third target molecule and the third labeling ligand includes a third marker; whereby the three target molecules are multiplex-visualized.

The isolated chromatin fragments may be obtained by a method comprising: separating single cells into droplets formed by an aqueous solution in oil emulsion, wherein each droplet comprises a single cell, a nuclease, and a lysis buffer; and lysing cells within the droplets, whereby the nuclease digests the chromatin released from the cells, and wherein the oligonucleotide sequence is introduced into each of said droplet and wherein the oligonucleotide sequence is covalently linked within the droplet. The oligonucleotide sequence may comprise a unique barcode, whereby chromatin fragments in different droplets may be distinguished. The oligonucleotide sequence may comprise one marker selected from a plurality of markers, whereby chromatin fragments in different droplets may be distinguished. The introducing the oligonucleotide sequence may comprise injection into each droplet. The introducing the oligonucleotide sequence may comprise fusing a second droplet derived from a plurality of second droplets to each droplet, wherein each second droplet of the plurality of second droplets comprises an oligonucleotide sequence comprising a unique barcode. After the step of covalently linking an oligonucleotide sequence to a plurality of isolated chromatin fragments the method may further comprise breaking the emulsions. Not being bound by a theory, the cell where each isolated chromatin fragment originated can be determined by sequencing of the barcode.

The isolated chromatin fragments may be obtained by a method comprising: separating single cells into individual wells; lysing cells within each well; and digesting the lysed cells with a nuclease, wherein the oligonucleotide sequence is covalently linked within each well. The oligonucleotide sequence may comprise a unique barcode, whereby chromatin fragments in different wells may be distinguished. The oligonucleotide sequence may comprise one marker selected from a plurality of markers, whereby chromatin fragments in different wells may be distinguished.

The isolated chromatin fragments may be obtained by a method comprising treating cells with an agent that induces apoptosis.

The isolated chromatin fragments may be obtained by a method comprising: crosslinking cells; and digesting the lysed cells with a nuclease. After imaging the at least one target molecule, the method may further comprise reversing the crosslinks and sequencing the DNA.

The isolated chromatin fragments may be obtained by a method comprising: lysing at least one cell; and incubating the lysed cell with Tn5-transposase loaded with two tagmentation adapters configured for ligation to the oligonucleotide sequence. The chromatin fragments may be between 0.5 to 2 kb. The cells may be fixed before lysis.

The target molecule may comprise a histone modification, nucleotide modification, histone variant, chromatin remodeling factor, a methyl-transferase, an acetylase, a deacetylase, a kinase, a phosphatase, a ubiquitin ligase or a transcription factor. The method may further comprise immunoprecipitation of the isolated chromatin fragments with an antibody specific for a target molecule. The antibody specific for a target molecule comprises an antibody specific for a histone modification, nucleotide modification, histone variant, chromatin remodeling factor, a methyl-transferase, an acetylase, a deacetylase, a kinase, a phosphatase, a ubiquitin ligase or a transcription factor. The histone modification may be selected from the group consisting of H2B Ser 14 (Phos), H3 Ser 10 (Phos), H3 Lys 9 (Me), H3 Lys 27 (Me), H3 Lys 36 (Me), H3 Lys 79 (Me), H4 Lys 20 (Me), H3 Lys 4 (Me), H3 Lys 9 (Ac), H3 Lys 14 (Ac), H3 Lys 23 (Ac), H4 arg 3 (Me), H3 Lys 27 (Ac), H4 arg 3 (Me), H4 lys 5 (Ac), H4 Ser 2 (phos), H4 Arg 3(me), H4 Lys 5 (Ac) and H3 Lys 18 (Ac). The nucleotide modification may be selected from the group consisting of 5-methyl- (5-mC), 5-hydroxymethyl- (5-hmC), 5-formyl- (5-fC) and 5-carboxy- (5-caC) cytosine. The histone variant may be selected from the group consisting of macroH2A1.1, macroH2A1.2, H2AZ, H2AX, H3.1 and H3.3. Enhancer like regions may be immunoprecipitated with an antibody specific for H3K27ac and promoters may be immunoprecipitated with an antibody specific for H3K4me3. The nuclease may be micrococcal nuclease.

The isolated chromatin fragments may be obtained by a method comprising: isolating a nuclei fraction from a population of cells; and digesting the isolated nuclei fraction with a nuclease. The method may further comprise immunoprecipitation of the isolated chromatin fragments from the digested nuclei with an antibody specific for a target molecule.

The isolated chromatin fragments may be obtained by a method comprising: separating single cells into droplets in an aqueous solution in oil emulsion, wherein each droplet comprises a single cell, a nuclease, a ligase and no more than one bead comprising a unique barcode sequence; lysing the cells within the droplets, wherein the nuclease digests the genomic DNA and the ligase ligates chromatin fragments to a barcode sequence; breaking the emulsions; and removing the barcode sequence from the bead, whereby isolated chromatin fragments are generated comprising a unique barcode sequence that is configured to be further ligated to the oligonucleotide sequence. Not being bound by a theory, the cell where each isolated chromatin fragment originated can be determined by sequencing of the barcode.

The antibody used for immunoprecipitating isolated chromatin fragments specific for a target molecule may comprises an antibody specific for a chromatin regulator, a methyl-transferase, an acetylase, a deacetylase, a kinase, a phosphatase, a transcription factor, a transcription repressor, a transcription co-repressor, a transcription activator, a transcription co-activator, co-repressors, a silencer, a nuclear hormone receptor, or a chromatin associated protein. The antibody may be specific for a histone modification. The antibody may be specific for DNA methylation at a CpG site.

Not being bound by a theory, the nuclease digests DNA not bound by a nucleosome. Not being bound by a theory each nucleosome contains 142 base pairs of genomic DNA wrapped around an octamer containing four core histones. Not being bound by a theory, different concentrations of nuclease may be used to generate oligo nucleosomes and mononucleosomes. In preferred embodiments, the nuclease may be micrococcal nuclease (Mnase).

The purification by size exclusion may be by performing a glycerol gradient, a sucrose gradient, or size exclusion chromatography. Not being bound by a theory, isolated chromatin fragments can be separated by their mass. In one embodiment, the sucrose gradient or glycerol gradient is from 5-40%, 5-35%, 5-30%, 10-40%, 10-35%, preferably 10-30%.

The labeling ligand may be an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may be an aptamer.

Any of the markers may be a fluorescent marker. In preferred embodiments, markers imaged at the same time may emit different wavelengths. The fluorescent dyes may have different fluorescent lifetimes. In preferred embodiments, the dyes are selected from Alexa 488, Alexa 488, Alexa 555, Alexa 640, CY3, CY5, an Atto Dye, or a Pacific Dye. In a more preferred embodiment, the labeling ligand comprises Alexa 555 and Alexa 640.

The imaging may be any fluorescent microscopy method. In a preferred embodiment, total internal reflection fluorescence microscopy (TIRFM) is used. The imaging may include imaging the markers at more than one time point. The imaging may include imaging the markers in a time-lapse fashion. Not being bound by a theory, individual antibodies may associate and dissociate with a target molecule. Antibodies may have different on/off rates. Imaging time and the amount of images may be determined by the on/off rates. Not being bound by a theory more images would be required when using an antibody with a faster on/off rate. Not being bound by a theory, when more than one antibody is incubated at the same time, antibodies binding target molecules on the same histone may prevent both from binding simultaneously. In one embodiment, imaging may be performed at more than one time point, at least two, three, four, five, ten, twenty, or a hundred time points. The time points may be every second, minute, 10 minutes, 15 minutes, 30 minutes, or hour. The total imaging time may be 10 minutes, 1 hour, 2 hours, 3 hours, 4 hours, 10 hours, or 24 hours. Not being bound by a theory, the temperature may affect the binding kinetics of labeling ligands. Not being bound by a theory, binding of antibodies at higher temperatures will result in faster kinetics. Imaging may be adjusted based on the temperature used. The temperature may be room temperature. The temperature may be 4° C., 10° C., 15° C., 20° C., 25° C., 30° C., 35° C., 37° C., or 40° C. In preferred embodiments, the temperature is 25° C. In one embodiment, the presence of a target molecule is determined by the capturing of at least one image wherein the labeling ligand is bound to an isolated chromatin fragment.

In another aspect, the method may provide for sequencing of the DNA in each isolated chromatin fragment. In one embodiment, the method comprises: removing proteins from the isolated chromatin fragments bound to the solid support; treating the sample with a uracil excision reagent; hybridizing a primer complementary to the oligonucleotide sequence; and sequencing the DNA encompassed by the isolated chromatin fraction using sequencing by synthesis. Proteins may be removed from the isolated chromatin fragments by treating with a high salt solution. The proteins are removed by incubating the solid support with a salt solution, wherein the ionic strength is equal to a solution of NaCl with a concentration between 0.75M and 2M. The salt may be sodium chloride, potassium chloride, or ammonium sulfate. In preferred embodiments, the salt solution is 2M NaCl. Proteins mat also be removed by treatment with a proteinase. The proteinase may by proteinase K.

The uracil excision reagent may be a mixture of uracil DNA glycosylase (UDG) and the DNA glycosylase-lyase Endonuclease VIII. Not being bound by a theory, both enzymes are required to remove the entire uracil nucleotide from the oligonucleotide sequence. Not being bound by a theory, the removal of uracil generates single stranded DNA capable of hybridization to a sequencing primer. Not being bound by a theory DNA polymerase used to sequence the opposite strand can cause strand displacement in order to extend the hybridized primer. Not being bound by a theory, the isolated chromatin fragment would be released from the solid support under conditions where the entire DNA strand was converted to ssDNA. Not being bound by a theory, the method of the present invention allows the sequencing to be performed on the solid support. The sequencing by synthesis may include labeled nucleotides that are individually added to each cycle of sequencing. The nucleotides may be labeled with different fluorescent dyes, such that the four nucleotides may be added at the same time. The incorporated label can be visualized after each cycle, thus indicating the nucleotide sequence. The label may then be cleaved from the incorporated nucleotides and the next cycle can begin. Not being bound by a theory, sequencing of the DNA on the solid support allows the sequence to be directly linked to the bound labeling ligands for individual isolated chromatin fragments.

Not being bound by a theory, the solid support needs to be stable enough so that the DNA from the isolated chromatin fragments remains bound throughout the sequencing process. Any method of functionalizing a glass surface as known in the art is possible. In one embodiment, the capture molecule is bound to the solid support by being linked to oligonucleotide sequence linked to the solid platform. In another embodiment, the capture molecule is bound to the solid support by being linked to PEG present on the solid surface.

In another embodiment, sequencing may be performed by a method comprising: removing proteins from the isolated chromatin fragments bound to the solid support; treating the solid support with formamide; hybridizing a primer complementary to the oligonucleotide sequence; and sequencing the DNA encompassed by the isolated chromatin fraction using sequencing by synthesis. The proteins are removed by incubating the solid support with a salt solution, wherein the ionic strength is equal to a solution of NaCl with a concentration between 0.75M and 2M.

In another aspect, the method may provide for a method of sequencing isolated chromatin fragments bound by specific labeling ligands by selecting and removing isolated chromatin fragments from the solid support, wherein the solid support contains remaining isolated chromatin fragments that were bound by a common labeling ligand; isolating the DNA associated with the remaining chromatin fragments; and sequencing the isolated DNA, whereby genomic DNA associated with a specific target molecule is determined. The capture molecule or binding molecule may be linked to a photocleavable linker. Based on the location of isolated chromatin fragments of interest on the solid support as determined by imaging, a laser can be used to remove isolated chromatin fragments by activating the photocleavable linker. Not being bound by a theory, the remaining DNA can be removed and sequenced using any standard sequencing method.

The isolated chromatin fragments may include at least one nucleosome. The isolated chromatin fragments may be mononucleosomes. The isolated chromatin fragments may be a stretch of 2-5 adjacent nucleosomes.

The oligonucleotide sequence may be linked to biotin and the capture molecule comprises streptavidin. The oligonucleotide sequence may include a ssDNA tail and the capture molecule is a complementary ssDNA oligonucleotide sequence. The solid support may be a glass slide. The solid support may comprise biotin attached to a PEG surface. Not being bound by a theory, the PEG surface prevents non-specific binding of labeling ligands to the solid support. Not being bound by a theory, the PEG surface does not stably bind the biotin under sequencing conditions. The solid support may comprise biotin bound to an oligo that is conjugated to a solid surface. Not being bound by a theory, the biotin is stably bound during sequencing conditions. Not being bound by a theory the surface binds labeling ligands non-specifically and needs to be blocked. In a preferred embodiment the solid support is blocked with spermine.

The solid support may comprise slides, arrays, channels, beads, bubbles, and the like that contain the capture molecule. In one embodiment, a flow cell houses the solid support. The solid support may comprise glass or fused silica slide. The present invention can be used with any surface compatible with fluorescence microscopy, preferably TIRF, that is functionalized with the capture molecule. Methods of binding a capture molecule to a glass surface are known in the art. All three types of functionalized glass slides (amine, aldehyde and epoxy) may be used. Preferred solid supports are coated with an epoxide, polyelectrolyte multilayer, or other coating suitable to bind a capture molecule. In a highly-preferred embodiment, the solid support is coated with an epoxide and nucleic acids linked to the capture molecules are attached directly via an amine linkage. In other embodiments, the epoxide coating is derivatized. For example, epoxide can be derivatized with streptavidin and the oligonucleotide sequence can bear a biotin terminus that will attach to the streptavidin. Alternatively, other binding pairs, such as antigen/antibody or receptor/ligand pairs, may be used. Ideally, an epoxide surface is passivated in order to reduce background. Passivation can be conducted by exposing the surface to a molecule that attaches to the open epoxide ring. Examples of such molecules include, but are not limited to, amines, phosphates, and detergents.

The target molecule may be a modified histone, a core histone, or a histone variant. The modified histone may be histone methylation, histone mono-methylation, histone di-methylation, histone tri-methylation, histone tetra-methylation, histone acetylation, histone phosphorylation, or histone ubiquitination.

The imaging buffer may be any imaging buffer compatible with TIRF that allows specific binding of a labeling ligand. Not being bound by a theory, different labeling ligands have different specificities for a target molecule. The buffer may be adjusted to remove non-specific binding. The buffer may be adjusted with methods known in the art for immunoprecipitation using antibodies. In one embodiment the salt concentration is adjusted. In one embodiment, detergent is added. In one embodiment, a stabilizing protein is added. Not being bound by a theory, some antibodies do not work when they are alone. In one embodiment the imaging buffer comprises 0.1 mg/ml BSA. The pH of the imaging buffer may also be adjusted. In one embodiment, the imaging buffer comprises phosphate buffered saline (PBS), Tris, HEPES, PIPES, IVIES, or any buffering agent with a pka between 6.0 to 8.06. In preferred embodiments, the imaging buffer is optimized for each labeling ligand. The imaging buffer may also be formulated for improved imaging. In one embodiment, the imaging buffer may contain an oxygen scavenging system (10% glucose, 800 µg/ml glucose oxidase, 40 µg/ml catalase) to reduce photobleaching and/or 2 mM Trolox (Sigma) to reduce photoblinking of the dyes (Rasnik et al., 2006).

The method may further comprise treating the chromatin fragments bound to the solid support with a CRISPR-Cas system comprising a guide RNA specific for a sequence of interest, whereby genomic DNA associated with a specific target molecule is determined. The CRISPR-Cas system may comprise a fluorescent marker, whereby the sequence of interest of a chromatin fragment is determined. The CRISPR-Cas system may comprise a nickase, wherein the nickase generates nicks at the sequence of interest, wherein the nicks are repaired with fluorescent nucleotides and DNA polymerase, whereby the sequence of interest of a chromatin fragment is determined.

In another aspect, the present invention provides for a kit comprising: a solid support; and an oligonucleotide sequence configured to be ligated to an isolated chromatin fragment and configured to bind to the capture molecule on the solid support. The kit may also include: imaging buffer; uracil DNA glycosylase (UDG) and DNA glycosylase-lyase Endonuclease VIII; labeled nucleotides; and optionally instructions.

In another aspect, the present invention provides for a method of screening chemical compounds that modulate chromatin modifying enzymes comprising: incubating a population of cells with a chemical compound; incubating another population of cells with a control vehicle; isolating chromatin fragments from the respective populations of cells; covalently linking an oligonucleotide sequence to each of the isolated chromatin fragments, wherein the oligonucleotide sequence is configured to bind to a capture molecule; purifying the isolated chromatin fragments linked to an oligonucleotide sequence by size exclusion; binding the purified chromatin fragments from each population to a separate solid support comprising the capture molecule; incubating each solid support with a first set of at least one labeling ligand with specific binding affinity for a target histone modification or histone variant, and wherein the labeling ligand includes a marker; and imaging the solid supports, whereby a change in the percentage of isolated chromatin fragments bound by the labeling ligand indicates that the chemical compound modulates the activity of the chromatin modifying enzyme.

In another aspect, the present invention provides for a method for analyzing RNA/protein complexes comprising: covalently linking an oligonucleotide sequence to a plurality of isolated RNA/protein complexes, wherein the oligonucleotide sequence is configured to bind to a capture molecule; purifying the RNA/protein complexes linked to an oligonucleotide sequence by size exclusion; binding the purified chromatin fragments to a solid support comprising the capture molecule; incubating the solid support with a first set of at least one labeling ligand with specific binding affinity for a target molecule and wherein the labeling ligand includes a marker; and imaging the solid support, whereby the isolated chromatin fragments comprising the target molecule are visualized. The oligonucleotide sequence may comprise one strand that comprises at least one uracil base. The oligonucleotide sequence may contain a marker and wherein the method further comprises step c' after step c, wherein step c' may comprise imaging the solid support, whereby the location of RNA/protein complexes is determined. The method may further comprise cleaving of the marker from the oligonucleotide sequence and washing the solid support. The method may further comprise step f, wherein step f comprises: washing the solid support; incubating the solid support with a second set of at least one labeling ligand with specific binding affinity for a target molecule and wherein the labeling ligand includes a marker; and imaging the solid support, whereby the RNA/protein complexes comprising the target molecule are visualized. Step f may be repeated at least one additional time. The target molecule may comprise first and second target molecules, wherein the first labeling ligand has specific binding affinity for the first target molecule and the first labeling ligand includes a first marker; wherein the second labeling ligand has specific binding affinity for the second target molecule and the second labeling ligand includes a second marker; at step e the first and second target molecules are multiplex-visualized. The target molecule may comprise first, second and third target molecules, wherein the first labeling ligand has specific binding affinity for the first target molecule and the first labeling ligand includes a first marker; wherein the second labeling ligand has specific binding affinity for the second target molecule and the second labeling ligand includes a second marker; wherein the third labeling ligand has specific binding affinity for the third target molecule and the third labeling ligand includes a third marker; at step e the three target molecules are multiplex-visualized. The method may further comprise: removing proteins from the RNA/protein complexes bound to the solid support; treating the solid support with formamide; hybridizing a primer complementary to the oligonucleotide sequence; and sequencing the RNA encompassed by the isolated chromatin fraction using sequencing by synthesis. The sequencing may be performed with a reverse transcriptase.

In another aspect, the present invention provides a diagnostic method comprising analyzing cell-free chromatin fragments comprising: covalently linking an oligonucleotide sequence to a plurality of chromatin fragments obtained from a biological sample, wherein the oligonucleotide sequence is configured to bind to a capture molecule; binding the chromatin fragments to a solid support comprising the capture molecule; incubating the solid support with a first set of at least one labeling ligand with specific binding affinity for a target molecule and wherein the labeling ligand includes a marker; and imaging the solid support, whereby the chromatin fragments comprising the target molecule are visualized. The oligonucleotide sequence may comprise one strand comprising at least one uracil base. The oligonucleotide sequence may contain a marker and the method may further comprise step b' after step b, wherein step b' comprises imaging the solid support, whereby the location of the chromatin fragments is determined. The method may further comprise cleaving of the marker from the oligonucleotide sequence and washing the solid support, whereby the marker is removed.

The target molecule may comprise first and second target molecules, wherein the first labeling ligand has specific binding affinity for the first target molecule and the first labeling ligand includes a first marker; wherein the second labeling ligand has specific binding affinity for the second target molecule and the second labeling ligand includes a second marker; whereby the first and second target molecules are multiplex-visualized. The target molecule may comprise first, second and third target molecules, wherein the first labeling ligand has specific binding affinity for the first target molecule and the first labeling ligand includes a first marker; wherein the second labeling ligand has specific binding affinity for the second target molecule and the second labeling ligand includes a second marker; wherein the third labeling ligand has specific binding affinity for the third target molecule and the third labeling ligand includes a third marker; whereby the three target molecules are multiplex-visualized. The method may further comprise digesting the chromatin fragments with a nuclease. The nuclease may be micrococcal nuclease.

The chromatin fragments may be obtained from a biological sample selected from the group consisting of sera, plasma, lymph, blood, blood fractions, urine, synovial fluid, spinal fluid, saliva, circulating tumor cells (CTC) and mucous. The diagnostic method may be used to detect a disease or risk for a disease associated with modified, cell-free nucleosomes selected from the group consisting of pre-malignant and malignant neoplasms, histocytoma, glioma, astrocyoma, osteoma, lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma, leukemias, systemic lupus erythematosus, psoriasis, bone diseases, fibroproliferative disorders of connective tissue, cataracts and atherosclerosis. The diagnostic method may be used to detect cancer or risk for cancer. The biological sample may be from a subject identified to be suffering from or at risk for developing cancer. The cancer may be histocytoma, glioma, astrocyoma, osteoma, lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma or leukemia.

The target molecule may be a histone modification. The method may comprise detecting bivalent histone modifications, whereby if a greater proportion of nucleosomes with bivalent histone modifications is detected as compared to random histone modifications cancer or increased risk of cancer is indicated. The bivalent histone modifications may be H3K27me3 and H3K4me3. The histone modification may be selected from the group consisting of H2B Ser 14 (Phos), H3 Ser 10 (Phos), H3 Lys 9 (Me), H3 Lys 27 (Me), H3 Lys 36 (Me), H3 Lys 79 (Me), H4 Lys 20 (Me), H3 Lys 4 (Me), H3 Lys 9 (Ac), H3 Lys 14 (Ac), H3 Lys 23 (Ac), H4 arg 3 (Me), H3 Lys 27 (Ac), H4 arg 3 (Me), H4 lys 5 (Ac), H4 Ser 2 (phos), H4 Arg 3(me), H4 Lys 5 (Ac) and H3 Lys 18 (Ac).

The target molecule may be a nucleotide modification. The nucleotide modification may be selected from the group consisting of 5-methyl- (5-mC), 5-hydroxymethyl- (5-hmC), 5-formyl- (5-fC) and 5-carboxy- (5-caC) cytosine.

The target molecule may be a histone variant. The histone variant may be selected from the group consisting of macroH2A1.1, macroH2A1.2, H2AZ, H2AX, H3.1 and H3.3.

The method may further comprise sequencing of the DNA associated with single nucleosomes, whereby nucleosome composition, modification and/or nucleotide sequence is determined for single nucleosomes obtained from cell-free chromatin fragments. The sequencing may comprise sequencing of bisulfite converted DNA. Not being bound by a theory, DNA bound to a solid surface may be treated with sodium bislufite to convert unmethylated cytosines to uracil. Upon sequencing, methylated CpG dinucleotides may be detected by analyzing the sequence obtained after bisulfite conversion and comparing to genomic sequences. Active and inactive genes may be determined by a method comprising analyzing gene sequences bound to nucleosomes comprising histone modifications indicative of active chromatin or inactive chromatin. The modifications associated with gene silencing may be H3 Lys 9 (Me), H3 Lys 27 (Me), H3 Lys 36 (Me), H3 Lys 79 (Me) and H4 Lys 20 (Me) and wherein modifications associated with gene activation may be H3 Lys 4 (Me), H3 Lys 9 (Ac), H3 Lys 14 (Ac), and H3 Lys 23 (Ac). The genes may comprise an oncogene. The genes may comprise a tumor suppressor.

The method may further comprise sequencing of the DNA associated with single nucleosomes, wherein the cell-free chromatin fragments are used in a method of prenatal screening. The target molecule may be histone H3.1, whereby fetal nucleosomes are identified. The prenatal screening may be for a disease selected from the group consisting of Trisomy 13, Trisomy 16, Trisomy 18, Klinefelter syndrome (47, XXY), (47, XYY) and (47, XXX), Turner syndrome, Down syndrome (Trisomy 21), Cystic Fibrosis, Huntington's Disease, Beta Thalassaemia, Myotonic Dystrophy, Sickle Cell Anemia, Porphyria, Fragile-X-Syndrome, Robertsonian translocation, Angelman syndrome, DiGeorge syndrome and Wolf-Hirschhorn Syndrome. The cell-free chromatin fragments may be obtained from a cervical mucus sample. The cervical mucus sample may be treated with a mucinase, whereby trapped chromatin is released. The cervical mucus sample may be treated with an agent that induces apoptosis, whereby fetal nucleosomes are released.

The labeling ligand may comprise an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may be an aptamer. The marker may be a fluorescent marker. The fluorescent marker may be Alexa 488, Alexa 555, Alexa 640, CY3, CY5, an Atto Dyes, or a Pacific Dye. The labeling ligand may be Alexa 555 and Alexa 640.

The imaging may comprise total internal reflection fluorescence microscopy (TIRFM). The imaging may comprise imaging the markers at more than one time point. The imaging may comprise imaging the markers in a time-lapse fashion. Up to 20 images may be taken over a period of up to 24 hours.

The sequencing may comprise: removing proteins from the chromatin fragments bound to the solid support; treating the sample with a uracil excision reagent; hybridizing a primer complementary to the oligonucleotide sequence; and sequencing the DNA encompassed by the chromatin fragments using sequencing by synthesis. The uracil excision reagent may be Uracil DNA glycosylase (UDG) and the DNA glycosylase-lyase Endonuclease VIII. The proteins may be removed by incubating the solid support with a salt solution, wherein the ionic strength is equal to a solution of NaCl with a concentration between 0.75M and 2M.

The sequencing may comprise: removing proteins from the chromatin fragments bound to the solid support; treating the solid support with formamide; hybridizing a primer complementary to the oligonucleotide sequence; and sequencing the DNA encompassed by the chromatin fragments using sequencing by synthesis. The proteins may be removed by incubating the solid support with a salt solution, wherein the ionic strength is equal to a solution of NaCl with a concentration between 0.75M and 2M.

The cell-free chromatin fragments may comprise at least one nucleosome. The cell-free chromatin fragments may be mononucleosomes. The cell-free chromatin fragments may be a stretch of 2-5 adjacent nucleosomes. The oligonucleotide sequence may be linked to biotin and the capture molecule comprises streptavidin. The oligonucleotide sequence may include a ssDNA tail and the capture molecule may be a complementary ssDNA oligonucleotide sequence. The solid support may comprise biotin linked to a glass surface. The method may further comprise purifying the isolated chromatin fragments linked to an oligonucleotide sequence by size exclusion.

In another aspect, the present invention provides a diagnostic method for analyzing RNA/protein complexes comprising: covalently linking an oligonucleotide sequence to a plurality of RNA/protein complexes obtained from a biological sample, wherein the oligonucleotide sequence is configured to bind to a capture molecule; purifying the RNA/protein complexes linked to an oligonucleotide sequence by size exclusion; binding the purified chromatin fragments to a solid support comprising the capture molecule; incubating the solid support with a first set of at least one labeling ligand with specific binding affinity for a target molecule and wherein the labeling ligand includes a marker; and imaging the solid support, whereby the isolated chromatin fragments comprising the target molecule are visualized. The sequencing may be performed with a reverse transcriptase. The RNA/protein complexes may be obtained from exosomes.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1A-1F. Single-molecule detection of post-translational modifications on nucleosomes. (A) Experimental scheme: (1) Nucleosomes from cells are prepared by Micrococcal Nuclease (MNase) digestion. Gel depicts nucleosomal DNA fragments of expected lengths; (2) Free DNA ends of nucleosomes are ligated to fluorescent, biotinylated oligonucleotide adaptors; (3) Adaptor-ligated mono-nucleosomes are purified on a glycerol gradient and captured on PEG-streptavidin coated slides. (4) Nucleosome positions on the surface are imaged by TIRF microscopy, and then the fluorophore is cleaved from the adaptor. (5) Attached nucleosomes are incubated with fluorescently-labeled antibodies to histone modifications. (6) Time-lapse images detect repeated binding and dissociation events and are integrated to score modified nucleosomes (FIG. 7). (B-D) HEK293 cells were treated with HDAC inhibitor. (B) Single-Molecule detection of labeled nucleosomes (Alexa555, green) bound by labeled H3K9ac antibodies (Alexa647, red). (C) Proportion of nucleosomes marked by H3K9ac under each condition is determined by single-molecule counting. (D) Western blot confirms increased H3K9ac in treated cells. (E-F) Recombinant unmodified nucleosomes and H3K27me3-modified peptide were probed with the indicated antibodies. The results support the specificity of the single-molecule assay. (F) Single-molecule detection of labeled H3K27me3 peptide (TAMRA, green spots) (SEQ ID NO: 8) with labeled H3K27me3 antibodies (Alexa647, red spots) at a single time point.

FIG. 2A-2G. Single-molecule imaging of symmetric and asymmetric bivalent nucleosomes. (A) Single-molecule imaging was used to decode the modification states of nucleosomes from pluripotent ESCs, embryoid bodies (EB) and lung fibroblasts (lung). Left: Colored bars indicate proportions of nucleosomes with H3K27me3 (red) or H3K4me3 (green). Right: Black bars indicate relative over- or under-representation of bivalent nucleosomes. Results are presented as the Log 2 ratio of the observed proportion of bivalent nucleosomes divided by the expected random association of these two marks (random association=fraction H3K27me3*fraction H3K4me3). (B) Nucleosomes from a T-cell acute lymphoblastic leukemia line, HEK293 cells and glioblastoma stem cells were decoded as in (A). (C) Nucleosomes from an acute leukemia line with a loss-of-function EZH2 mutation, a lymphoma line with a gain-of-function EZH2 mutation, and the lymphoma cells treatment with EZH inhibitor GSK126. (D) Magnified TIRF image overlay reveals three nucleosomes, one with H3K27me3 (red), one with H3K4me3 (green), and one with concomitant (bivalent) modifications. (E) Symmetry of bivalent nucleosomes was investigated by probing individual histone H3 molecules isolated from ESCs, biotinylated and spatially distributed on the surface. Image depicts H3K27me3 and H3K4me3 antibody binding to the histone molecules. Concomitantly marked H3 tails exist, but are rare relative to bivalent nucleosomes. This suggests that a majority of bivalent nucleosomes are asymmetrically modified with H3K27me3 and H3K4me3 on opposite H3 tails. (F-G) The lymphoma cell line with gain-of-function EZH2 was treated with the EZH2 inhibitor GSK126 for 3 days. (F) Single nucleosomes were decoded for H3K27me3 and H3K4me3. (G) Pie charts demonstrate preferential loss of H3K27me3 from bivalent nucleosomes.

FIG. 3A-3D. Higher-order modification states altered by developmental specification and epigenetic inhibitors. (A) Individual nucleosomes from ESCs and lung fibroblasts decoded for H3K4me3, H3K27me3, H3K27me2 and H3K27ac, as described in FIG. 1. Nucleosomes were probed with two fluorescently-labeled antibodies for 3 hours, washed to remove antibodies, and then probed with two new fluorescently-labeled antibodies. Bars depict fraction of nucleosomes marked with the indicated modification. (B) Bars indicate relative over- or under-representation of the indicated modification pair, relative to random expectation, as in FIG. 2A. (C) Proposed model relates observed differences in combinatorial histone modifications between cell types to the hyperdynamic chromatin state in ESCs. (D) ESCs were treated with DMSO (control), HDAC inhibitor (Sodium butyrate) or p300 inhibitor (C646). Nucleosomes were isolated and decoded with antibodies targeting H3K27me3, H3K4me3, H3K9ac and H3K27ac. Plot depicts relative differences between drug treatment and control for each single modification or for the combination of H3K27ac and H3K4me3.

FIG. 4A-4C. Genomic positions of modified nucleosomes determined by single-molecule sequencing. (A) Experimental scheme: (1) Nucleosomes are captured and probed for their modification state, as in FIG. 1A. (2) Proteins are removed from the surface by increasing salt concentration. (3) The enzyme USER is applied to excise uracil bases incorporated into the non-biotinylated adaptor strand and expose a known sequence (SEQ ID NOS 9-10, respectively, in order of appearance) (4) Complementary primer is hybridized to the adaptor. Image shows single molecule detection of nucleosomal DNA (labeled with Alexa647, red) and primer (Alexa555, green). (5) Direct single-molecule DNA sequencing-by-synthesis is carried out by successive rounds of incorporation and detection of fluorescently-labeled nucleotide terminators (44). Images demonstrate two sequencing cycles: incorporation of thymine, followed by cleavage of fluorophore and terminator, followed by incorporation of cytosine. (6) Data processing: for each x-y coordinate on the surface, sequence data is analyzed and integrated with the initial images scoring antibody binding and modification states of the corresponding nucleosomal histones (see Materials and Methods). (B) Single-molecule reads were aligned to the genome. Plot indicates the proportion of H3K27me3-modified nucleosome reads ('detected') or un-modified nucleosome reads ('undetected') that aligned to H3K27me3-enriched regions per conventional ChIP-seq. (C) Genomic intervals from HOXA and HOXC gene clusters are shown along with conventional H3K27me3 ChIP-seq tracks. Single-molecule reads that aligned to these regions are indicated, along with the modification status of the corresponding nucleosome (detected=H3K27me3; undetected=unmodified). These data establish proof-of-principle for simultaneously decoding combinatorial modification states and genomic position of individual nucleosomes.

FIG. 7A-7F. Time-lapse images detect repeated antibody binding and dissociation events. (A) Mono-nucleosomes were extracted from HEK293 cells, labeled and distributed on the surface as described in FIG. 1A. Single molecule detection of nucleosomes (Alexa555, green spots) and H3K9ac antibodies (Alexa647, red spots) revealed that while nucleosome positions were fixed, the pattern of H3K9ac antibody binding changes over time. Shown are images taken at 15, 30 and 45 minutes after addition of antibodies. (B-F) Nucleosomes from ESCs were distributed on the surface and incubated with antibodies targeting H3K27me3 (B, D, F) or H3K4me3 (C, E). Time lapse images were taken every 15 minutes. A total of 10,000 individual binding events were analyzed for each antibody. (B-C) Number of binding events detected at each time point. Equilibrium of binding and dissociation of antibodies is achieved at 45 minutes for H3K27me3, and 75 minutes for H3K4me3. Later images show mild reduction in signal due to photo bleaching. (D-E) For each nucleosome, the number of binding events by antibody was calculated in a total of 8 images taken during the time course of the experiment (30-135 minutes). Graph depicts a histogram of the number of images in which each nucleosome is bound by the antibody. Due to repeated binding and dissociation events, most of the nucleosomes are bound more than once. However, very few nucleosomes are bound in all the images. (F) Example of the binding and dissociation pattern over time (min) for H3K27me3 antibody at five nucleosomes. Red spot represents a binding event.

FIG. 14A-14B. Single-molecule DNA sequencing-by-synthesis. (A) A single stranded biotinylated oligonucleotide was anchored to the surface. Oligo sequence contained a universal primer site (poly A) followed by 50 nucleotides; starting with the nucleotides G, G and T (see Materials and Methods). Applicants performed primer hybridization (primer sequence: poly T followed by C) and single-molecule DNA sequencing-by-synthesis. Shown are the first 5 cycles, demonstrating high incorporation of C and A, complementary to the oligonucleotide sequence. Very low unspecific incorporation of the other nucleotides is observed. Oligos were sequenced for a total of 120 cycles to verify the specificity of the sequencing reaction. (B) Adaptor-ligated nucleosomes from ESCs were prepared as in FIG. 1, distributed on the surface and imaged. Next, surface was treated with high salt followed by incubation with USER, as in FIG. 4. Fluorescently Labeled primer was allowed to hybridize to nucleosomal DNA molecules on the surface and imaged. Applicants than continued with single-molecule DNA sequencing-by-synthesis: shown are the first 3 cycles (for each sequencing cycle approximately 25% of template spots show base addition, assuming random DNA sequences on the surface).

FIG. 16. illustrates an exemplary embodiment for attaching streptavidin to a solid surface. Epoxy silane is deposited on a glass surface. The epoxy binds to the 3' end of an oligo containing a 3' amine group. The oligo is bound by 2× biotin at the 5' end.

DETAILED DESCRIPTION OF THE INVENTION

Figure 1A:
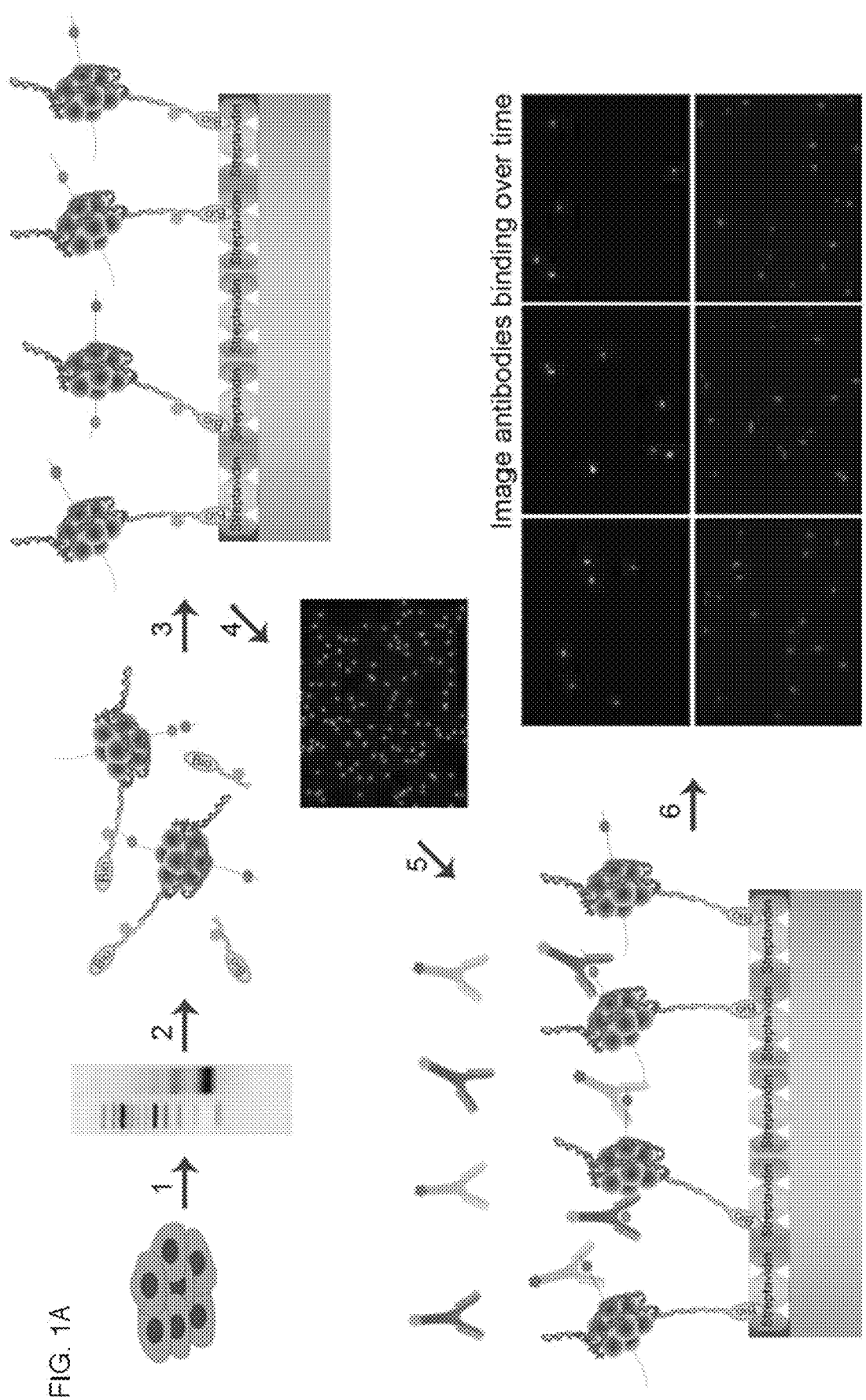

The term "isolated chromatin fragment' refers to any segment of genomic DNA isolated from a cell that is in association with a nuclear protein. Exemplary chromatin fragments may be oligonucleosomes, mononucleosomes, centromeres, telomeres or genomic DNA bound by a transcription factor or chromatin remodeling factor.

The term "purified", "isolated" and like terms refers to the isolation of a molecule or compound in a form that is substantially free (at least 60% free, preferably 75% free, and most preferably 90% free) from other components normally associated with the molecule or compound in a native environment.

The term "disease state" is intended to encompass any condition that is associated with an impairment of the normal state of a living animal or plant including congenital defects, pathological conditions such as cancer, and responses to environmental factors and infectious agents (bacterial, viral, etc.).

The term "modified histone" refers to a histone protein, wherein one or more of the amino acid residues have been modified post-translationally. Examples of post translation modifications include, but are not limited to, histone modifications including lysine mono-, di- and tri-methylation, lysine acetylation, Arginine mono-methylation and symmetric or asymmetric di-methylation, citrullination, ubiquitinylation, serine or threonine phosphorylation and proline isomerization. It will be recognized by those skilled in the art that these and other histone posttranslational modifications can exert activating or repressive effects on gene expression. Histone proteins include, but are not limited to H1, H2A, H2B, H3, H4, and any variants thereof. Histones are preferably modified at the last 30 amino acid residues of the amino terminus.

The term "transcription factor" refers to any protein or protein complex or protein nucleic acid complex required for transcription. Transcription factors include, but are not limited to a general transcription factor, an activator, a repressor, the mediator complex, an activator complex, a repressor complex, or any component of a multiprotein complex effecting transcription.

The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., histone modification binding. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

"Specific binding" of an antibody means that the antibody exhibits appreciable affinity for a particular antigen or epitope and, generally, does not exhibit significant crossreactivity.

Bisulfite sequencing is a commonly used method in the art for generating methylation data at single-base resolution. The term "bisulfite conversion" refers to a biochemical process for converting unmethylated cytosine residue to uracil residues, whereby methylated cytosine residues are preserved. "Bisulfite conversion" may be carried out computationally from a nucleic acid sequence contained in a computer file (such as those in FASTA, FASTQ or any file format known in the art), wherein all cytosine residues in a sequence of interest are changed to thymine or uracil residues. Exemplary reagents for bisulfite conversion include sodium bisulfite and magnesium bisulfite. "Bisulfite reagent" refers to a reagent comprising bisulfite, disulfite, hydrogen sulfite or combinations thereof, useful as disclosed herein to distinguish between methylated and unmethylated CpG dinucleotide sequences.

Advantageous embodiments of the invention include cells, cell lines and cells from transgenic organisms (e.g., plants, fungi, animals). Any prokaryotic or eukaryotic cells can be employed, including, but not limited to, bacterial, plant, fish, yeast, algae, insect, worm or mammalian cells. Further preferred embodiments include cells and cell lines which include but are not limited to plant cells, insect cells, bacterial cells, yeast cells, viral cells, human cells, primate cells, rat cells, mouse cells, zebrafish cells, madin-darby canine cells, hamster cells, xenopus cells and stem cells. An advantageous embodiment of the invention is the cell and cell lines being of mammalian origin. In a preferred embodiment, the cells are from a tissue sample. The tissue sample may be from a subject. The subject may have a disease. The subject may have cancer. The cells may be isolated from diseased tissue and normal tissue. The cells may be from a tumor sample. The cell lines may be tumor cell lines. In some embodiments, the cell is a plant cell. In other aspects, the cell is part of a plant tissue such as the vegetative parts of the plant, storage organs, fruit, flower and/or seed tissues. In further embodiments, the cell is an algae cell. In other embodiments, the cell is a fibroblast. In any of the embodiments, described herein, the cell may comprise a stem cell, for example an embryonic stem cell. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an induced pluripotent stem cell and/or combinations thereof. In certain embodiments, the stem cell is a human induced pluripotent stem cell (hiPSC) or a human embryonic stem cell (hESC). In any of the embodiments, described herein, the cell can comprise an embryo cell, for example one or more mouse, rat, rabbit or other mammal cell embryos.

Isolated chromatin fragments can be purified from cells using known methods in the art. Mononucleosomes can be generated based on established protocols (Ausio, J., and van Holde, K. E. (1986). Histone hyperacetylation: its effects on nucleosome conformation and stability. Biochemistry 25, 1421-1428.). In one embodiment, mononucleosomes may be purified by a gradient. The gradient may be sucrose or glycerol gradients. In a preferred embodiment, mononucleosomes are purified by glycerol gradient. Fractions from the gradient may be analyzed to determine fractions containing mononucleosomes, dinucleosomes, and oligonucleosomes. The methods of the present invention may utilize nucleosomes from any of these fractions. In one embodiment, the isolated chromatin fragment may include one, two, three, four, five, six, seven, eight, nine, ten, twenty, or up to a hundred nucleosomes. In preferred embodiments, mononucleosomes are used.

Mononucleosomes may be affinity purified using established protocols for immunoprecipitation. Affinity purification can be performed as described previously (Voigt et al. 2012 Cell Volume 151 Issue 1, 28 Sep. 2012, Pages 181-193).

Chromatin fragments can be prepared from cellular extracts by sonication or micrococcal nuclease (MNase) digestion as known in the art. Such preparations are starting materials for ChIP. In certain embodiments, methods for preparing fragmented chromatin for ChIP may be used.

Applicants and others have shown that 'barcoded' oligonucleotide adaptors can be ligated to chromatin fragments before ChIP to enable parallel processing of multiple low input samples (57-59). Applicants used an analogous barcoding strategy in microfluidics devices to acquire low-coverage chromatin profiles for single cells (60). In one embodiment, The present invention leverages chromatin barcoding to capture individual nucleosomes on a solid surface, decode their combinatorial modifications and sequence the associated DNA.

Chromatin fragments may also be prepared by inducing apoptosis in a cell. Apoptosis is a process of programmed cell death that occurs in multicellular organisms. Biochemical events lead to characteristic cell changes (morphology) and death. These changes include blebbing, cell shrinkage, nuclear fragmentation, chromatin condensation, chromosomal DNA fragmentation, global mRNA decay and activation of endogenous endonucleases. The calcium and magnesium dependent endonuclease activated in apoptosis cleaves the DNA double strand in the readily accessible linker regions between the nucleosomes into mononucleosomes and oligonucleosomes. Apoptosis produces cell fragments called apoptotic bodies that include fragmented DNA. It has been shown that nucleosomes are often packed into apoptotic bodies and phagocytosed by macrophages or neighboring cells. In situations of enhanced cell death, these mechanisms become overloaded, with the result that some nucleosomes are often released into circulation. Cell lines or cells obtained from a biological sample may be induced to undergo apoptosis and thus release chromatin fragments in apoptotic bodies. Not being bound by a theory, apoptotic bodies can be used as a source of fragmented nucleosomes without the need for digestion or sonication. Not being bound by a theory, nucleosomes retain their post-translational modifications during the apoptotic process and such modifications can be detected using antibodies specific for these modifications. For example, U.S. Patent Publication No. 2005/0069931 describes that nucleosomes from breast tumor cells that have undergone apoptosis retain their methyl, phosphorylation and acetyl modifications, and such modifications can be detected using antibodies raised against these specific modifications.

Nucleosomes can be detected in the serum of healthy individuals (Stroun et al., Annals of the New York Academy of Sciences 906:161-168 (2000)) as well as individuals afflicted with a disease state. Moreover, the serum concentration of nucleosomes is considerably higher in patients suffering from benign and malignant diseases, such as cancer and autoimmune disease (Holdenrieder et al (2001) Int J Cancer 95, 114-120; Trejo-Becerril et al (2003) Int J Cancer 104, 663-668; Kuroi et al 1999 Breast Cancer 6, 361-364; Kuroi et al (2001) Int j Oncology 19, 143-148; Amoura et al (1997) Arth Rheum 40, 2217-2225; Williams et al (2001) J Rheumatol 28, 81-94). Not being bound by a theory, the high concentration of nucleosomes in tumor bearing patients derives from apoptosis, which occurs spontaneously in proliferating tumors. The presence of elevated levels of nucleosomes in the blood of patients can serve as a diagnostic of diseases associated with enhanced cell death (Holdenrieder et al., Anticancer Res, 19 (4A): 2721-2724 (1999)). Nucleosomes circulating in the blood contain uniquely modified histones, wherein the unique histone epitope and/or the associated DNA can be correlated with a particular disease state. For example, U.S. Patent Publication No. 2005/0069931 (Mar. 31, 2005) relates to the use of antibodies directed against specific histone N-terminus modifications as diagnostic indicators of disease, employing such histone-specific antibodies to isolate nucleosomes from a blood or serum sample of a patient to facilitate purification and analysis of the accompanying DNA for diagnostic/screening purposes. Accordingly, the present invention may be used for the combinatorial single molecule analysis of cell-free mono or oligonucleosomes. The identification of modified histones and the associated DNA of single chromatin fragments can serve as diagnostic markers of disease and congenital defects. In another embodiment, the presence and/or percentage of bivalent nucleosomes can serve as diagnostic markers of disease and congenital defects.

Thus, in another embodiment, isolated chromatin fragments are derived from circulating chromatin, preferably circulating mono and oligonucleosomes. Isolated chromatin fragments may be derived from a biological sample. The biological sample may be from a subject or a patient in need thereof. The biological sample may be sera, plasma, lymph, blood, blood fractions, urine, synovial fluid, spinal fluid, saliva, circulating tumor cells or mucous. Not being bound by a theory, circulating chromatin and chromatin released from apoptotic cells are already fragmented to oligonucleosomes and mononucleosomes, thus not requiring digestion with a nuclease.

The present invention and any of the methods and embodiments described herein may be used for screening, diagnostics and the like. Screening may include, but is not limited to, prenatal screening. Reference is made to U.S. Pat. No. 9,128,086; U.S. patent publication Nos. 20050069931, 20070243549, 20100240054, 20120171225, 20140206014, International publication Nos. WO 2014131841, WO 2005019826, all incorporated by reference in their entirety. Prior to the present invention immunoprecipitation of bulk nucleosomes was performed and bulk DNA was sequenced. The methods allow no way to assign a histone modification to a specific nucleosome or DNA sequence. Additionally, bivalency of modifications cannot be determined. Further, immunoprecipitation results in non-specific binding and loss of a majority of the input sample. Not being bound by a theory, applying nucleosomes isolated from a biological sample to the single molecule systems described herein result in no loss of nucleosomes and histone modifications may be assigned to specific nucleosomes and sequences. This is especially advantageous when applying the present invention to prenatal screening where only a small fraction of nucleosomes may be fetal in origin.

It has been realized that there are fetal cells which are present in the mother's blood, and that these cells present a potential source of fetal chromosomes for prenatal DNA-based diagnostics. Currently available prenatal genetic tests usually involve invasive procedures. For example, chorionic villus sampling (CVS) performed on a pregnant woman around 10-12 weeks into the pregnancy and amniocentesis performed at around 14-16 weeks all contain invasive procedures to obtain the sample for testing chromosomal abnormalities in a fetus. Fetal cells obtained via these sampling procedures are usually tested for chromosomal abnormalities using cytogenetic or fluorescent in situ hybridization (FISH) analyses. Cell-free fetal DNA has been shown to exist in plasma and serum of pregnant women as early as the sixth week of gestation, with concentrations rising during pregnancy and peaking prior to parturition. Because these cells appear very early in the pregnancy, they could form the basis of an accurate, noninvasive, first trimester test. Not being bound by a theory, abundant amounts of maternal DNA is generally concomitantly recovered along with the fetal DNA of interest, thus decreasing sensitivity in fetal DNA quantification and mutation detection. The present invention overcomes such problems by identifying individual fetal nucleosomes. Fetal nucleosomes can be identified Prenatal diagnosis or prenatal screening (note that prenatal diagnosis and prenatal screening refer to two different types of tests) is testing for diseases or conditions in a fetus or embryo before it is born. The aim is to detect birth defects such as neural tube defects, Down syndrome, chromosome abnormalities, genetic disorders and other conditions, such as spina bifida, cleft palate, Tay Sachs disease, sickle cell anemia, thalassemia, cystic fibrosis, Muscular dystrophy, and fragile X syndrome. Screening can also be used for prenatal sex discernment. Common testing procedures include amniocentesis, ultrasonography including nuchal translucency ultrasound, serum marker testing, or genetic screening. In some cases, the tests are administered to determine if the fetus will be aborted, though physicians and patients also find it useful to diagnose high-risk pregnancies early so that delivery can be scheduled in a tertiary care hospital where the baby can receive appropriate care. Fetal DNA ranges from about 2-10% of the total DNA in maternal blood.

The H3 class of histones consists of four different protein types: the main types, H3.1 and H3.2; the replacement type, H3.3; and the testis specific variant, H3t. Although H3.1 and H3.2 are closely related, only differing at Ser96, H3.1 differs from H3.3 in at least 5 amino acid positions. Further, H3.1 is highly enriched in fetal liver, in comparison to its presence in adult tissues including liver, kidney and heart. In adult human tissue, the H3.3 variant is more abundant than the H3.1 variant, whereas the converse is true for fetal liver. The present invention may use these differences to detect fetal nucleosomes and fetal nucleic acid in a maternal biological sample that comprises both fetal and maternal cells and/or fetal nucleic acid. In preferred embodiments, nucleosomes are imaged with an antibody or binding ligand specific for H3.1 and H3.3.

In one embodiment, fetal nucleosomes may be obtained from blood. In other embodiments, fetal nucleosomes are obtained from a cervical mucus sample. In certain embodiments, a cervical mucus sample is obtained by swabbing or lavage from a pregnant woman early in the second trimester or late in the first trimester of pregnancy. The sample may be placed in an incubator to release DNA trapped in mucus. The incubator may be set at 37° C. The sample may be rocked for approximately 15 to 30 minutes. Mucus may be further dissolved with a mucinase for the purpose of releasing DNA. The sample may also be subjected to conditions, such as chemical treatment and the like, as well known in this art, to induce apoptosis to release fetal nucleosomes.

Histone variants, DNA modifications, and histone modifications in single nucleosomes may also be counted using the present invention, thus allowing modifications indicative of cancer or cancer progression to be quantitated. Importantly, sequencing allows the location of the nucleosomes to be determined. For example, U.S. patent publication 20140206014 describes that cancer samples had elevated nucleosome H2AZ, macroH2A1.1, 5-methylcytosine, P-H2AX(Ser139) levels as compared to healthy subjects. The presence of cancer cells in an individual may generate a higher level of cell free nucleosomes in the blood as a result of the increased apoptosis of the cancer cells. In one embodiment, an antibody directed against marks associated with apoptosis, such as H2B Ser 14(P), may be used to identify single nucleosomes that have been released from apoptotic neoplastic cells.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment the adapters are compatible with the methods described herein.

Single-cell ATAC-seq detects open chromatin in individual cells. ATAC-seq (assay for transposase-accessible chromatin) identifies regions of open chromatin using a hyperactive prokaryotic Tn5-transposase, which preferentially inserts into accessible chromatin and tags the sites with sequencing adaptors (Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128). The protocol is straightforward and robust and has become widely popular. Up to this point, ATAC-seq and other methods for the identification of open chromatin have required large pools of cells (Buenrostro, 2013; Thurman R E, Rynes E, Humbert R, Vierstra J, Maurano M T, Haugen E, et al. The accessible chromatin landscape of the human genome. Nature. 2012; 488:75-82), meaning that the data collected reflect cumulative accessibility across all cells in the pool. Independent studies have modified the ATAC-seq protocol for application to single cells (scATAC-seq) (Buenrostro J D, Wu B, Litzenburger U M, Ruff D, Gonzales M L, Snyder M P, et al. Single-cell chromatin accessibility reveals principles of regulatory variation. Nature. 2015; 523:486-90; and Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4). These studies provide data on hundreds (Buenrostro, 2015) or thousands (Cusanovich, 2015) of single cells in parallel. Both methods are limited in either the number of cells analyzed or the per-cell coverage.

In one embodiment, oligonucleotide sequences are ligated to isolated chromatin fragments. In preferred embodiments, the ligation is a blunt end ligation. In some embodiments, the ends of the DNA in the isolated chromatin fragments are made blunt. In some embodiments, the oligonucleotide sequences are phosphorylated. Not being bound by a theory, phosphorylation of the ends of an oligonucleotide sequence increases the efficiency of ligation. In one embodiment, the oligonucleotide sequence is linked to a binding molecule capable of binding to a capture molecule. The binding molecule may be linked to a single strand of the oligonucleotide sequence. In preferred embodiments, the binding molecule is linked to a single strand of the oligonucleotide sequence. In one embodiment, the binding molecule is a single stranded DNA sequence or a biotin molecule. In preferred embodiments, the binding molecule is biotin. In one embodiment, the oligonucleotide sequence has uracil incorporated into the strand of the oligonucleotide sequence not linked to the binding molecule. Not being bound by a theory, the strand linked to the binding molecule will remain bound to the capture molecule on the solid surface if the opposite strand is displaced during sequencing. Not being bound by a theory, the strand with uracil may be digested such that the uracil is removed and ssDNA is generated, whereby a sequencing primer can hybridize. Thus, the strand bound to the solid support can be sequenced.

Fluorescent dyes for use in fluorescent microscopy are known in the art. Exemplary dyes may be any available fluorescent dye (Table 1). In preferred embodiments, dyes are chosen with distinguishable emission spectra and that have excitation spectra compatible with the laser present on the microscope.

TABLE 1

| Sample Fluorescent Dyes | Excitation | Emission |
| --- | --- | --- |
| 1,8-ANS (1-Anilinonaphthalene-8-sulfonic acid) | 375 nm | 480 nm |
| 1-Anilinonaphthalene-8-sulfonic acid (1,8-ANS) | 375 nm | 479 nm |
| 5-(and-6)-Carboxy-2',7'-dichlorofluorescein pH 9.0 | 504 nm | 525 nm |
| 5-FAM pH 9.0 | 492 nm | 518 nm |
| 5-ROX (5-Carboxy-X-rhodamine, triethylammonium salt) | 578 nm | 604 nm |
| 5-ROX pH 7.0 | 578 nm | 604 nm |
| 5-TAMRA | 549 nm | 577 nm |
| 5-TAMRA pH 7.0 | 553 nm | 576 nm |
| 5-TAMRA-MeOH | 543 nm | 567 nm |
| 6 JOE | 520 nm | 548 nm |
| 6,8-Difluoro-7-hydroxy-4-methylcoumarin pH 9.0 | 358 nm | 450 nm |
| 6-Carboxyrhodamine 6G pH 7.0 | 526 nm | 547 nm |
| 6-Carboxyrhodamine 6G, hydrochloride | 525 nm | 547 nm |
| 6-HEX, SE pH 9.0 | 520 nm | 548 nm |
| 6-TET, SE pH 9.0 | 521 nm | 542 nm |
| 7-Amino-4-methylcoumarin pH 7.0 | 346 nm | 442 nm |
| 7-Hydroxy-4-methylcoumarin | 360 nm | 447 nm |
| 7-Hydroxy-4-methylcoumarin pH 9.0 | 361 nm | 448 nm |
| Acridine Orange | 431 nm | 520 nm |
| Alexa 350 | 343 nm | 441 nm |
| Alexa 405 | 401 nm | 421 nm |
| Alexa 430 | 431 nm | 540 nm |
| Alexa 488 | 493 nm | 520 nm |
| Alexa 532 | 528 nm | 553 nm |
| Alexa 546 | 562 nm | 573 nm |
| Alexa 555 | 553 nm | 568 nm |
| Alexa 568 | 576 nm | 603 nm |
| Alexa 594 | 590 nm | 619 nm |
| Alexa 633 | 632 nm | 648 nm |
| Alexa 647 | 653 nm | 669 nm |
| Alexa 660 | 664 nm | 691 nm |
| Alexa 680 | 679 nm | 703 nm |
| Alexa 700 | 696 nm | 720 nm |
| Alexa Fluor 430 antibody conjugate pH 7.2 | 431 nm | 540 nm |
| Alexa Fluor 488 antibody conjugate pH 8.0 | 499 nm | 520 nm |
| Alexa Fluor 488 hydrazide-water | 493 nm | 518 nm |
| Alexa Fluor 532 antibody conjugate pH 7.2 | 528 nm | 553 nm |
| Alexa Fluor 555 antibody conjugate pH 7.2 | 553 nm | 568 nm |
| Alexa Fluor 568 antibody conjugate pH 7.2 | 579 nm | 603 nm |
| Alexa Fluor 610 R-phycoerythrin streptavidin pH 7.2 | 567 nm | 627 nm |
| Alexa Fluor 633 antibody conjugate pH 7.2 | 631 nm | 648 nm |
| Alexa Fluor 647 antibody conjugate pH 7.2 | 653 nm | 668 nm |
| Alexa Fluor 647 R-phycoerythrin streptavidin pH 7.2 | 569 nm | 666 nm |
| Alexa Fluor 660 antibody conjugate pH 7.2 | 663 nm | 691 nm |
| Alexa Fluor 680 antibody conjugate pH 7.2 | 679 nm | 702 nm |
| Alexa Fluor 700 antibody conjugate pH 7.2 | 696 nm | 719 nm |
| Allophycocyanin pH 7.5 | 651 nm | 660 nm |
| AMCA conjugate | 347 nm | 444 nm |
| Amino Coumarin | 345 nm | 442 nm |
| APC (allophycocyanin) | 650 nm | 660 nm |
| Atto 647 | 644 nm | 670 nm |
| Auramine O | 431 nm | 501 nm |
| BCECF pH 5.5 | 485 nm | 521 nm |
| BCECF pH 9.0 | 501 nm | 527 nm |
| BFP (Blue Fluorescent Protein) | 380 nm | 439 nm |
| BO-PRO-1-DNA | 462 nm | 482 nm |
| BO-PRO-3-DNA | 574 nm | 604 nm |
| BOBO-1-DNA | 461 nm | 484 nm |
| BOBO-3-DNA | 570 nm | 605 nm |
| BODIPY 650/665-X, MeOH | 646 nm | 664 nm |
| BODIPY FL conjugate | 503 nm | 512 nm |
| BODIPY FL, MeOH | 502 nm | 511 nm |
| Bodipy R6G SE | 528 nm | 547 nm |
| BODIPY R6G, MeOH | 528 nm | 547 nm |
| BODIPY TMR-X antibody conjugate pH 7.2 | 544 nm | 573 nm |
| Bodipy TMR-X conjugate | 544 nm | 573 nm |
| BODIPY TMR-X, MeOH | 544 nm | 570 nm |
| BODIPY TMR-X, SE | 544 nm | 570 nm |
| BODIPY TR-X phallacidin pH 7.0 | 590 nm | 621 nm |
| BODIPY TR-X, MeOH | 588 nm | 621 nm |
| BODIPY TR-X, SE | 588 nm | 621 nm |
| BOPRO-1 | 462 nm | 482 nm |
| BOPRO-3 | 574 nm | 604 nm |
| Calcein | 493 nm | 514 nm |
| Calcein pH 9.0 | 494 nm | 514 nm |
| Calcium Crimson | 589 nm | 608 nm |
| Calcium Crimson Ca2+ | 590 nm | 608 nm |
| Calcium Green | 506 nm | 530 nm |
| Calcium Green-1 Ca2+ | 506 nm | 529 nm |
| Calcium Orange | 549 nm | 574 nm |
| Calcium Orange Ca2+ | 549 nm | 573 nm |
| Carboxynaphthofluorescein pH 10.0 | 600 nm | 674 nm |
| Cascade Blue | 398 nm | 420 nm |
| Cascade Blue BSA pH 7.0 | 401 nm | 419 nm |
| Cascade Yellow | 399 nm | 549 nm |
| Cascade Yellow antibody conjugate pH 8.0 | 399 nm | 549 nm |
| CFDA | 495 nm | 517 nm |
| CFP (Cyan Fluorescent Protein) | 434 nm | 474 nm |
| Cl-NERF pH 2.5 | 504 nm | 541 nm |
| Cl-NERF pH 6.0 | 513 nm | 538 nm |
| Citrine | 515 nm | 530 nm |

TABLE 1-continued

| Sample Fluorescent Dyes | Excitation | Emission |
|---|---|---|
| Coumarin | 360 nm | 447 nm |
| Cy 2 | 489 nm | 503 nm |
| Cy 3 | 549 nm | 562 nm |
| Cy 3.5 | 578 nm | 591 nm |
| Cy 5 | 646 nm | 664 nm |
| Cy 5.5 | 673 nm | 692 nm |
| CyQUANT GR-DNA | 502 nm | 523 nm |
| Dansyl Cadaverine | 335 nm | 524 nm |
| Dansyl Cadaverine, MeOH | 335 nm | 526 nm |
| DAPI | 358 nm | 463 nm |
| DAPI-DNA | 359 nm | 461 nm |
| Dapoxyl (2-aminoethyl) sulfonamide | 372 nm | 582 nm |
| DDAO pH 9.0 | 648 nm | 657 nm |
| Di-8 ANEPPS | 469 nm | 630 nm |
| Di-8-ANEPPS-lipid | 469 nm | 631 nm |
| DiI | 551 nm | 565 nm |
| DiO | 487 nm | 501 nm |
| DM-NERF pH 4.0 | 493 nm | 530 nm |
| DM-NERF pH 7.0 | 509 nm | 537 nm |
| DsRed | 563 nm | 581 nm |
| DTAF | 495 nm | 517 nm |
| dTomato | 554 nm | 581 nm |
| DyLight 350 | 332 nm | 435 nm |
| DyLight 405 | 399 nm | 434 nm |
| DyLight 488 | 493 nm | 518 nm |
| DyLight 549 | 555 nm | 569 nm |
| DyLight 594 | 592 nm | 616 nm |
| DyLight 633 | 624 nm | 646 nm |
| DyLight 649 | 652 nm | 668 nm |
| DyLight 680 | 678 nm | 706 nm |
| eCFP (Enhanced Cyan Fluorescent Protein) | 437 nm | 476 nm |
| eGFP (Enhanced Green Fluorescent Protein) | 488 nm | 509 nm |
| Eosin | 524 nm | 546 nm |
| Eosin antibody conjugate pH 8.0 | 525 nm | 546 nm |
| Erythrosin-5-isothiocyanate pH 9.0 | 533 nm | 554 nm |
| Ethidium Bromide | 524 nm | 605 nm |
| Ethidium homodimer | 528 nm | 617 nm |
| Ethidium homodimer-1-DNA | 528 nm | 617 nm |
| evoglow-Bs1 | 448 nm | 496 nm |
| evoglow-Bs2 | 448 nm | 496 nm |
| evoglow-Pp1 | 448 nm | 495 nm |
| eYFP (Enhanced Yellow Fluorescent Protein) | 514 nm | 526 nm |
| FDA | 495 nm | 517 nm |
| FITC | 495 nm | 517 nm |
| FITC antibody conjugate pH 8.0 | 495 nm | 519 nm |
| FlAsH | 509 nm | 529 nm |
| Fluo-3 | 506 nm | 527 nm |
| Fluo-3 Ca2+ | 506 nm | 527 nm |
| Fluo-4 | 494 nm | 516 nm |
| Fluor-Ruby | 554 nm | 582 nm |
| Fluorescein | 495 nm | 517 nm |
| Fluorescein 0.1M NaOH | 493 nm | 513 nm |
| Fluorescein antibody conjugate pH 8.0 | 493 nm | 517 nm |
| Fluorescein dextran pH 8.0 | 501 nm | 524 nm |
| Fluorescein pH 9.0 | 490 nm | 514 nm |
| Fluoro-Emerald | 495 nm | 524 nm |
| FM 1-43 | 472 nm | 578 nm |
| FM 1-43 lipid | 473 nm | 579 nm |
| FM 4-64 | 508 nm | 751 nm |
| FM 4-64, 2% CHAPS | 506 nm | 751 nm |
| Fura Red Ca2+ | 435 nm | 670 nm |
| Fura Red, high Ca | 434 nm | 659 nm |
| Fura Red, low Ca | 472 nm | 673 nm |
| Fura-2 Ca2+ | 336 nm | 505 nm |
| Fura-2, high Ca | 336 nm | 504 nm |
| Fura-2, no Ca | 367 nm | 515 nm |
| GFP (S65T) | 489 nm | 509 nm |
| HcRed | 590 nm | 614 nm |
| Hoechst 33258 | 352 nm | 455 nm |
| Hoechst 33258-DNA | 352 nm | 455 nm |
| Hoechst 33342 | 352 nm | 455 nm |
| Indo-1 Ca2+ | 346 nm | 404 nm |
| Indo-1, Ca free | 346 nm | 479 nm |
| Indo-1, Ca saturated | 331 nm | 404 nm |
| JC-1 | 592 nm | 595 nm |
| JC-1 pH 8.2 | 593 nm | 595 nm |
| Lissamine rhodamine | 572 nm | 590 nm |
| LOLO-1-DNA | 568 nm | 580 nm |
| Lucifer Yellow, CH | 428 nm | 542 nm |
| LysoSensor Blue | 374 nm | 424 nm |
| LysoSensor Blue pH 5.0 | 374 nm | 424 nm |
| LysoSensor Green | 447 nm | 504 nm |
| LysoSensor Green pH 5.0 | 447 nm | 502 nm |
| LysoSensor Yellow pH 3.0 | 389 nm | 542 nm |
| LysoSensor Yellow pH 9.0 | 335 nm | 530 nm |
| LysoTracker Blue | 373 nm | 421 nm |
| LysoTracker Green | 503 nm | 509 nm |
| LysoTracker Red | 578 nm | 589 nm |
| Magnesium Green | 507 nm | 530 nm |
| Magnesium Green Mg2+ | 507 nm | 531 nm |
| Magnesium Orange | 550 nm | 575 nm |
| Marina Blue | 362 nm | 464 nm |
| mBanana | 540 nm | 553 nm |
| mCherry | 587 nm | 610 nm |
| mHoneydew | 478 nm | 562 nm |
| MitoTracker Green | 490 nm | 512 nm |
| MitoTracker Green FM, MeOH | 490 nm | 512 nm |
| MitoTracker Orange | 551 nm | 575 nm |
| MitoTracker Orange, MeOH | 551 nm | 575 nm |
| MitoTracker Red | 578 nm | 599 nm |
| MitoTracker Red, MeOH | 578 nm | 599 nm |
| mNeonGreen | 506 nm | 517 nm |
| mOrange | 548 nm | 562 nm |
| mPlum | 587 nm | 649 nm |
| mRFP | 585 nm | 608 nm |
| mStrawberry | 575 nm | 596 nm |
| mTangerine | 568 nm | 585 nm |
| NBD-X | 466 nm | 534 nm |
| NBD-X, MeOH | 467 nm | 538 nm |
| NeuroTrace 500/525, green fluorescent Nissl stain-RNA | 497 nm | 524 nm |
| Nile Blue, EtOH | 631 nm | 660 nm |
| Nile Red | 559 nm | 637 nm |
| Nile Red-lipid | 553 nm | 636 nm |
| Nissl | 497 nm | 524 nm |
| Oregon Green 488 | 498 nm | 526 nm |
| Oregon Green 488 antibody conjugate pH 8.0 | 498 nm | 526 nm |
| Oregon Green 514 | 512 nm | 532 nm |
| Oregon Green 514 antibody conjugate pH 8.0 | 513 nm | 533 nm |
| Pacific Blue | 404 nm | 455 nm |
| Pacific Blue antibody conjugate pH 8.0 | 404 nm | 455 nm |
| Phycoerythrin | 565 nm | 575 nm |
| PicoGreen dsDNA quantitation reagent | 502 nm | 522 nm |
| PO-PRO-1 | 434 nm | 457 nm |
| PO-PRO-1-DNA | 435 nm | 457 nm |
| PO-PRO-3 | 539 nm | 571 nm |
| PO-PRO-3-DNA | 539 nm | 571 nm |
| POPO-1 | 433 nm | 457 nm |
| POPO-1-DNA | 433 nm | 458 nm |
| POPO-3 | 533 nm | 573 nm |
| Propidium Iodide | 538 nm | 617 nm |
| Propidium Iodide-DNA | 538 nm | 619 nm |
| Quasar 570 | 549 nm | 562 nm |
| R-Phycoerythrin pH 7.5 | 565 nm | 576 nm |
| ReAsH | 597 nm | 608 nm |
| Resorufin | 571 nm | 584 nm |
| Resorufin pH 9.0 | 571 nm | 584 nm |
| Rhod-2 | 552 nm | 577 nm |
| Rhod-2 Ca2+ | 553 nm | 578 nm |
| Rhodamine | 551 nm | 573 nm |
| Rhodamine 110 | 497 nm | 520 nm |
| Rhodamine 110 pH 7.0 | 497 nm | 520 nm |
| Rhodamine 123, MeOH | 507 nm | 529 nm |
| Rhodamine B | 543 nm | 565 nm |
| Rhodamine Green | 497 nm | 524 nm |
| Rhodamine phalloidin pH 7.0 | 558 nm | 575 nm |

TABLE 1-continued

| Sample Fluorescent Dyes | Excitation | Emission |
|---|---|---|
| Rhodamine Red-X antibody conjugate pH 8.0 | 573 nm | 591 nm |
| Rhodaminen Green pH 7.0 | 497 nm | 523 nm |
| Rhodol Green antibody conjugate pH 8.0 | 499 nm | 524 nm |
| Sapphire | 396 nm | 511 nm |
| SBFI-Na+ | 336 nm | 527 nm |
| Sodium Green Na+ | 507 nm | 531 nm |
| Sulforhodamine 101, EtOH | 578 nm | 593 nm |
| SYBR Green I | 498 nm | 522 nm |
| SYPRO Ruby | 467 nm | 618 nm |
| SYTO 13-DNA | 488 nm | 506 nm |
| SYTO 17-DNA | 619 nm | 638 nm |
| SYTO 45-DNA | 451 nm | 486 nm |
| SYTOX Blue-DNA | 445 nm | 470 nm |
| Tetramethylrhodamine antibody conjugate pH 8.0 | 552 nm | 578 nm |
| Tetramethylrhodamine dextran pH 7.0 | 555 nm | 582 nm |
| Texas Red-X antibody conjugate pH 7.2 | 596 nm | 613 nm |
| TO-PRO-1-DNA | 515 nm | 531 nm |
| TO-PRO-3-DNA | 642 nm | 657 nm |
| TOTO-1-DNA | 514 nm | 531 nm |
| TOTO-3-DNA | 642 nm | 661 nm |
| TRITC | 550 nm | 573 nm |
| X-Rhod-1 Ca2+ | 580 nm | 602 nm |
| YO-PRO-1-DNA | 491 nm | 507 nm |
| YO-PRO-3-DNA | 613 nm | 629 nm |
| YOYO-1-DNA | 491 nm | 509 nm |
| YOYO-3-DNA | 612 nm | 631 nm |

In preferred embodiments the dyes are selected from Alexa 488, Alexa 555, Alexa 640, CY3, CY5, an Atto Dyes, and a Pacific Dye.

Fluorescent microscopy may be used to visualize the single isolated chromatin fragments of the present invention. Not being bound by a theory fluorescent microscopy would produce background from unbound labeling ligands present in solution, but the fluorescence signal of bound isolated chromatin fragments may be distinguishable. In a preferred embodiment TIRF microscopy is used. TIRF microscopy enables a selective visualization of surface regions, thus background may be eliminated. TIRF microscopy may utilize one laser, two lasers, three lasers or four lasers. Simultaneous multicolor detection of 2-4 dyes may be performed. The dyes may be excited by a single laser and emit a different wavelength. The dyes may have different fluorescent lifetimes. The dyes may be excited by different lasers and emit different wavelengths. Dyes and lasers applicable to TIRF microscopy are known in the art. The microscope may be set up in any configuration as described by Harris et al. in PCT publication WO2006055521, TIRF single molecule analysis and method of sequencing nucleic acids. Additional methods for imaging single molecules are described by Friedman L J, Chung J, and Gelles J. (Viewing dynamic assembly of molecular complexes by multi-wavelength single-molecule fluorescence. Biophys J. 2006 Aug. 1; 91(3):1023-31. Epub 2006 May 12) and in PCT publication number WO2006133221, Apparatus and method for introducing multiwavelength laser excitation in fluorescence microscopy, incorporated herein by reference.

TIRF microscopy enables detection of molecules or events that occur close to a solid surface, where an evanescent wave excites fluorophores. It provides a powerful means for detecting single fluorescent molecules that are within ~100 nm of a surface and separated from each other by the diffraction limit (~200 nm). TIRF microscopy has been used to investigate cellular and molecular structures18 and protein dynamics (62), and to quantify proteins at single-molecule resolution (63). In preferred embodiments, the present invention leverages TIRF microscopy to decode combinatorial modification states of hundreds of millions of nucleosomes captured on solid surface.

A variant of TIRF microscopy has been used for single-molecule DNA sequencing (Helicos) (44,64). Millions of single-stranded DNAs are attached to a surface in a spatially distributed manner. Their sequences are read by successive incorporation and imaging of fluorescent nucleotides with reversible terminators. An alternative single-molecule strategy has been established for long read sequencing (Pacific BioSciences) (65).

Sequencing of DNA present in isolated chromatin fragments may use any method known in the art. In one embodiment, the sequencing is performed on a solid surface bound by the isolated chromatin fragments. Sequencing of single molecules on a solid surface may utilize sequencing by synthesis as previously described (Harris, T. D., et al., *Single-molecule DNA sequencing of a viral genome*. Science, 2008. 320(5872):p. 106-9). The sequencing by synthesis may utilize the TIRF microscope used to image binding of labeling ligand to the isolated chromatin fragments. With respect to general information on sequencing by synthesis systems, methods and components thereof, all useful in the practice of the instant invention, reference is made to: U.S. Pat. Nos. 7,282,337; 7,279,563; 7,220,549; 7,169,560; 6,818,395; and 6,911,345; and US Pub. Nos. 2006/0252077; 2007/0070349; 2009/0249949; and 2010/0190168, herein incorporated by reference in their entirety.

Single molecule sequencing of RNA may be performed by any method known in the art. Reference is made to Lipson et al., Quantification of the yeast transcriptome by single-molecule sequencing (Nat Biotechnol. 2009 July; 27(7):652-8), herein incorporated by reference in their entirety. Shown is single-molecule sequencing digital gene expression (smsDGE), a high-throughput, amplification-free method for accurate quantification of the full range of cellular polyadenylated RNA transcripts using a Helicos Genetic Analysis system.

Sequencing by synthesis requires a primer binding site and single stranded DNA. In one embodiment, the oligonucleotide sequence ligated to the isolated chromatin fragment contains uracil. The uracil may be digested with a nuclease specific for removing uracil from a DNA strand. The nuclease may be an uracil excision reagent. The uracil excision reagent may include a mixture of uracil DNA glycosylase (UDG) and the DNA glycosylase-lyase Endonuclease VIII. The uracil excision reagent may be the USER enzyme reagent (New England Biolabs, Ipswich, Mass.). Not being bound by a theory, digestion of an oligonucleotide sequence containing uracil on one strand with a nuclease specific for uracil will generate single stranded DNA on the opposite strand. The single stranded DNA may then be hybridized to a sequencing primer. The sequencing primer allows extension and sequencing of the oligonucleotide sequence and DNA from the isolated chromatin fragment by strand displacement caused by the extending polymerase. The USER (Uracil-Specific Excision Reagent) Enzyme generates a single nucleotide gap at the location of a uracil. USER Enzyme is a mixture of uracil DNA glycosylase (UDG) and the DNA glycosylase-lyase Endonuclease VIII. UDG catalyses the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. In another embodiment, ssDNA for hybridization of a sequencing primer is obtained by addition of formamide.

In one embodiment, protein bound RNA's or RNA/Protein complexes are sequenced. Not being bound by a theory, the RNA may be sequenced using a reverse transcriptase instead of a DNA polymerase. Sequencing by reverse transcriptase generates cDNA and can use the same labeled nucleotides as sequencing a DNA template. In one embodiment, RNA protein complexes are analyzed by ligation of an oligonucleotide sequence as described herein to the RNA. The RNA may bind to a solid surface. The proteins may be imaged using labeling ligands specific for a target molecule.

In one embodiment, RNA/Protein complexes can be isolated from exosomes. In another embodiment RNA/Protein complexes and chromatin can be isolated from circulating tumor cells (CTC).

Isolation of circulating tumor cells (CTC) for use in any of the methods described herein may be performed. Exemplary technologies that achieve specific and sensitive detection and capture of CTCs may be used in the present invention have been described (Mostert B, et al., Circulating tumor cells (CTCs): detection methods and their clinical relevance in breast cancer. Cancer Treat Rev. 2009; 35:463-474; and Talasaz A H, et al., Isolating highly enriched populations of circulating epithelial cells and other rare cells from blood using a magnetic sweeper device. Proc Natl Acad Sci USA. 2009; 106:3970-3975). As few as one CTC may be found in the background of 105-106 peripheral blood mononuclear cells (Ross A A, et al., Detection and viability of tumor cells in peripheral blood stem cell collections from breast cancer patients using immunocytochemical and clonogenic assay techniques. Blood. 1993; 82:2605-2610). The CellSearch® platform uses immunomagnetic beads coated with antibodies to Epithelial Cell Adhesion Molecule (EpCAM) to enrich for EPCAM-expressing epithelial cells, followed by immunostaining to confirm the presence of cytokeratin staining and absence of the leukocyte marker CD45 to confirm that captured cells are epithelial tumor cells (Momburg F, et al., Immunohistochemical study of the expression of a Mr 34,000 human epithelium-specific surface glycoprotein in normal and malignant tissues. Cancer Res. 1987; 47:2883-2891; and Allard W J, et al., Tumor cells circulate in the peripheral blood of all major carcinomas but not in healthy subjects or patients with nonmalignant diseases. Clin Cancer Res. 2004; 10:6897-6904). The number of cells captured in this assay has been prospectively demonstrated to have prognostic significance for breast, colorectal and prostate cancer patients with advanced disease Cohen S J, et al., J Clin Oncol. 2008; 26:3213-3221; Cristofanilli M, et al. N Engl J Med. 2004; 351:781-791; Cristofanilli M, et al., J Clin Oncol. 2005; 23:1420-1430; and de Bono J S, et al. Clin Cancer Res. 2008; 14:6302-6309).

The present invention also provides for isolating CTCs with CTC-Chip Technology. CTC-Chip is a microfluidic based CTC capture device where blood flows through a chamber containing thousands of microposts coated with anti-EpCAM antibodies to which the CTCs bind (Nagrath S, et al. Isolation of rare circulating tumour cells in cancer patients by microchip technology. Nature. 2007; 450:1235-1239). CTC-Chip provides a significant increase in CTC counts and purity in comparison to the CellSearch® system (Maheswaran S, et al. Detection of mutations in EGFR in circulating lung-cancer cells. N Engl J Med. 2008; 359:366-377). Both platforms may be used for downstream molecular analysis. Examples include immunofluorescence for IGF-1R and the DNA damage response marker, gH2AX, in Phase I studies (de Bono J S, et al. Clin Cancer Res. 2007; 13:3611-3616; Wang L H, et al. Clin Cancer Res. 16:1073-1084), EGFR (Smith G D, et al. J Clin Pathol. 2008; 61:487-493) and HER2 (Pestrin M, et al. Breast Cancer Res Treat. 2009; 118:523-530) status in breast cancer, FISH for PTEN and FISH and RNA for TMPRSS2-ERG fusion in prostate cancer (Attard G, et al. Cancer Res. 2009; 69:2912-2918; (Stott S L, et al. Sci Transl Med. 2:25ra23), and genotyping for EGFR mutations in lung cancer (Maheswaran S, et al. N Engl J Med. 2008; 359:366-377).

Not being bound by a theory, labeling ligands associate and dissociate from their target molecules during incubation with the isolated chromatin fragments (See e.g., FIG. 7). Unexpectedly, methods requiring only a single image at a single time point of isolated chromatin fragments would be unable to determine the presence of a target molecule present on each isolated chromatin fragment. In one embodiment, determination of the presence of a target molecule requires imaging over time. Not being bound by a theory, different labeling ligands have different dissociation constants for binding a target molecule. The length of binding and imaging may be determined based on the labeling ligand. The labeling ligands may be imaged at more than one time point, at least two, three, four, five, ten, twenty, or a hundred time points. The time points may be every second, minute, 10 minutes, 15 minutes, 30 minutes, or hour. The total imaging time may be 10 minutes, 1 hour, 2 hours, 3 hours, 4 hours, 10 hours, or 24 hours. In a preferred embodiment, the imaging may include 8-10 images over 3 hours. In another preferred embodiment, the imaging may include 2-3 images over 10 minutes.

The isolated chromatin fragments are bound by labeling ligands and imaged simultaneously at multiple time points in an imaging buffer that is formulated such that it allows binding of antibodies as well as allowing imaging. Not being bound by a theory, the specific binding of antibodies in the imaging buffer is the most important parameter. Not being bound by a theory, antibodies have different specificities and binding strength. In one embodiment, the buffer is optimized such that a labeling ligand binds specifically to a target molecule and not to a non-specific site.

Not being bound by a theory, antibodies generated against modified histones have the strongest affinity for the modified histone, but may also have a lesser affinity for an unmodified histone. Not being bound by a theory, the imaging buffer may be formulated to completely prevent non-specific binding. In a preferred embodiment, the imaging buffer is optimized for each labeling ligand. In one embodiment, the imaging buffer is formulated such that the binding affinity of the labeling ligand is decreased in order to increase specificity of the binding. In a preferred embodiment, the imaging buffer is formulated such that most antibodies will bind to their target molecules with high specificity and low non-specific binding. Not being bound by a theory, antibody optimization is more important in single molecule experiments than in experiments performed with a plurality of molecules. Optimization of antibodies can be performed by using control nucleosomes with known modifications. The control nucleosomes may be recombinant nucleosomes assembled by incubating core histones expressed in bacteria with a DNA template as shown previously (R. Margueron, et al., Role of the polycomb protein EED in the propagation of repressive histone marks. Nature, 461 (2009), pp. 762-767). The control nucleosomes may be used with the present invention. Conditions may be optimized to remove all non-specific binding by performing the method of the present invention with control nucleosomes. Conditions for immunoprecipitation of mononucleosomes may be used for optimization of the imaging buffer. Without limiting additional conditions, an exemplary immunoprecipitation buffer comprises 50 mM HEPES [pH 7.9], 50 mM NaCl, 50 mM KCl, 5 mM EDTA, 0.5% NP-40, 0.1% N-lauroyl sarcosine, and 5 mM sodium butyrate (Margueron, et al., 2009).

Applicants unexpectedly determined that a small change in pH prevented binding of modified histone antibodies in the imaging buffer. In preferred embodiments, the pH is 6.5. and the buffer includes MES. In a preferred embodiment the imaging buffer contains 10 mM MES (pH 6.5), 60 mM KCl, 0.32 mM EDTA, 3 mM MgCl2, 10% glycerol, 0.02% Igepal (Sigma Aldrich), and 0.1 mg/ml BSA. In another preferred embodiment, the KCl concentration may be adjusted to be any concentration within the range of 50 mM to 500 mM. In another preferred embodiment, the KCl is replaced with ammonium sulfate in the range of 25 mM to 250 mM. In another embodiment, the imaging buffer does contain $MgCl_2$.

Because cell lysates also contain proteases and phosphatases that can modify or degrade the target proteins, isolation of chromatin fragments can be performed at 4° C. and may include proteasomal inhibitors, such as PMSF, aprotinin and leupeptin, along with sodium orthovanadate or sodium fluoride as a phosphatase inhibitor. While these components can be added individually, commercial inhibitor cocktails are available that are higher quality and easier to use.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814, 263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 Jun. 10, 2014; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835, 973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055, 484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096, 324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9

(dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In a preferred embodiment, single molecule analysis is performed using microfluidics. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No. WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single molecule analysis is performed in droplets using methods according to WO 2014085802.

Each of these patents and publications is herein incorporated by reference in their entireties for all purposes.

Single cells can be separated using microfluidic devices. Microfluidics involves micro-scale devices that handle small volumes of fluids. Because microfluidics may accurately and reproducibly control and dispense small fluid volumes, in particular volumes less than 1 application of microfluidics provides significant cost-savings. The use of microfluidics technology reduces cycle times, shortens time-to-results, and increases throughput. The small volume of microfluidics technology improves amplification and construction of DNA libraries made from single cells and single isolated aggregations of cellular constituents. Furthermore, incorporation of microfluidics technology enhances system integration and automation.

Single cells of the present invention may be divided into single droplets using a microfluidic device. The single cells in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201, all the contents and disclosure of each of which are herein incorporated by reference in their entirety.

The term "barcode" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA or CAGGAGCC. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

In another aspect, the methods of the present invention are used to screen chemical compounds that affect the isolated chromatin fragments. The chemical compounds may be a biological compound. The chemical compounds may target a histone modifying enzyme. The chemical compounds may be used as a therapeutic composition to treat a patient in need thereof. The methods may also be used to study gene function in relation to chromatin modifications. Genes may be over-expressed, knocked down, or knocked out in a population of cells followed by the combinatorial analysis of chromatin modifications. Genes may be manipulated by any methods known in the art. Exemplary methods include over-expression vectors, RNAi, and CRISPR-Cas9 systems. Not being bound by a theory, the alteration of expression of a gene may affect the combinatorial modifications on chromatin.

In another aspect, the present invention provides a device for automation of the methods described herein. The device provides for a flow cell, wherein reagents are flowed in and out. The device also provides for automated imaging and analysis. The device may also incorporate reagents for sequencing as well as target molecule detection. The device may also include the microscope required for imaging. The device may also include memory for storing coordinates of bound protein nucleic acid complexes, images, and sequencing data. The device may also include software for integrating sequencing and protein target data.

The present invention advantageously leverages high-sensitivity optical technology that enables for the first time the detection of single molecules on a surface of a flow cell by Total Internal Reflection Fluorescence (TIRF) Microscopy. The present invention advantageously uses the novel discovery that multiple images are required to determine protein modifications on single molecules. The present invention may be applied to any single molecule protein/protein interactions, protein-RNA interactions, or RNA-DNA interactions, as well as post translational modifications on single molecules. The methods of the present invention allow for the first time the ability to image multiple modifications on any single molecule bound to a solid surface.

The method advantageously allows extracted nucleosomes from cells to be attached to a surface, followed by detection of each labeled single nucleosome.

The method advantageously allows the characterization of the combinatorial pattern of histone modifications on a single nucleosome particle by incubation with fluorescently-labeled antibodies that target these modifications.

The method advantageously allows direct on-surface single-molecule DNA sequencing to identify the DNA molecules associated with the modified nucleosomes.

The method also advantageously provides a novel technique that enables direct visualization of the pattern of histone modifications on a single nucleosome in a specific locus providing significant utility in the study of epigenetics. The novel methods enables the study of the dynamics and roles of histone modifications, as well as the regulatory principles that dictate the epigenetic landscape in different genomic regions. The present invention provides novel methods to study the "histone code" on single nucleosomes in specific genomic regions and can be applied to studies of epigenetics in development and disease.

The present invention has significant advantages over ChIP-seq. While ChIP-seq provides only relative data (i.e. one region of the genome contains more of a certain mark in comparison with another region), data obtained with the single-nucleosome imaging method of the present invention allows counting of the modified nucleosomes, and calculation of the absolute percentage of nucleosomes which carry each of the marks (or a combination of different marks). The single-molecule analysis of the present invention allows for the first time the ability to model variability in population behavior and ultimately to understand the regulatory principles.

The present invention advantageously provides single-molecule systems and methods that enable investigators to study inter-relationships among chromatin modifications and transcription factors, and to map combinatorial chromatin states with single-molecule precision. The underlying technologies are highly innovative, and can offer a new standard for functional genomics, opening new research directions at the interface of genomics and proteomics.

The large numbers of histone modifications and transcription factors that interact with our genome has fueled speculation that multiple elements act combinatorially to direct specific outcomes (56). While there is evidence for combinatorial function, many elements act redundantly (66,67). Regardless, the field lacks any robust means for direct detection and analysis of such combinations. The systems and methods of the present invention advantageously provide a unique opportunity to systematically examine how chromatin modifications and transcription factors interact combinatorially to organize and control genomic regulatory elements.

Existing tools for mapping chromatin and transcription factors rely on ChIP and, consequently, yield analog maps that estimate relative modification levels or occupancies. In contrast, the systems and methods of the present invention advantageously provide direct counting of single-molecules in a population, and thus yield digital maps amenable for absolute quantification and comparisons between samples.

(3) Experimental systems at the genome-proteome interface. Single-molecule TIRF provides a powerful means for investigating macromolecular complexes. The systems and methods of the present invention advantageously provide for detection and analysis of very large numbers of complexes ($\sim 10^8$), which can provide insight into their stability and variability. The systems and methods are especially valuable for studying complexes between proteins, DNAs and RNAs, which are increasingly appreciated to play key roles in regulating gene activity and cell phenotype.

Finally, Applicants established robust systems for investigating combinatorial chromatin and transcription factor interactions with single-molecule precision and genome-wide coverage. Implementation and dissemination of these novel systems yield a transformative new tool for functional genomics, and enable researchers to investigate chromatin structure, transcription factor interactions and functional genomic elements with extraordinary precision.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Characterization of the Combinatorial Pattern of Histone Modifications on a Single Nucleosome.

Figure 6A:
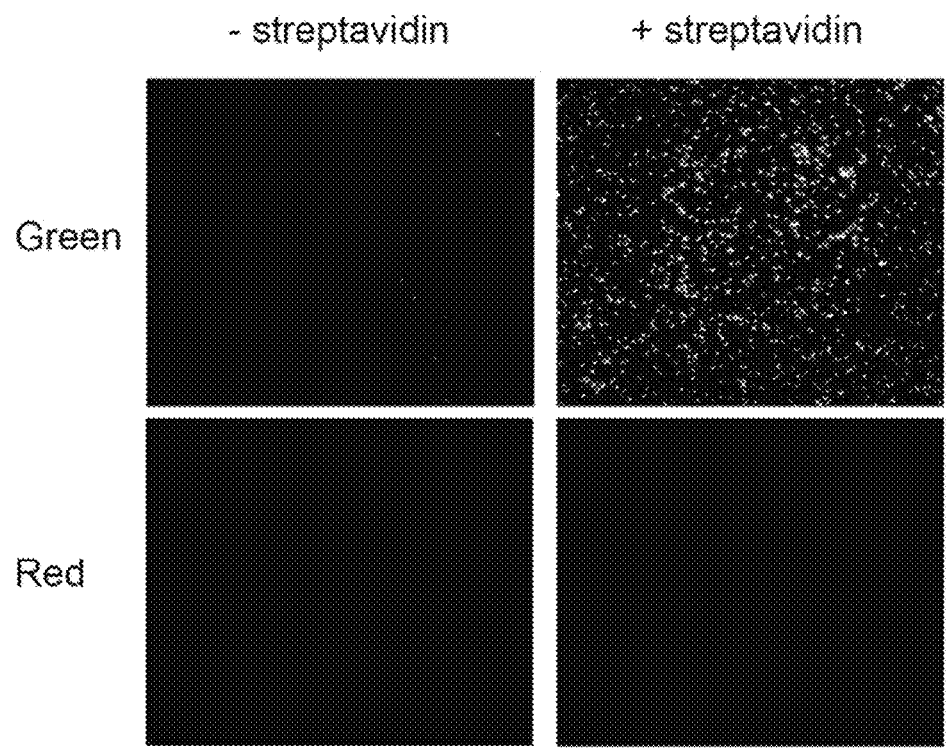
FIG. 6A-6B. Low background and high specificity of single nucleosome anchoring and imaging. (A) Mono-nucleosomes from ESCs were prepared and labeled with Alexa555 (green) as described in FIG. 1A, and added to the flowcell containing a PEG-biotin surface prior to addition of streptavidin. The surface was imaged to detect unspecific background binding. Next, streptavidin was added to the surface, followed by re-incubation with nucleosomes and repeat of the imaging step. Images demonstrate very low fluorescent background prior to addition of nucleosomes, and specific anchoring of nucleosomes to the surface via the biotin-streptavidin interactions. (B) Labeled mono-nucleosomes from ESCs were prepared as in FIG. 1A and anchored to the surface. Single nucleosomes were detected by TIRF imaging, and the fluorophore was chemically cleaved by addition of TCEP. Images demonstrate the high efficiency of the cleavage reaction, resulting in very few residual spots. Remaining spots are imaged and omitted from further analysis.
Figure 6B:
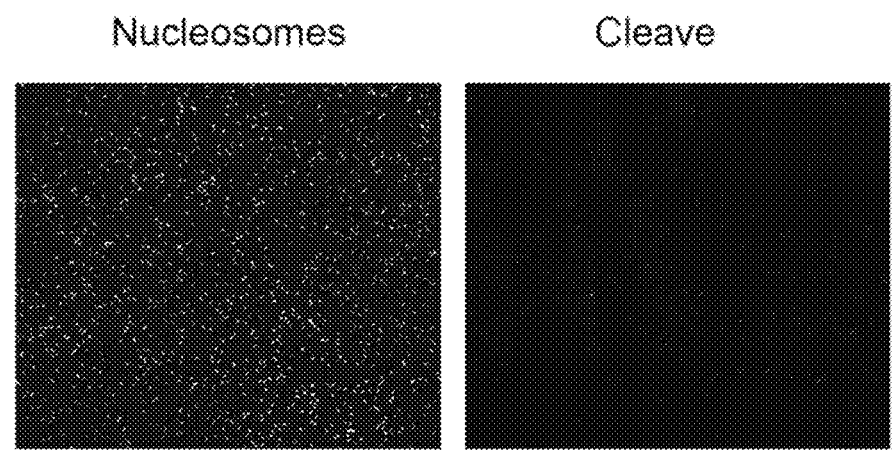

Applicants established a single-molecule-based assay for investigating the nature and functional significance of combinatorial histone modifications (FIG. 1A, 6, 7). Applicants begin by isolating mono-nucleosomes from cells. Applicants lysed cells and treated the chromatin with MNase, which cuts linker DNA between nucleosomes. Nucleosomes are isolated and ligated to fluorescent, biotinylated oligonucleotide adaptors at their free DNA ends. Samples are loaded on 10-30% glycerol gradients and ultra-centrifuged ~18 hours. Fractions are collected and analyzed on gels to select purified adaptor-ligated mono-nucleosomes. Ligated nucleosomes are captured in a spatially distributed manner on PEG-streptavidin coated slides (11,12). The PEG-streptavidin coated slides are assembled in a flow cell. Applicants capture labeled nucleosomes on the surface via the biotin streptavidin interactions. Nucleosome positions are recorded using a TIRF microscope, which excites and detects fluorophores in a thin region and allows single-molecule quantification on planar surfaces. The TIRF microscope used includes two lasers, 532 nm/75 mW and 640 nm/40 mW. After positions are determined, the fluorophore is cleaved and washed away. Applicants then add labeled antibodies for different histone modifications. Repeated binding and dissociation events are monitored over two to three hours, and images are integrated to score modified nucleosomes. In each experiment millions of nucleosomes are visualized. The TIRF microscope captures only target-bound antibodies while eliminating background from un-bound antibodies in solution. The ability to monitor antibody binding and dissociation events temporally allows for quantifying two histone marks simultaneously regardless of any potential steric hindrance. After detection of the first two antibodies, Applicants wash the flow cell and re-image to exclude remaining binding events (~2%). Next, a second pair of antibodies is added and imaged (FIG. 1). As proof of principle, Applicants captured adaptor-ligated mono-nucleosomes from HEK 293 cells, and incubated them with an antibody to histone H3 lysine 9 acetylation (H3K9ac) (FIG. 1B).

Figure 8A:
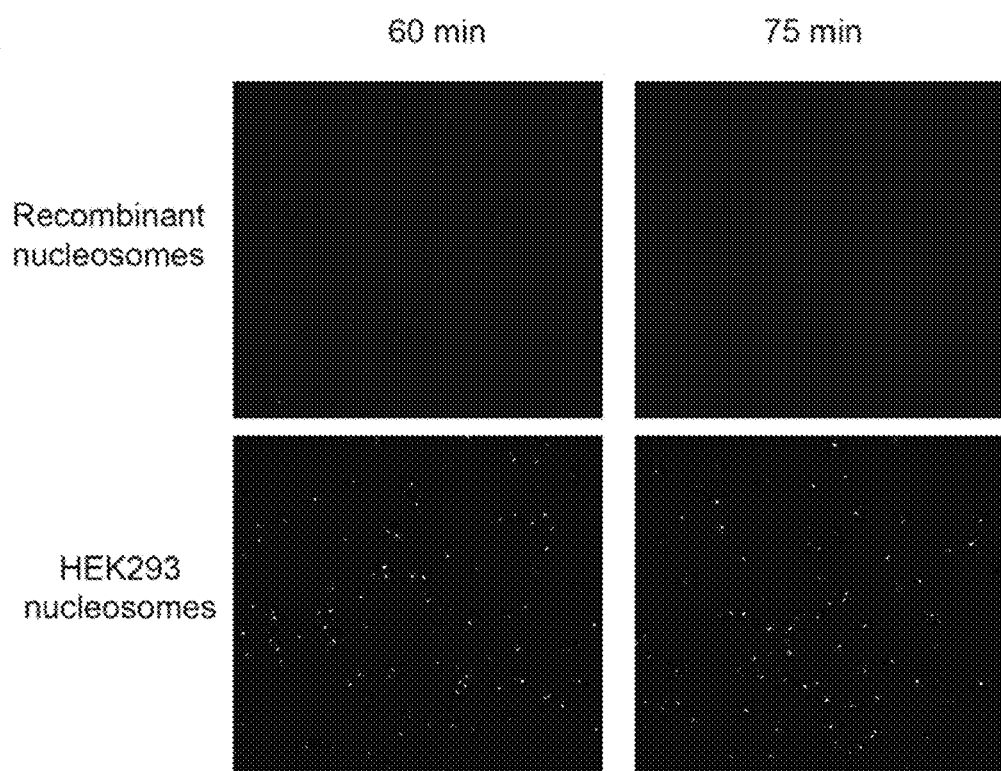
FIG. 8A-8B. Low background and high specificity of antibody binding. (A) Recombinant unmodified nucleosomes were prepared as previously described (91), and then ligated to biotinylated, fluorescent adaptors as in FIG. 1A. Binding of fluorescently-labeled H3K27me3 antibodies was monitored over time. Very few binding events were detected, demonstrating the high specificity of antibody binding. For comparison, also shown are images of H3K27me3 antibody binding to nucleosomes prepared from HEK293 cells. (B) Western-blot analysis of labeled H3K27me3 peptide (TAMRA, green) bound by H3K27me3 antibodies (Alexa647, red). Fluorescent signal on membrane was visualized using a Typhoon trio+imager (Amersham Biosciences).
Figure 8B:
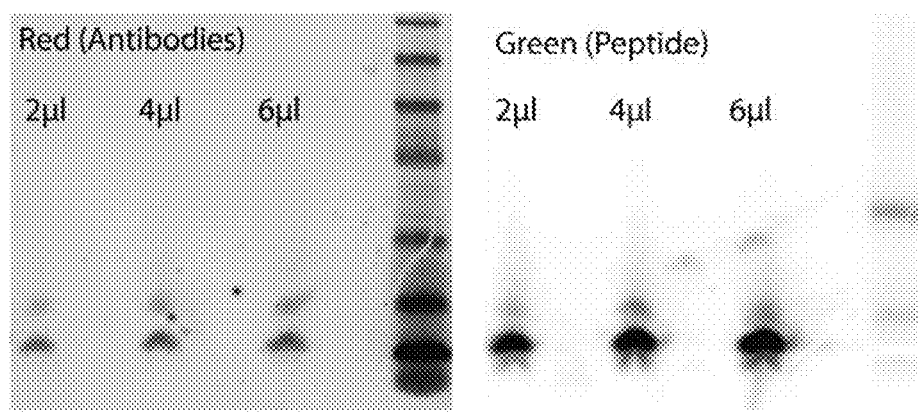
Figure 9A:
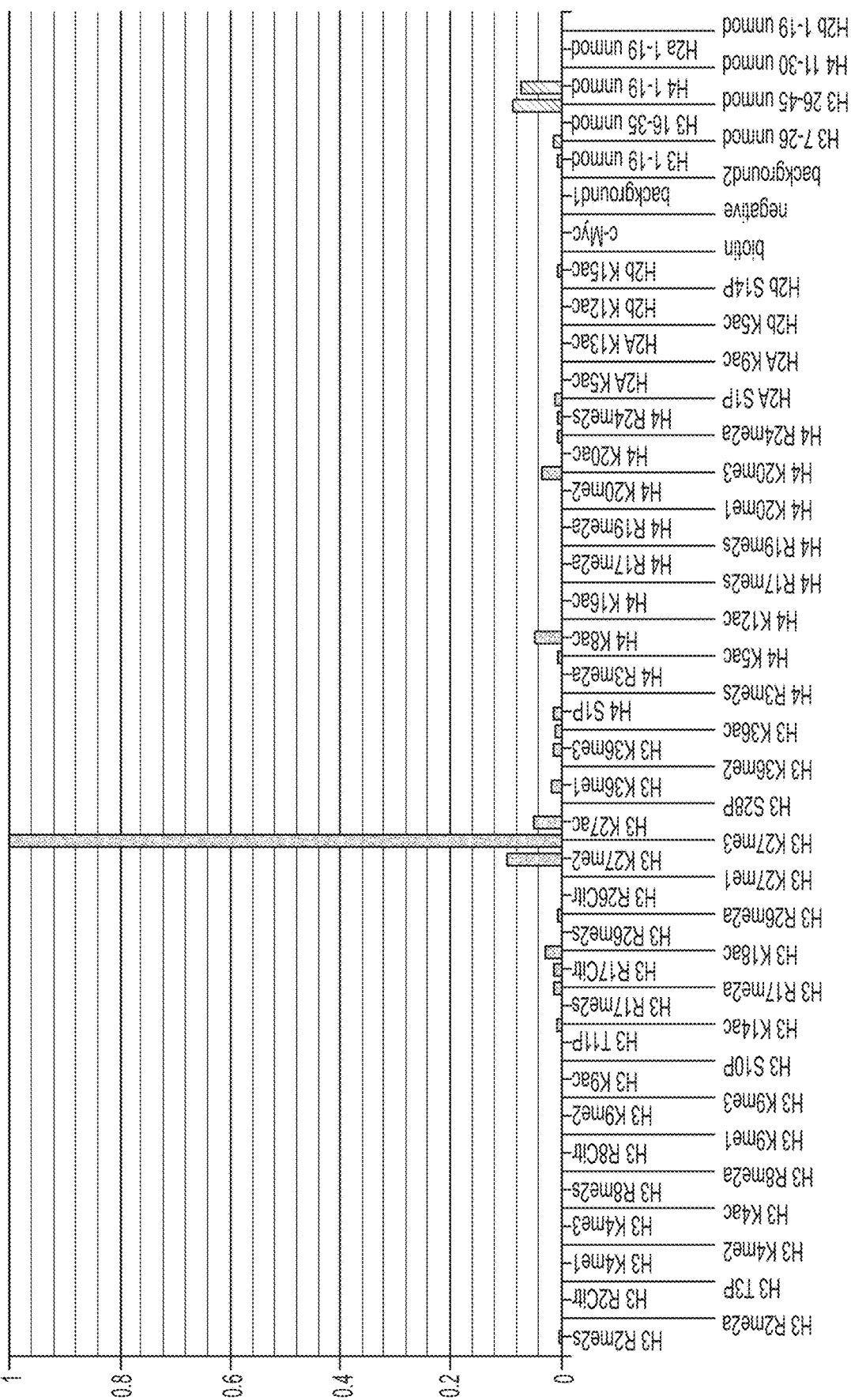
FIG. 9A-9B. Peptide array confirms high antibody specificity (A-B) Reactivity of H3K27me3 antibody (A) or H3K4me3 antibody (B) with control peptides and singly modified peptides. Both antibodies show very high target specificity and low background (see Materials and Methods).
Figure 9B:

Applicants imaged millions of nucleosomes and decoded their modification state. Images are analyzed with Cell Profiler software. Applicants found that while the nucleosome positions were fixed, the H3K9ac antibodies repeatedly bind and dissociate at a specific subset of these nucleosome positions (FIG. 7). Summation of individual binding events over time revealed that ~1% of the nucleosomes are marked by H3K9ac (FIG. 1C). In contrast, when Applicants treated cells with histone deacetylase inhibitors (HDACi), the fraction of acetylated nucleosomes increased to 7% (FIG. 1C, 1D). Importantly, when Applicants repeated the analysis with recombinant unmodified nucleosomes, just 0.1% of nucleosomes scored (FIG. 1E, 8A). Applicants also fluorescently labeled antibodies to H3 lysine 4 tri-methylation (H3K4me3), lysine 27 tri-methylation (H3K27me3), lysine 27 di-methylation (H3K27me2) and lysine 27 acetylation (H3K27ac), and confirmed their specificities by imaging recombinant nucleosomes and peptides, and with dot blots (FIG. 1E, 1F, 8, 9).

Example 2

Characterization of the Pattern of Histone H3 Lysine 27 and Lysine 4 Trimethylation (H3K27me3 and H3K4me3)

In embryonic stem cells (ESCs), developmental gene promoters appear to be concomitantly marked by repressive (H3K27me3) and activating (H3K4me3) histone modifications (13, 14). This 'bivalent' chromatin state is proposed to 'poise' these critical genes for rapid activation or repression upon differentiation. Yet the functional significance of bivalent chromatin remains controversial, in part because current methods do not adequately characterize their structure (15-17). Evidence for co-occurrence of the opposing marks on the same nucleosome comes from immunoprecipitation studies, including sequential ChIP and IP-mass spectrometry (IP-MS) (13, 18-22). Yet such enrichment-based assays yield relative measures and cannot definitely identify an individual bivalent nucleosome. More broadly, ChIP-based comparisons of modifications may be obscured by cellular heterogeneity, difference between alleles, or temporal oscillations between active and repressed states. Applicants therefore leveraged the single-molecule platform to directly quantify the co-existence of these key marks on nucleosomes derived from pluripotent ESCs, from ESCs differentiated to embryoid bodies (EBs), or from fully committed lung fibroblasts. Applicants used single-molecule imaging to decode millions of individual nucleosomes.

Figure 10A:
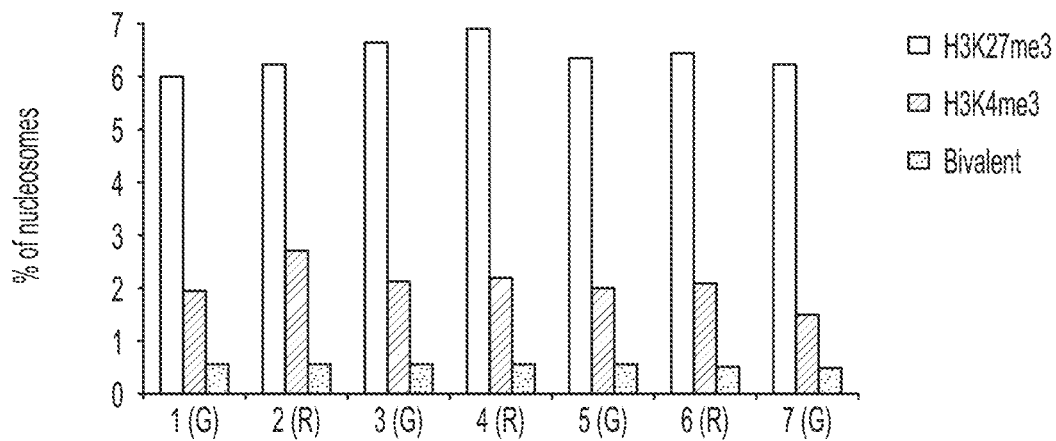
FIG. 10A-10C. Single-molecule imaging of bivalent nucleosomes. (A) Single-molecule imaging was used to decode the modification states of nucleosomes from pluripotent ECSs in seven biological replicate experiments. Nucleosomes were ligated to adaptors containing either Alexa555 fluorophore (green, (G)) or Alexa647 fluorophore (red, (R)). Graph demonstrates high reproducibility between experiments. (B) Decoding of single bivalent nucleosomes. Graph shows the observed and expected percentage of bivalent nucleosomes, corresponds to the data in FIG. 2A, 2B, 2C. (C) Symmetry of bivalent nucleosomes was investigated by probing individual histone H3 molecules isolated from ESCs, biotinylated and spatially distributed on the surface. Time lapse detection of H3K4me3 and H3K27me3 modified tails using labeled antibodies was carried out as in FIG. 1A. Graph shows ~10-fold excess in detection of bivalent H3 tails relative to background.
Figure 10B:
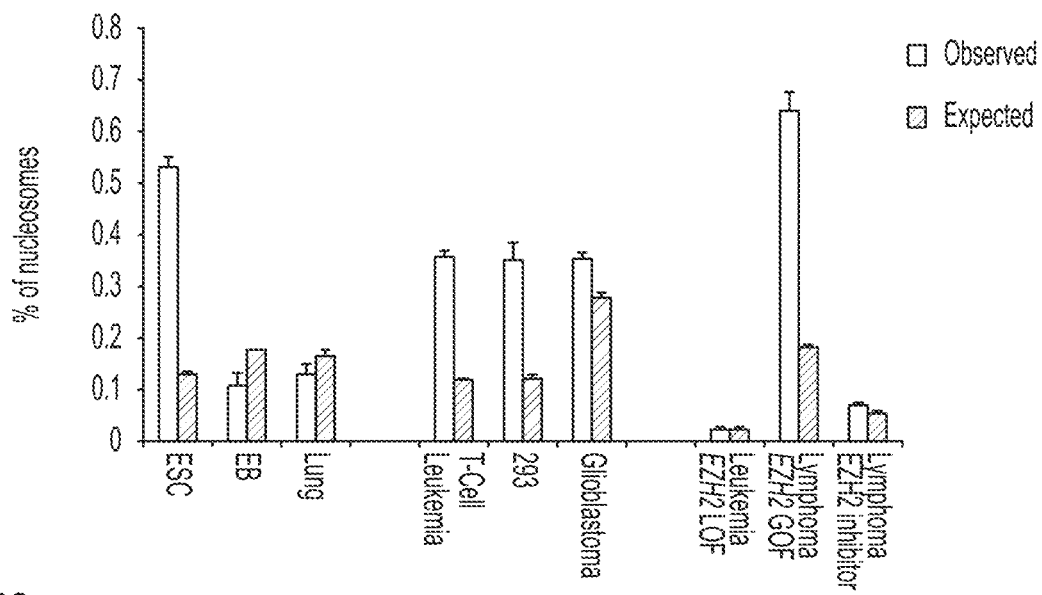
Figure 10C:
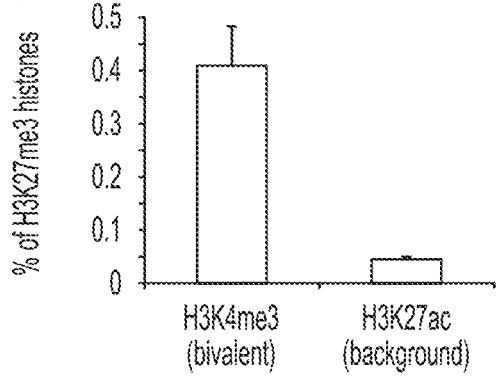
Figure 11:
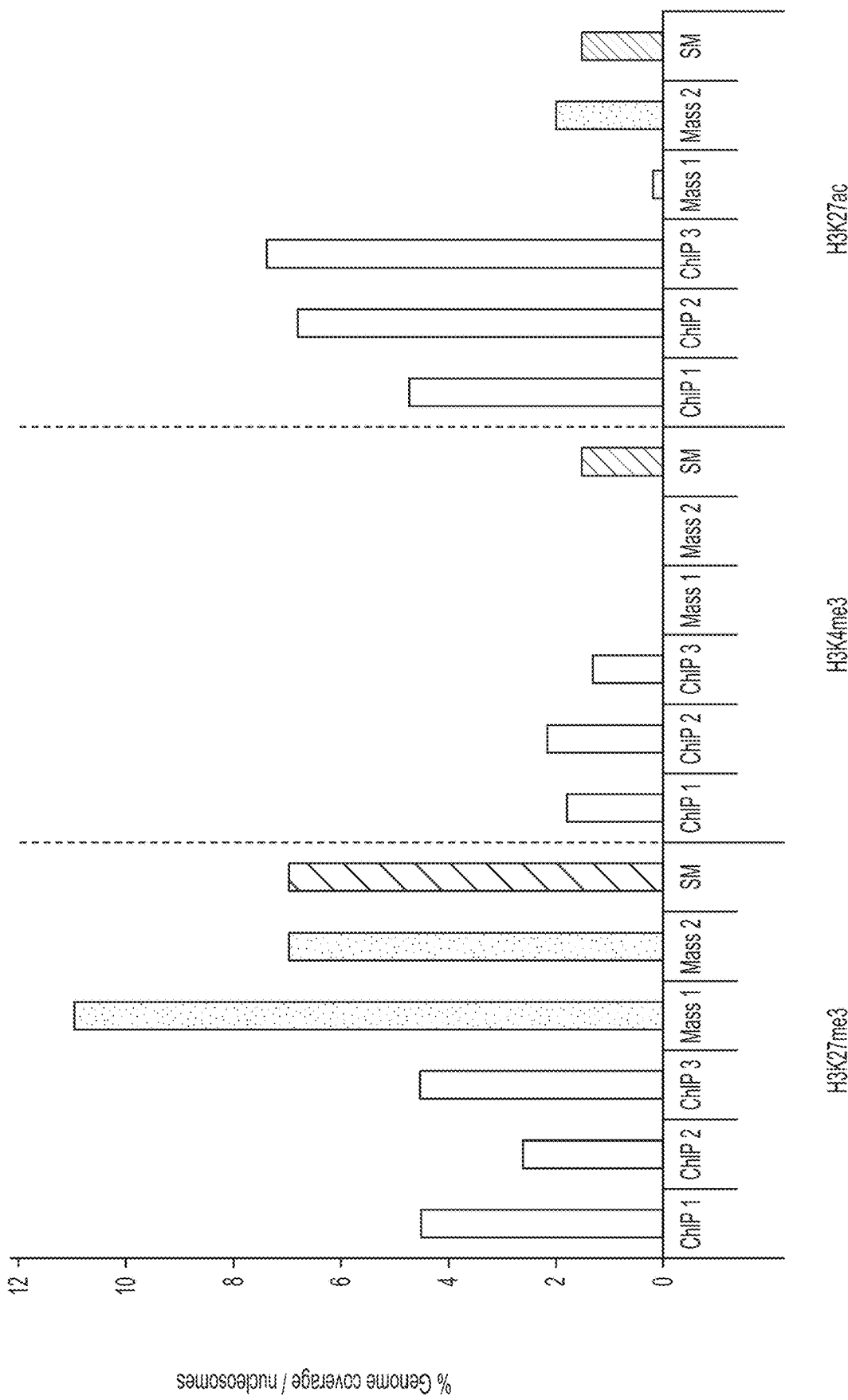
FIG. 11. Comparison of single molecule decoding of histone modifications with conventional ChIP-seq and mass spectrometry. Genomic coverage of H3K27me3, H3K4me3 and H3K27ac was measured in three independent ChIP-seq experiments (see Materials and Methods) and two mass spectrometry assays (Voigt et al. (Mass 1, (18)) and Ferrari et al. (Mass 2, (7))) and compared to the single-molecule (SM) values observed in the current study (no reliable mass spectrometry data is available for H3K4me3). As shown, the single-molecule observations for H3K27me3 and H3K4me3 are in agreement with the other methods. For H3K27ac, however, the percentage of genomic coverage as calculated from ChIP-seq studies is significantly higher than the fraction of H3K27ac peptides deduced by mass spectrometry, or single H3K27ac-modified nucleosomes as deduced from the present study. This may indicate high variability of this modification between cells/alleles (each H3K27ac enriched region in ChIP-seq may only represent a fraction of the cells).

Applicants captured nucleosomes and determined their positions as described herein, chemically cleaved their fluorophores, and then incubated them simultaneously with H3K4me3 (green) and H3K27me3 (red) antibodies. The ability to monitor antibody binding and dissociation events temporally allowed for quantifying both epitopes regardless of any potential steric hindrance (FIG. 7). TIRF imaging revealed that ~6.5% of nucleosomes from ESCs carry H3K27me3 (FIG. 2A, 10). This fraction is somewhat higher in EBs and lung fibroblasts, consistent with prior reports that this repressive mark expands during differentiation (23, 24). In contrast, the fraction of nucleosomes marked by H3K4me3 is slightly lower in the differentiated populations (ESCs: ~2%; EBs: ~1.6%; lung: ~1.6%). These abundances are largely consistent with estimates from bulk ChIP-Seq and Mass spectrometry (FIG. 11). Notably, single-molecule counting revealed that 0.5% of nucleosomes in ESCs carry both marks and thus are truly bivalent (FIG. 2A, 2D, 10). This proportion is significantly greater than the ~0.1% that would be expected from random overlap of two marks present in these proportions. In contrast, in both EBs and fibroblasts, bivalent nucleosomes are much less prevalent and actually depleted relative to random expectation (FIG. 2A). This suggests that regulatory mechanisms actively maintain bivalent chromatin in ESCs.

Applicants next considered whether the method could address the structural relationship between these concomitant modifications. Since each nucleosome has two H3 proteins, a bivalent nucleosome could reflect symmetric co-occurrence of H3K4me3 and H3K27me3 on the same histone tail, or asymmetric marking on opposite tails. The prior observation that the H3K27 methyltransferase PRC2 is inhibited by H3K4me3 would suggest that the two marks cannot reside on the same H3 molecule (25). Moreover, IP-mass spectrometry suggests that bivalent nucleosomes are asymmetric (18). To address this, Applicants extracted individual histone molecules, rather than nucleosomes, from ESCs, biotinylated them and spatially distributed them on the surface (FIG. 2E). Applicants then detected H3K4me3 and H3K27me3 modified tails using labeled antibodies, as above. Applicants found that 0.4% of H3K27me3-modified tails also carry H3K4me3. For comparison, just 0.04% of H3K27me3-modified tails scored for H3K27ac, a combination that is chemically prohibitive (FIG. 10C). This 10-fold excess in detection of bivalent H3 tails relative to background suggests that symmetric bivalent nucleosomes do exist in ESCs. Nonetheless, comparing this proportional overlap on H3 tails (0.4%) to the proportion of H3K27me3-modified nucleosomes that also carry H3K4me3 (7.2%) indicates that 94% of bivalent nucleosomes are asymmetric, while just 6% are symmetrically modified on the same tail. Further studies are needed to determine whether these alternate configurations differ in their functional significance.

Genomic loci marked by bivalent chromatin in ESCs are frequently deregulated in cancer cells (26). Moreover, the Polycomb and trithorax complexes that catalyze H3K27me3 and H3K4me3 are often mutated in cancer (27, 28). Applicants therefore leveraged the single-molecule platform to investigate these modifications in cancer cells (FIG. 2B, 2C, 10B). First, Applicants examined three cell lines that lack known Polycomb or trithorax mutations: T-cell acute leukemia (DND-41), embryonic kidney (HEK293), and glioblastoma (GSC8). Applicants detected bivalent nucleosomes in each of these lines, at levels significantly higher than in the differentiated models (EB, lung), but lower than ESCs. Applicants next examined a leukemia line (SKM-1) with a loss-of-function (LOF) mutation of the PRC2 subunit EZH2 (29, 30) (FIG. 2C). Applicants observed a drastic reduction of H3K27me3-marked nucleosomes, consistent with inactivation of this H3K27 methyltransferase. Applicants also examined a lymphoma cell line (Karpas422) with a gain-of-function (GOF) EZH2 mutation that increases its catalytic activity (30). Here Applicants detected H3K27me3 on a very high proportion of nucleosomes (15%). Notably, bivalent nucleosomes are also prevalent in the lymphoma cells, with roughly half of all H3K4me3-marked nucleosomes carrying H3K27me3 (FIG. 2C, 2F, 10B). Even when controlling for the large fraction of H3K27me3-marked nucleosomes in these cells, the proportion of bivalent nucleosomes is ~4-fold greater than expected from random overlap. This suggests that the mutant EZH2 preferentially catalyzes H3K27me3 on nucleosomes that are marked by H3K4me3. This result is consistent with a prior study that noted increased H3K27me3 over active promoters in EZH2 GOF lymphomas, and proposed bivalency as a mechanism for differentiation block (31). Interestingly, when Applicants treated these lymphoma cells with an EZH2 inhibitor for 3 days (32), Applicants found that H3K27me3 was preferentially lost from bivalent nucleosomes (FIG. 2G). This may reflect increased nucleosome turnover and/or preferential demethylation in such regions. Further study is needed to determine how these early chromatin alterations relate to the therapeutic effects of EZH inhibitors (32).

Thus, the present invention can be used to study complex patterns of the combinatorial histone code, by analyzing many different modifications in each experiment. Specifically, following the addition of two labeled antibodies (green and red, compatible with the two lasers) and imaging as described herein, Applicants can rinse the flow cell and repeat the imaging process with two new antibodies targeting different modifications. Applicants can repeat this process to monitor many modifications in the same experiment, which would allow the construction of a "histone code", reflecting the complex combinations of histone modifications in the genome. In addition, the present invention can be used to label nucleosomes from low-amount samples, such as clinically extracted tumor samples and single cells.

The present invention also allows for single-nucleosome analysis of combinatorial histone modifications in various cell types. Applicants have measured five different histone marks (H3K4me4, H3K27me3, H3K27me2, H3K9ac, H3K27ac) on the same nucleosomes and determined the absolute percentage of each mark in the genome and the combinations of all these marks.

Example 3

Figure 12A:
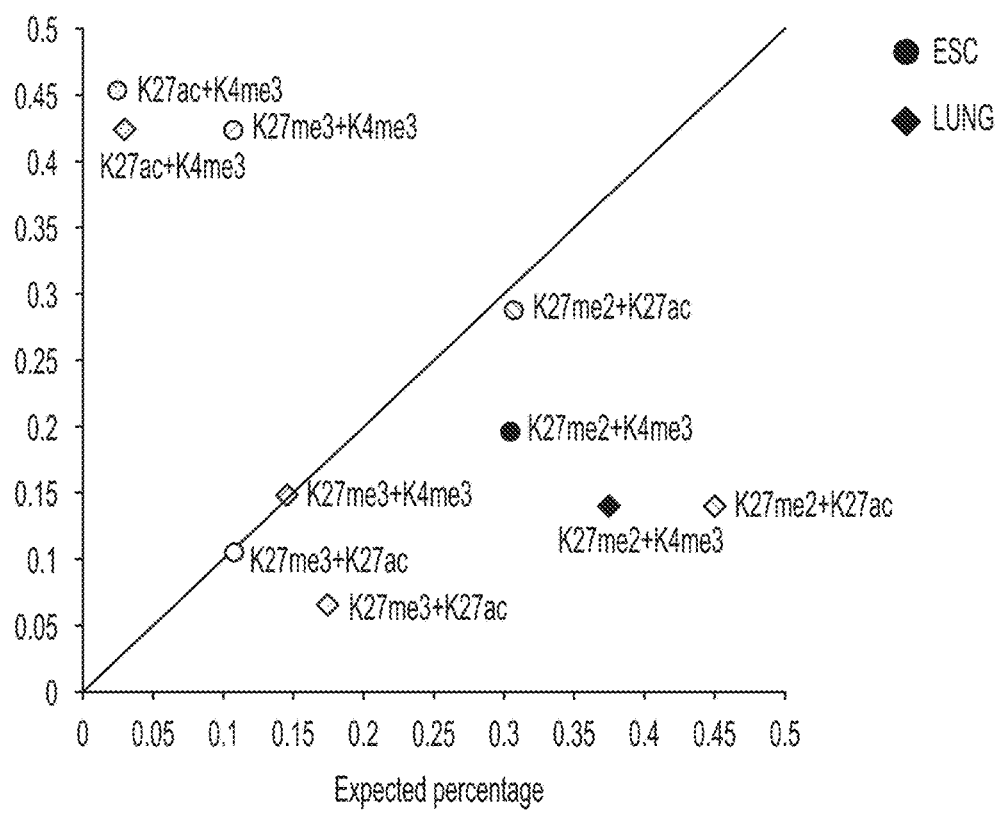
FIG. 12A-12B. Higher-order modification states altered by developmental specification and epigenetic inhibitors. (A) Scatter plot of the observed overlap of the indicated modification pair versus the overlap expected by chance. Corresponds to the data in FIG. 3A, 3B. Combinations of marks above the diagonal are enriched, while combinations below are depleted. (B) Western blot confirms increase in acetylation marks upon HDAC inhibition (Sodium butyrate), and decrease in acetylation upon inhibition of p300 (C646). Corresponds to the data in FIG. 3D.

Applicants next explored other nucleosomal states, including higher-order combinations of the histone modifications H3K4me3, H3K27me3, H3K27me2 and H3K27ac (FIG. 3A). Monitoring four or more histone modifications on single nucleosomes is carried out in successive steps of antibody incubation and imaging, which are separated by a wash step to remove antibodies (see Methods). H3K27me2 is a prevalent modification state associated with large intergenic genomic regions, which are largely exclusive with H3K27me3 regions (7). H3K27ac is an active mark associated with active enhancers and promoters (33-36). Single molecule counting reveals that the proportions of nucleosomes marked by each of the four modifications are similar in ESCs and lung fibroblasts, with exception that the H3K27 methylation levels increase modestly in the differentiated cells (FIG. 3A). However, when Applicants considered these modifications in combination, Applicants observed more striking differences between the cell types, which likely reflect known differences in chromatin dynamics (FIG. 3B, 3C, 12A) (72).

ESC chromatin is enriched for the bivalent combination, and for the pairwise combination of the two active marks, H3K4me3 and H3K27ac. The other pairwise combinations are present in roughly the same proportions as would be expected by chance overlap. The lung fibroblasts are enriched for the pairwise combination of active marks, like the ESCs, but not for the bivalent nucleosomes. However, the lung fibroblast chromatin is depleted for the other combinations (FIG. 3B). This includes the three pairwise states for H3K27 modifications, which are by definition asymmetric (each modification must occur on a different H3 tail within the nucleosome). This interesting distinction between combinatorial modification states likely relates to the alternate chromatin configurations in the respective cell types (FIG. 3C). ESC chromatin is dynamic (37) and may therefore be permissive to co-occurrence of modifications that are associated with different functions and distributed to different genomic locations. In contrast, differentiated cells maintain a more restrictive chromatin state, with stringent partitioning of functionally-distinct modifications to different genomic regions and/or compartments.

Figure 12B:
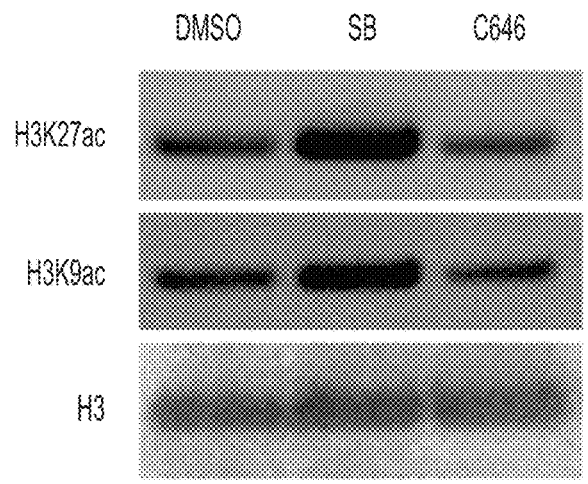

Applicants next sought to study how these chromatin states change as a result of perturbations by inhibitors of histone acetyltransferases (HAT) and histone deacetylases (HDAC). Applicants treated ESCs with a pan-HDAC inhibitor (sodium butyrate; 6 hours) or with a p300 HAT inhibitor (C646; 24 hours) and probed extracted nucleosomes for H3K9ac, H3K27ac, H3K4me3 and H3K27me3. HDAC inhibition significantly increased both acetylation marks, while p300 inhibition had the opposite affect (FIG. 3D, 12B). Neither drug altered H3K4me3 or H3K27me3 over the course of treatment. Interestingly, Applicants found that changes in histone acetylation occurred preferentially on nucleosomes with specific markings. In the case of HDAC inhibition, increased acetylation preferentially affected H3K4me3-marked nucleosomes, consistent with the prior observation that HDACs modulate acetylation levels at active promoters (38,39). In contrast, in the case of p300 inhibition, H3K4me3-marked nucleosomes were more likely to retain their initial state. This may reflect established roles for p300 at distal enhancers, as opposed to H3K4me3-marked promoters. These results demonstrate how single-molecule analysis can provide insight into the functional specificity of chromatin regulators.

Figure 13A:
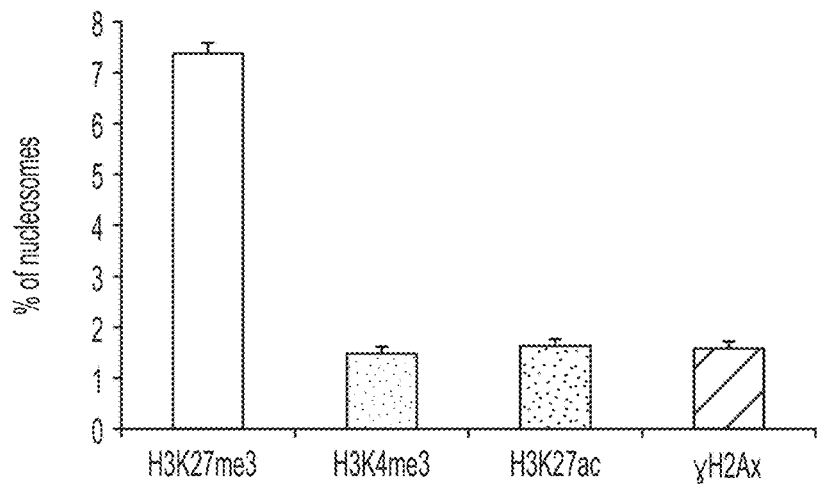
FIG. 13A-13C. γH2Ax is enriched on nucleosomes with activating marks. (A-B) Individual nucleosomes from ESCs decoded for H3K4me3, H3K27me3, H3K27ac and γH2Ax, as described in FIG. 3. (A) Bars depict fraction of nucleosomes marked with the indicated modification. (B) Bars indicate relative over- or under-representation of the indicated modification pair, relative to random expectation, as in FIG. 2A. (C) ESCs were treated with DMSO (control) or HDAC inhibitor (Sodium butyrate). Nucleosomes were isolated and decoded with antibodies targeting H3K27ac and γH2Ax. Plot depicts differences between drug treatment and control for H3K27ac, γH2Ax and their combination.
Figure 13B:
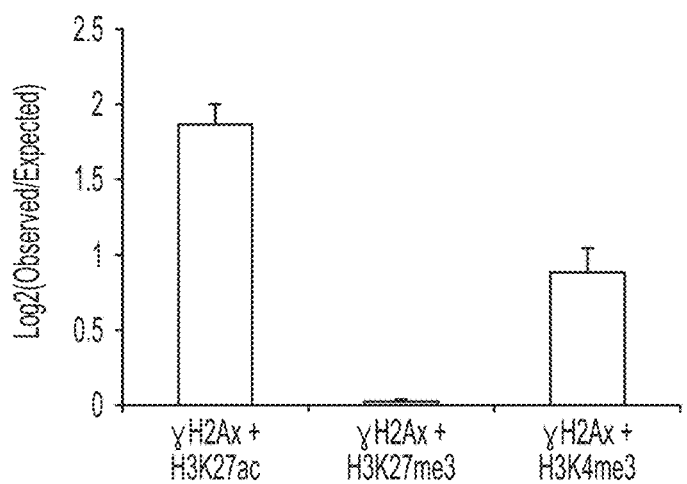
Figure 13C:
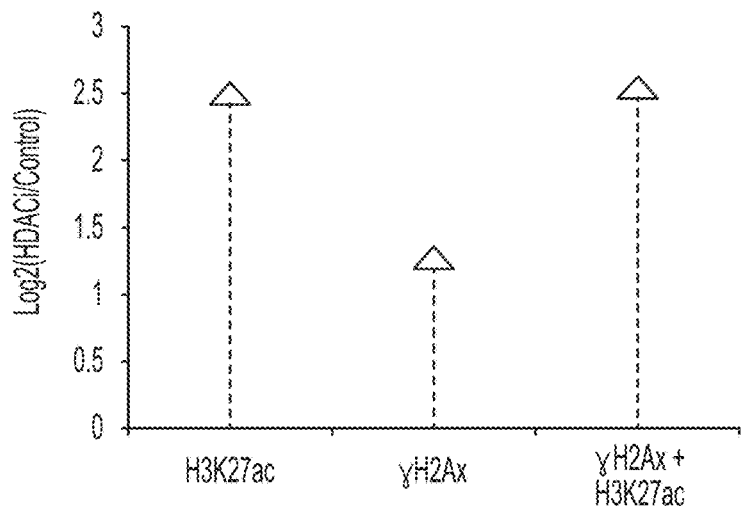

In addition to influences on gene activity, HDAC inhibition may affect genome integrity and chromatin compaction (40,41). Phosphorylation of the histone variant H2Ax (γH2Ax) is one of the earliest and best studied marks of DNA damage. Applicants therefore examined γH2Ax levels on individual nucleosomes extracted from ESCs. Applicants found that ~2% of the nucleosomes contain γH2Ax at baseline, even without exposure to genotoxic stress (FIG. 13A). Combinatorial analysis further revealed that γH2Ax is specifically enriched on nucleosomes with activating marks (H3K27ac and H3K4me3) (FIG. 13B). Moreover, treatment with HDAC inhibitors led to concomitant increases in acetylation and γH2Ax levels (FIG. 13C). These results are consistent with previous studies documenting high baseline levels of γH2Ax associated with decondensed chromatin in ESCs (42), and further support the link between γH2Ax and chromatin hyper-acetylation (43).

Example 4

Single-Molecule DNA Sequencing for the Identification of DNA Sequences Associated with Modified Nucleosomes Applicants sought to bridge this unique ability to decode combinatorial modification states with the ability to sequence and thus determine the genomic positions of individual nucleosomes. Towards this goal, Applicants implemented single-molecule sequencing technology (44, 64) to read the DNA associated with each individual nucleosome (FIG. 4A, 14). As a first demonstration, Applicants captured adaptor-ligated nucleosomes from ESCs and queried their H3K27me3 status as described herein. Applicants then increased the salt concentration on the surface to displace the histone octamers, leaving behind double-stranded nucleosomal DNA. Next, Applicants incubated the flowcell with USER enzyme to excise uracil bases that were previously incorporated into the non-biotinylated strand of the adaptor. This exposed a known sequence on the adaptors, which Applicants used as a priming site for subsequent single-molecule sequencing-by-synthesis reactions (44) (see Methods). Sequencing involved successive rounds of addition of fluorescently-labeled, nucleotide terminators with DNA polymerase reaction mixture. Applicants used TIRF microscopy to detect each base addition, and then chemically-cleave the label and terminator. The process was repeated for up to 180 cycles to determine the DNA sequence of each nucleosomal DNA fragment.

Integration of TIRF images for antibody-based detection of modifications with subsequent sequencing reaction data collected on the same flowcell allowed for coordinately determining the modification state and DNA sequence of each nucleosome (see Methods). Here, Applicants specifically combined images decoding H3K27me3 status of nucleosomes with corresponding single-molecule sequencing data. In the initial pilot experiments, Applicants obtained high-quality sequencing data for 100,000 individual nucleosomes (>21 bases in length). More than 80% of these reads aligned to the genome. Applicants then compared the genomic localization of individual nucleosomes that scored for H3K27me3 with conventional ChIP-seq maps for this modification. Roughly 45% of H3K27me3-positive nucleosomes aligned to genomic regions within H3K27me3 ChIP-seq peaks (FIG. 4C). This is consistent with the 30-50% of reads that map to enriched intervals in a typical H3K27me3 ChIP-seq experiment. For comparison, Applicants found that just 12% of H3K27me3-negative nucleosomes aligned to H3K27me3 ChIP-seq peaks. These results establish proof-of-principle for determining the genomic positions of individual nucleosomes decoded for combinatorial modification states.

Sequencing includes the following steps: (1) eviction of nucleosomes and the non-biotinylated DNA strand. (2) Primer hybridization (primer sequence is initially designed and incorporated into the oligo which is ligated to the nucleosomes). (3) Incubation with one labeled oligonucleotide (A, C, T or G) and polymerase mixture, rinsing the synthesis mixture and imaging. Each spot represents incorporation of that nucleotide by DNA polymerase. (4) Chemical cleavage of the dye-nucleotide linker to release the dye label. (5) Addition of the next nucleotide and polymerase mixture. Steps 3-5 are repeated until the desired average length of sequences is achieved. Applicants can utilize an automated fluidics system that connects to the microscope in order to minimize labor.

Applicants can apply an alternative method to obtain the DNA sequence. This method consists of ligating to the nucleosomes oligonucleotides that contain a photo-cleavable biotin. Thus, following analysis of the histone modifications pattern, Applicants can cleave the biotin of specific nucleosomes in a sample, thus releasing them from the surface of the flow cell and collecting them. Applicants can then amplify the DNA molecules and sequence them using conventional technologies.

Example 5

Characterization of Changes in Histone Modifications During Embryonic Stem Cell Differentiation, Cellular Transformation and Tumorigenesis The present invention can be used to gain further understanding of the changes that occur in the pattern of histone modifications during fundamental biological processes such as cellular differentiation and transformation. Specifically, Applicants use the present invention to study the histone code in ESCs versus differentiated cells at several time points after leukemia inhibitory factor (LIF) removal, which induces differentiation. In addition, Applicants can characterize the pattern of histone modifications in a variety of transformed cell lines and primary tumors, in order to advance the understanding of the epigenetic events that drive tumorigenesis. Of special interest are cancers which are known to be driven by mutations in chromatin regulators, such as B-cell non-Hodgkin's lymphoma. The present invention can be exploited to analyze primary tumors of limited-amount material, and compare the chromatin pattern in these tumors to the normal corresponding tissues.

Example 6

Single-Molecule Analysis of the Chromatin in T Cells

Figure 15:
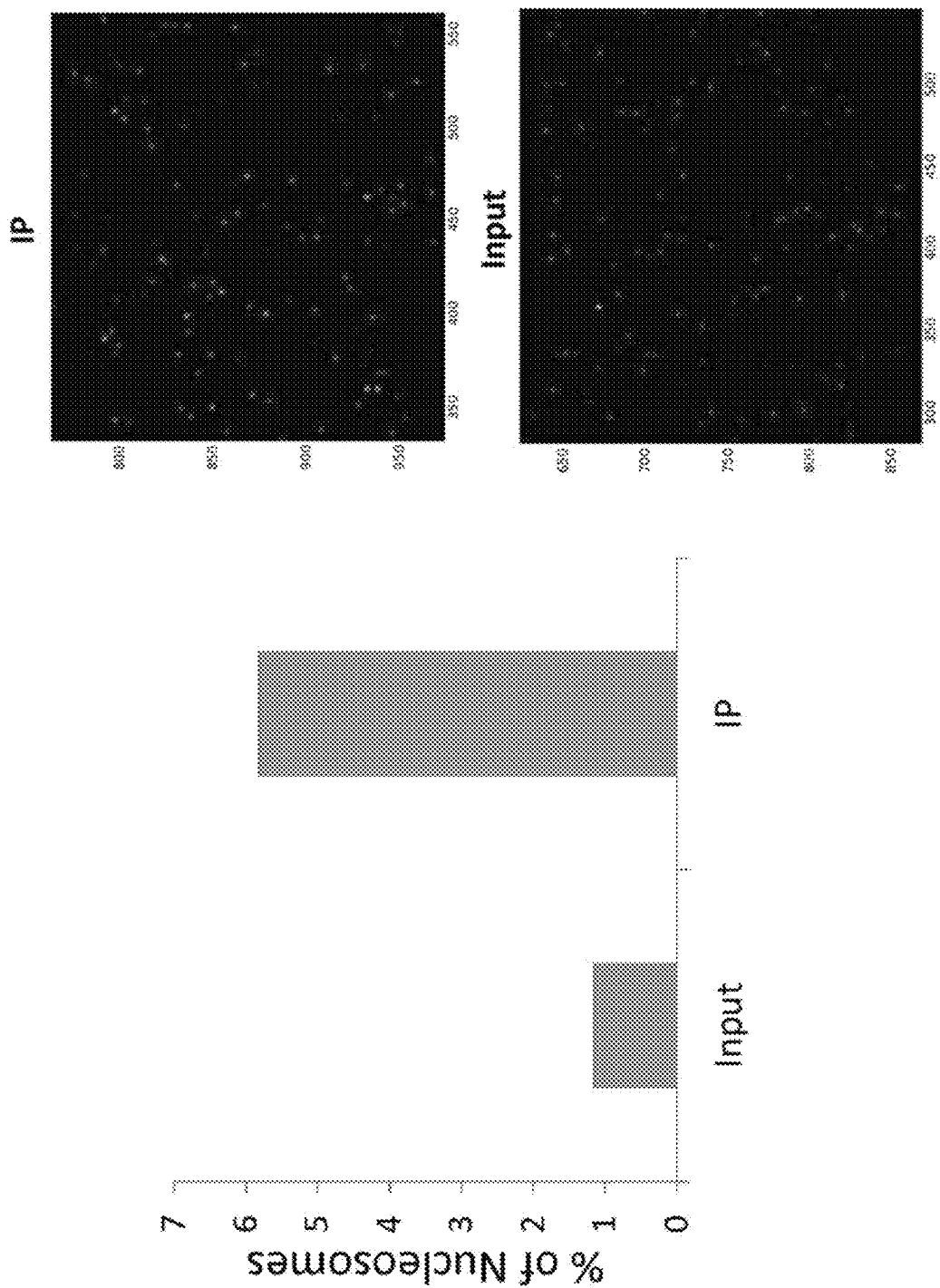
FIG. 15. illustrates enrichment of nucleosomes by performing immunoprecipitation before binding to a solid support.

Applicants can use the present invention to the study primary cells. T cells are a particularly interesting model given their high global levels of the repressive histone modification H3K27me3 and prior reports that they contain higher numbers of poised bivalent promoters than typical lineage-specified cells. Applicants obtain fresh human CD4+ T cells and analyze the association of the five marks indicated herein on single nucleosomes, followed by sequencing the DNA molecules on the surface. Applicants also activate the T cells and collect samples at different time points during the differentiation process (i.e., analyzing distinct populations of $T_H1$, $T_H2$ and $T_H17$ cells). At each time point Applicants isolate nucleosomes and apply the methods of the present invention to directly analyze the chromatin pattern. Based on the results obtained, Applicants can focus on a specific time point and perform in-depth analysis of specific genomic regions (i.e., H3K4me3 nucleosomes to highlight promoter regions, or H3K27ac to highlight enhancer regions, or regions associated with a specific transcription factor). Applicants also enrich for nucleosomes by immunoprecipitation (IP) of the desired mark or transcription factor, followed by direct single-molecule analysis of the chromatin. Performing an IP prior to chromatin analysis allows better coverage of the regions of interest (FIG. 15).

Example 7

Single-Molecule Systems for Profiling Histone and DNA Modifications Genome-Wide

The systems described herein can be scaled to probe larger numbers of modifications over sufficient numbers of nucleosomes for genome-wide coverage. To expand the scope, scale and reliability of single-molecule nucleosome profiling technology, Applicants screen antibodies for specific antibodies to histone modifications or variants. The antibodies are then conjugated to a fluorophore with a desired wavelength. The present invention may be used with different antibodies, fluorophores and labeling strategies. Antibody specificity may be determined using histone modification dot blots (73), which Applicants have established. Validated reagents are benchmarked on the single-molecule system using recombinant (unmodified) nucleosomes and modified peptides. Applicants estimate on/off rates by monitoring antibody binding over time, and establish standard curves for each reagent to facilitate data analysis.

Applicants can increase multiplexing for concurrent detection of 9 histone marks. The TIRF system used in the present application has two lasers, 532 nm/75 mW (green) and 640 nm/40 mW (red), for monitoring two antibodies simultaneously. The TIRF system may be used with a third and fourth laser (e.g., 473 nm or 488 nm), as described herein, for simultaneous imaging of three or four antibodies.

Applicants can monitor antibody binding and release over time by integrating ~10 images per antibody application (the flow cell described herein requires 300 fields, and can be imaged in <15 min). For high-quality antibodies, summation of these images identifies a large majority of modified targets, but Applicants exclude lower affinity reagents that do not pass criteria. Since binding events are queried over time, multiple epitopes can be queried simultaneously, regardless of steric hindrance. The present invention includes procedures for removing or inactivating antibodies on the flow cell, to enable successive application of antibody sets. Applicants can decode nine modifications on a single flow cell in ~6 hours.

The scaled systems and procedures can decode >100 million nucleosomes. The flowcell described herein consists of a single streptavidin coated channel of ~0.8 cm$^2$ surface area. Biotinylated nucleosomes are applied to the surface at dilutions such that they attach in a spatially distributed manner, and can be resolved by imaging. Nucleosome positions are scored by imaging the fluorophore on the adaptor (oligonucleotide sequence) and it is then cleaved. Positions that are overlapping or irregularly shaped are excluded. With this flow cell Applicants can query ~4 million nucleosomes per experiment. A capacity of >100 million nucleosomes per experiment is required for genome-wide coverage (a diploid human genome is packaged into ~30 million nucleosomes). The instrumentation can be modified by introducing a modified flow cell with five channels, each with surface area of ~8 cm$^2$. This surface is imaged by scanning stage, with evanescent wave excitation confined to field of view. Applicants already use a related design, along with faster imaging capabilities. This instrumentation increases coverage by ~50-fold. Procedures for preparing and attaching nucleosomes can be modified, including new adaptor designs, ligation protocols, and loading conditions. Nucleosome spacing is highly variable (average spacing >1000 nm). The theoretical limit for distinguishing molecules by TIRF microscopy is ~200 nm and the practical limit appears to be near 400 nm using standard protocols. Modified procedures can allow an increase in consistency and density of nucleosomes by 2-fold. Computational procedures can be modified to improve the ability to identify singletons and resolve closely spaced nucleosomes. Different surface designs are possible. For example, surfaces with streptavidin moieties attached at regular intervals could allow tighter control, increased densities and improved detection. These modifications can increase throughput to >100 million nucleosomes per channel. In combination with more robust sequencing procedures, this allows the mapping of combinatorial chromatin modifications directly with single-molecule precision and genome-wide coverage.

In preliminary experiments Applicants read the DNA sequence of 100,000 nucleosomes that had been decoded for H3K27me3. To establish robust systems for mapping combinatorial modification states with digital resolution and genome-wide coverage Applicants can modify the surface chemistry to increase stability and robustness. The PEG-Streptavidin surface used to anchor the nucleosomes is highly stable for several hours in room temperature, thus enabling monitoring of antibody binding and dissociation events. However, the sequencing reaction requires successive cycles with addition of fluorescent nucleotides and extensive washing, over ~60 hours at 37° C. Applicants found that a large majority of nucleosomal DNA molecules are lost from the surface during this time, possibly due to stripping of PEG-biotin from the glass. Moreover, PEG-Streptavidin surface chemistry has some background fluorescence that compromises the single-molecule sequencing, which relies on consistent detection of individual fluorophores. As a result, Applicants obtained sufficiently long sequencing reads (20-50 bases) for only a fraction of the decoded nucleosomes. Different surface chemistries can be used (e.g., ZeroBkg PEG, non-epoxy silane). Surfaces must allow for discrete antibody detection in a complex mixture, and also not inhibit subsequent sequencing steps. The stable surfaces must have limited fluorescent background and non-specific binding. Blocking reagents are used to neutralize charge and lower non-specific antibody adhesion.

Applicants used a biotin surface for imaging nucleosomes purchased from Microsurfaces Inc. (Englewood, N.J.). This PEG-biotin surface was not stable enough to allow sequencing. Applicants generated a second surface that is stable during sequencing. The second surface is a biotin surface where the biotin is deposited on the surface by use of an oligo that contains two biotin molecules that is conjugated to the surface (FIG. 16). In both cases nucleosomes are captured on the surface via the biotin-streptavidin interaction. The surface from Microsurfaces contains PEG that blocks unspecific binding of the antibodies. The second surface uses spermine tetrahydrochloride to block unspecific binding of antibodies. The surface requirements for nucleosome capture and sequencing were selectivity for nucleosome complexes, stability during exposure to various chemical steps during sample interrogation and stability during sequencing runs. To create an effective capture surface, the 3' oligo ends were amine modified for surface attachment and the 5' ends were 2× labeled with biotin for efficient streptavidin coupling.

Additionally, imaging exposure time, objective/focal settings, effective laser power, camera sensor architecture and camera gain settings can be adjusted. Other adaptor designs (e.g., functional modifications, sequence variations) can improve the stability of the attached nucleosomal DNA. These optimizations can increase stability of the DNA attachments and improve detectability of each molecule, allowing the acquisition of high-quality sequencing data for a larger fraction of decoded nucleosomes.

Upgraded sequencing systems can reduce cycle time and increase throughput. Acquiring reads of sufficient length (25+ bases) requires ~120 sequencing cycles, each involving successive addition of four nucleotides (C,T,A,G). This accounts for a vast majority of run time (~60 hours). Cycle times can be reduced by adjusting laser power and exposure time, as well as camera sensor architecture and gain settings. Two fluorophores can be incorporated into the chemistry mixture (i.e., for different nucleotides), which can reduce sequencing time by 50%, and can increase read lengths by reducing nucleotide mis-incorporations that lead to strand termination. Although Applicants considered adapting the surfaces for bridge amplification and sequencing on Illumina instruments, Applicants found that their systems are incompatible with the protein capture and detection steps that are fundamental to our application.

Applicants can increase coverage to >10$^8$ nucleosomal DNAs per channel by adapting the instrumentation and procedures. Sequencing output is a function of imaging area and surface density. Larger flow cells and increased loading densities increase coverage by 1-2 orders of magnitude. Moreover, increased surface stability and reduced run times allow for obtaining high-quality of reads for a large fraction of nucleosomes. Finally, samples can be run across multiple channels to ensure ample coverage for genome-wide mapping.

Example 8

DNA Modification Detection

The system may be used with procedures for concurrent detection of DNA methylation and other DNA modifications. After histone modification detection, histones can be released by 2M NaCl, retaining DNA strands at identical positions. In addition to enabling direct sequencing this allows concurrent detection of DNA modifications. Genomic DNA is subject to several modifications, most notably the methylation of cytosines (5-mC) within CpG dinucleotides (74). TET and TDG enzymes catalyze further alterations, including 5-hydroxymethyl- (5-hmC), 5-formyl- (5-fC) and 5-carboxy- (5-caC) cytosine (75). Evidence also supports rare modification of other bases in the human genome (76). Notably, functional DNA elements can be distinguished by differential methylation patterns. Antibodies with specificity for 5-mC, 5-hmC or other modifications can be used. Reagents can be confirmed for specificity, DNA can be labeled as with histone modifications and applied to flow cells after histone displacement. Methyl-CpG-binding domains (MBD2) and CXXC proteins (bind unmethylated CpGs) can also be used to distinguish methylated from un-methylated CpGs with greater specificity (77).

In alternative approaches, DNA modifications can be detected by methods that include using chemicals or enzymes to further modify specific bases in ways that facilitate their detection. Un-methylated cytosines can be bisulfite converted, to allow reading methylation at base-resolution. Analytic tools to interpret signals from single-molecule methylation assays can be used. These use the corresponding sequencing data to infer the cytosine and CpG content of the protected nucleosomal sequence (~146 bp). This additional capability allows direct comparative analysis of chromatin modifications and DNA methylation at the single molecule level, and provides a unique tool for studying genomic elements and regulatory mechanisms.

For techniques useful in detecting DNA methylation in a biological sample reference is made to: Methods in Molecular Biology, Volume 507, 2009, DNA Methylation Methods and Protocols, Editors: Jorg Tost, ISBN: 978-1-934115-61-9 (Print) 978-1-59745-522-0 (Online).

Example 9

Pipelines for Intergration of Genome-Wide Maps of Combinatorial Chromatin States Pipelines can be established to integrate genome-wide maps of combinatorial chromatin states. The pipelines control automated processing of the combinatorial chromatin modification data and sequencing data. Our preliminary studies required step-wise processing and integration of imaging data, with chromatin image data processing followed by sequencing image data processing, followed by integration of features with overlapping x,y coordinates. Robust and automated procedures for image processing and analysis, and for integrating the data into combinatorial maps can improve processing and integration. Specifically, an integrated pipeline can detect chromatin modifications and align genomic data to a genome of choice. First, existing image analysis algorithms are adapted for single-molecule sequencing data to process data collected on a system, while retaining spatial information for integrating modification data. The pipeline can be adapted with implementations from the preliminary studies so it can also process, align and integrate images from antibody binding stages. The respective data is overlaid based on aligned positional information (x,y coordinates) to annotate, for each individual nucleosome, its combined modifications and its DNA sequence. The pipeline can generate separate fastq files per modification or combination of modifications, amenable to further processing with standard pipelines for aligning, segmenting, quantifying and visualizing the data.

Example 10

Combinatorial Analysis of Rare Samples and Single Cells

The single-molecule systems can also be adapted for to map chromatin in rare samples and single cells. The single-molecule assay for combinatorial chromatin mapping is compatible with rare samples and even single cells. In practice, current methods for preparing nucleosomes start with millions of cells, however, methods can be used for interrogating small populations (~500 cells) or single cells on the single-molecule systems. Applicants can utilize established procedures for manipulating low input samples and single cells, and for using DNA barcodes to index chromatin by originating cell/sample (59,60,68).

Figure 5:
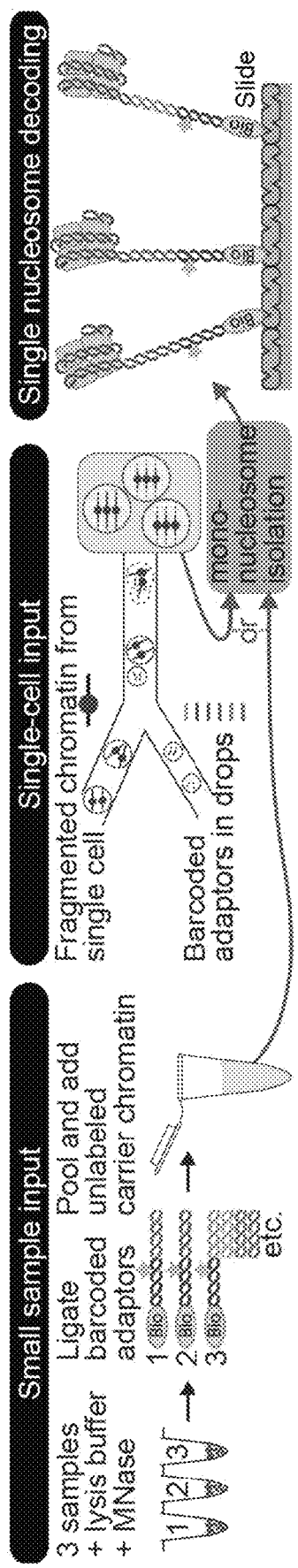
FIG. 5. Multiplexed analysis of rare samples & single cells. Left: In Mint-ChIP, chromatin is barcoded, pooled and split for analysis of multiple marks and samples. Middle: In Drop-ChIP, microfluidics is used to barcode chromatin for single-cell analysis. Right: Combination of these methods with single-molecule systems for analysis of rare cell types and single cells.

Indexed chromatin from small cell numbers can be prepared. Although successive technical improvements have reduced input requirements of ChIP-seq from millions to thousands of cells (51,68,78) the methods remain tedious and inconsistent. Applicants therefore developed a new iteration of ChIP-seq, termed Mint-ChIP (59), that leverages small sample handling methods (68) and direct chromatin barcoding (57,58) for multiplexed analysis of small samples. Mint-ChIP isolates mono- and oligo-nucleosomes from as few as 500 cells by MNase digestion (FIG. 5). The chromatin fragments are immediately ligated to double-stranded DNA adaptors, which contain an 8-base pair barcode for sample indexing, and a T7 promoter for linear amplification. Adaptor-ligated chromatin from different samples is then pooled (each sample has a different barcode), mixed with unlabeled carrier chromatin, and split for parallel ChIP assays for different modifications. This pool-and-split approach enables multiplexed assessment and comparison of multiple chromatin marks across multiple low input samples (59).

Applicants can also barcode chromatin from single cells using microfluidics, as described herein. Applicants can utilize droplet microfluidics technology to tag nucleosomes by cell of origin prior to application of the single-molecule assay of the present invention. This is based on barcoding of individual cells in a droplet. Applicants can then read out the 'cell identity barcode' by sequencing or hybridization on the imaging system of the present invention. Thus, the epigenetic landscape of single-cells is determined.

To investigate cell-to-cell epigenetic variability, Applicants combined chromatin barcoding and drop-based microfluidics to acquire low-coverage chromatin profiles for thousands of single cells (60). In "Drop-ChIP", cells are encapsulated in aqueous drops with lysis buffer and MNase, and injected into a microfluidics device. Each drop, which now contains chromatin fragments from one cell, is injected with ligase and a unique barcoded adaptor. After barcode ligation, the contents of thousands of cells are combined for conventional ChIP-seq (FIG. 5). Sequencing reads are attributed to cells by the barcode read. In H3K4me3 and H3K4me2 experiments, Applicants detect ~800 peaks/cell (5% sensitivity). Despite this low coverage, clustering algorithms enabled us to distinguish hidden ES cell sub-populations (60).

Preliminary results established methods for manipulating, preparing and barcoding chromatin from small samples and single cells. Applicants can combine high-sensitivity preparative and barcoding methods with the single-molecule techniques to interrogate rare cell types and single cells. Moreover, the multiplexing capabilities allow for adapting the single-molecule systems for high-throughput analyses of multiple cell states, genetic perturbations and/or inhibitor treatments, enabling new functional and mechanistic studies.

The methods described herein can be adapted for preparing chromatin from limited samples. The methods can be used to prepare and fragment chromatin from small samples (59,68), using carrier chromatin to minimize sample loss (79,80). Applicants can lyse and MNase digest aliquots of 100 to 1,000 human cells. Applicants have found that accurate cell counting on hemocytometer, rapid processing in small volumes, titration of enzyme by cell number and low-bind plates/pipette tips are critical for processing such limited samples (59,68). In parallel, Applicants can prepare carrier chromatin from one million mouse cells. Applicants can ligate fluorescent, biotinylated oligonucleotide adaptors to the human chromatin, but not to the carrier chromatin. Applicants can then mix the samples and use glycerol gradient centrifugation to isolate mononucleosomes. Applicants can titrate chromatin loading onto the flowcell to reach an appropriate density of attached nucleosomes. Carrier chromatin, which lacks biotinylated adaptors, should not attach. Applicants can test for contamination by aligning sequenced reads to the mouse genome. With 20 bp reads and stringent alignment requirements, Applicants can expect ~95% of sequences to align specifically to the human genome. In combination with the improved systems described herein, these procedures allow for the preparation of nucleosomes and the mapping of combinatorial modifications in extremely rare cell types.

Applicants can develop barcoding methods for multiplexed analysis of multiple samples and conditions. The ability to perform multiplexed analysis of multiple samples on the single-molecule systems provides for functional genetic screens and characterization of epigenetic drugs and chemical probes. Applicants therefore can develop such capabilities by indexing chromatin fragments with distinct fluorophores or DNA barcodes. Applicants can use adaptors with different fluorophores to label separate samples of nucleosomes, as described herein, and interrogate them simultaneously on the single-molecule system. The first step in the image analysis would be to simply record the fluorophore associated with each nucleosome, thus determining the sample from which it originated. After chemically cleaving the adaptor fluorophore, Applicants can decode modifications and sequence. This adaptation is one embodiment towards multiplexed systems for digital comparison of samples (e.g., to evaluate genetic or chemical perturbations).

Next, Applicants can develop procedures to index up to 96 different samples with DNA barcodes for multiplexed analysis. Applicants can generate adaptors with six base DNA barcodes immediately downstream of the sequencing primer site. Different samples can be ligated to adaptors with different barcodes, and then combined for nucleosome purification, decoding and sequencing. The first six bases of the sequencing reads allow for assigning each nucleosome to its originating sample. Applicants can optimize procedures using chromatin samples from different species. These multiplexing procedures should enable high-throughput analysis of multiple cell types, conditions or perturbations, thus advancing capabilities for functional genomics.

Applicants can develop barcoding methods for single-cell chromatin profiling. In preliminary experiments, Applicants combined DNA barcoding with drop-based microfluidics to index chromatin by originating cell, and thereby acquire low-coverage chromatin profiles for thousands of single cells (Drop-seq)(60). However, this method still depends on a low efficiency ChIP pull-down and yields few reads/cell (~2000). Here, Applicants can combine these microfluidics procedures with the single-molecule systems to acquire high-quality chromatin maps for single cells. Applicants can use the microfluidics to lyse single cells, digest their chromatin and index nucleosomes to originating cell. In this case, the nucleosomes are ligated to adaptors containing both barcode and biotin. Applicants then combine the contents from thousands of cells, and prepare nucleosomes for single-molecule analysis on the flow cell. As described herein, sequencing reads also decode the barcodes, allowing for assignment of nucleosomes to originating cells, and thus derive single-cell maps. The combined workflow can advantageously allow investigation of single-cell chromatin states and cell-to-cell epigenetic variability. The established methods can be used to barcode nucleosomes from single cells. Not being bound by a theory, adding these nucleosomes to the single molecule systems described herein will result in no loss of nucleosomes as long as enough surfaces are used to allow each nucleosome to be accommodated, whereas with traditional immunoprecipitation methods a majority of chromatin fragments are lost.

Example 11

Transcription Factor Analysis

Applicants can relate combinatorial transcription factor interactions and chromatin states on gene regulatory elements. Described herein are procedures for unbiased isolation and analysis of nucleosomal fragments (~150 bp) to map combinatorial chromatin states genome-wide. A complementary strategy can enrich and deeply analyze larger chromatin fragments from loci under active regulation (e.g., gene regulatory elements). Methods include digesting, enriching and capturing chromatin fragments comprising regulatory DNA. Here, Applicants exploit the accessibility of regulatory DNA to release larger chromatin fragments under active regulation. These fragments are decoded for transcription factors and histone marks and sequenced. The methods are adapted for releasing and tagging accessible chromatin. Tn5 transposase provides an effective means for integrating DNA adaptors into accessible 'open' chromatin (ATAC-seq) (50,81), which is enriched for regulatory elements. Applicants can use this method to release chromatin fragments from loci under active regulation. After transposition, Applicants can ligate the fluorescent, biotinylated adaptors to the free DNA ends. Applicants then centrifuge samples (or apply a gradient) to isolate chromatin fragments in a size range from ~0.5 to 2 kb. Applicants can also fix cells with formaldehyde prior to Tn5 transposition. Consistent with prior studies (82), Applicants find that Tn5 transposition can effectively fragment fixed chromatin. Applicants can also perform additional steps such as light sonication to improve the efficacy of Tn5 transposition on fixed chromatin. Applicants can evaluate the chromatin preparations by sizing gel and paired-end sequencing to effectively enrich regulatory chromatin regions of desired length. Finally, Applicants can apply and capture these larger fragments to the solid surface for decoding and sequencing.

Certain alternative embodiments include partial MNase digestion. When applied at low concentrations for a short time, MNase preferentially digests accessible chromatin regions (51). MNase digestion conditions with specific concentrations and/or time can be used to enrich regulatory DNA, assessing the resulting products by sizing gels and paired-end sequencing as described herein. Fixation strategies should allow efficient release of large accessible regions, while maintaining transcription factor associations.

Certain alternative embodiments include immunoprecipitation (IP) of regulatory chromatin. Applicants can adapt ChIP procedures for this purpose. Applicants can prepare fixed chromatin with relatively large fragments (~0.5 to 2 kb) and IP with an antibody to H3K27ac (to enrich enhancer-like regions) or H3K4me3 (to enrich promoters). Intact chromatin fragments can be released from the beads without contamination from antibody or other reagents. Applicants can then ligate adaptors for single-molecule analysis.

Applicants can detect transcription factors and histone modifications on the isolated chromatin fragments. Here, Applicants can probe transcription factors and chromatin marks on the extended regions of regulatory chromatin. The loading concentrations, buffers, and surface chemistry can be modified to capture these larger fragments in a spatially distributed manner. Applicants can use cleavable fluorophores on the adaptors to locate individual fragments, and exclude overlapping molecules from analysis. Applicants can then successively probe these chromatin molecules for chromatin modifications and transcription factors, using multiple colors and washes to remove antibodies between steps. Applicants can screen and label transcription factor antibodies, as described herein, to create suitable reagents. These single molecule systems and procedures can provide for charting combinatorial transcription factor interactions at scale, thus providing new insight into cooperative (and exclusive) binding patterns that enable combinations of transcription factors and chromatin states to modulate regulatory elements.

Detection of transcription factors presents several challenges. In some embodiments, transcription factor applications require fixed chromatin. This can pose problems in capturing the fragments and/or increase signal-to-noise. Some antibodies may not recognize cross-linked epitopes. In some embodiments, light cross-linking (low formaldehyde) is performed. In some embodiments, chromatin is de-cross-linked prior to detection. In some embodiments, cross-linking is not performed, limiting the analysis to factors that remain bound under native conditions (e.g., CTCF).

Genomic identity of each fragment can be determined by sequencing or by using CRISPR-Cas9. Applicants can use established methods to identify the genomic locus from which these extended chromatin fragments originate. In one embodiment, single-molecule sequencing of cross-linked regulatory DNA is performed. Single-molecule sequencing methods as described herein are adapted to identify the extended chromatin fragments. This DNA may initially be cross-linked to proteins to maintain transcription factor interactions. Various methods for reversing cross-links on the surface of the flow cell, while avoiding dissociation of DNA molecules can be used. Based on preliminary data, incubation in high salt with proteinase K at modestly elevated temperatures will reverse cross-links to an extent that Applicants can sequence short reads at the end of each fragment (20-25 bases). Indeed, Applicants previously performed direct single-molecule sequencing of de-crosslinked ChIP DNA (69). The surface chemistry may also be modified as described herein to withstand more stringent de-crosslinking conditions. After removal of protein and cross-links Applicants can continue with primer hybridization and sequencing-by-synthesis, as described herein.

In one embodiment, a locus can be identified by CRISPR-Cas9 recognition. Cas9 is an RNA-guided endonuclease that uses RNA/DNA complementarity to cleave double-stranded DNA at target loci with high specificity (84). Catalytically-inactive Cas9 (dCas9) with a fluorescent label has been used to follow the dynamics of CRISPR-Cas9 binding to chromatin in living cells (85). In addition, CRISPR-Cas9 can be used to label specific loci by nick translation: Cas9 D10A contains a nuclease disabling mutation that creates a guide RNA-directed nick in the DNA instead of a double strand break. Fluorescent nucleotides can then be incorporated at the site by DNA polymerase, thus labeling sequences targeted by the guide RNA (86). Importantly, CRISPR-Cas9 approaches for labeling genomic regions do not require global DNA denaturation and can be applied directly to chromatin, even after fixation (87). Therefore CRISPR-Cas9 specificity is an alternate means to identify the genomic loci associated with extended chromatin fragments. After decoding transcription factors and modifications, Applicants can wash antibodies from the flow cell, and add in vitro-assembled CRISPR-dCas9 complexes with guide RNAs that target specific loci of interest. In alternate embodiments, either Cas9 or the guide RNA may be fluorescently labeled or both are labeled in different colors to increase specificity. Applicants can add different CRISPR-dCas9 complexes sequentially, imaging after each addition. This should allow detection of large numbers of loci (100s), limited only by assay time. In other alternative embodiments, Applicants can target introduction of DNA nicks by Cas9 D10A for locus identification. Nick translation can be carried out with fluorescent nucleotides and the same DNA-polymerase used in the single-molecule DNA sequencing, thus enabling successive rounds, each targeting a different locus.

Discussion.

The present invention provides a single molecule platform to read out combinatorial histone modifications on individual nucleosomes. The methods require a low amount of material, does not require simultaneous binding of different antibodies, and addresses major shortcomings of ChIP-seq. Applicants have confirmed that bivalent nucleosomes with opposing marks exist in ES cells. Applicants have shown that bivalency is mostly on opposing H3 tails (asymmetric). Applicants have shown that distinct combinations of histone marks are present in ES cells versus lung fibroblasts. Applicants have shown that an aberrant chromatin pattern is present in a human B-cell non-Hodgkin's lymphoma cell line consisting of a very high percentage of H3K27me3 nucleosomes and a high frequency of bivalent nucleosomes. Additionally, the perturbation of histone marks reveal unexpected combinatorial patterns.

The present invention can be used to chart and investigate the functions of higher-order combinations in development and cancer. The present invention allows the creation of a genome-wide combinatorial map for any cell type. The present invention allows the study of the dynamic changes in the combinatorial pattern of histone PTMs during embryonic stem cell differentiation. Moreover, the present invention allows the exploration of the alterations in histone modifications in transformed cells and human cancers, and how these alterations contribute to tumorigenesis. The present invention may also be used to image combinatorial transcription factor and chromatin regulator interactions and link this information to a genomic locus.

Methods

Cell Culture.

Mouse embryonic stem cells (ESCs) from a male mouse embryo (v6.5, NBP1-41162, Novus, USA) were cultured on mitotically inactivated mouse embryonic fibroblasts (MEFs, Globalstem, USA). ESCs were maintained in medium containing Knockout DMEM (Gibco, USA), 15% Fetal Bovine serum, 1% Pen/Strep (Gibco, USA), 1% Non-essential amino acids (Gibco, USA), 1% Glutamax (Gibco, USA), 0.01% LIF (ESG1107, Millipore, USA) and 0.0004% beta-mercaptoethanol. Mouse lung fibroblasts were purchased from ATCC (CCL-206) and grown in Eagle's Minimum Essential Medium (ATCC, 30-2003) with 10% Fetal Bovine serum. Human HEK-293 cells were grown in medium containing Knockout DMEM (Gibco, USA), 10% Fetal Bovine serum and 1% Pen/Strep (Gibco, USA). Karpas422 B-cell non-Hodgkin's lymphoma cells and SKM-1 acute myeloid leukemia cells were obtained from the Broad-Novartis Cancer Cell Line Encyclopedia (acquired between 2012 and 2014), and were grown in RPMI 1640 (Gibco, USA), 20% Fetal Bovine serum, 1% Glutamax (Gibco, USA), 1% Pen/Strep (Gibco, USA) and 0.0004% beta-mercaptoethanol. The identity of cell lines was validated by Sanger sequencing of unique polymorphisms at the time of acquisition and frozen stock generation in our laboratory. Glioblastoma GBM8 cells (88) were grown in Neurobasal media (Gibco, USA), 0.5% N2 supplement (ThermoFisher Scientific, 17502), 1% B-27 supplement (ThermoFisher Scientific, 17504), 1% Pen/Strep (Gibco, USA), 1.5% Glutamax (Gibco, USA), 0.00002% FGF (Fisher Scientific, 4114TC01M) and 0.00002% EGF (Fisher Scientific, 236EG01M)

Embryoid Bodies (EB) Formation.

For EB formation, ESCs were detached using EDTA dissociation buffer (0.5 mM EDTA and 0.18% NaCl (w/v) in PBS) and further dissociated to single cells using Accumax solution (Sigma, A7089). 4.7 million ESCs were loaded on Aggrewell (STEMCELL technology, 27940) to make 4,700 EBs (1 EB=1,000 ES cell) in EB growth media (ESCs media without LIF). After 3 days, aggregated EBs were collected through a 37 μm strainer (to remove cells that failed to aggregate) and plated on non-coated petri dishes. EBs were grown for an additional 7 days, while changing media every 48 hours.

HDAC, p300 and EZH2 Inhibitors.

For HDAC inhibition, 6 million ES cells were plated on a 150 cm plate. 0.5M stock solution of Sodium butyrate (Sigma, 303410) was prepared fresh for each experiment, and diluted in cell media to a final concentration of 1 mM. Following 6 hours of treatment (unless otherwise noted in text), cells were collected and washed with PBS. For p300 inhibition, 4 million ES cells were plated on a 150 cm plate. 25 mM stock solution of C646 (Sigma, SML0002) was prepared and diluted in cell media to a final concentration of 35 μM. Cells were treated for 24 hours, then collected and washed with PBS. For EZH2 inhibition, 2.5 million Karpas422 B-cell non-Hodgkin's lymphoma cells were suspended in 10 ml media. A 10 mM stock solution of the EZH2 inhibitor GSK126 (32) was prepared and diluted 1:1000 in cell media. Cells were harvested 3 days following treatment.

Nucleosome Preparation for Single-Molecule Imaging.

10 million cells were collected and washed twice with PBS, then resuspended in 500 μl of Lysis buffer (50 mM Tris-HCl pH 7.5, 150 mM NaCl, 1% Triton® X-100, 0.1% sodium deoxycholate, 5 mM CaCl2), supplemented with protease inhibitors (ThermoFisher Scientific, 78425), phosphatase inhibitors (ThermoFisher Scientific, 78420) and HDAC inhibitors (Sodium butyrate, Sigma 303410). Micrococcal Nuclease (ThermoFisher Scientific, 88216) was added to lysis buffer at a concentration of 1 unit per milliliter. The suspension is incubated at 4° C. for 1 hour to lyse the cells, after which MNase is activated by incubating at 37° C. for 20 min and inactivated by addition of EGTA at a final concentration of 20 mM. Next, Applicants centrifuged the lysate for 10 min at max speed and supernatant was transferred to a new tube. 10% of the lysate was used to extract DNA (QIAGEN PCR purification kit, 28104) and run on 2% agarose gel to verify MNase digestion. 100 μl of the lysate were used for ligation of fluorescent, biotinylated adaptors: sample was diluted 1:1 in ligation reaction mixture containing End-It™ DNA End-Repair Kit (Epicentre, ER0720) and Fast-Link™ DNA Ligation Kit (Epicentre, LK0750H). Ligation buffer (100 μl) contained 20 μl ligase buffer, 5 μl of 10 mM dNTPs, 16 μl of 10 Mm ATP, 8 μl End-It, 8 μl fast-link ligase, 1 μl protease inhibitors, 1 μl phosphatase inhibitors, 2 μl of 50 mM sodium butyrate solution, 8 μl annealed adaptors (see sequences below) and H2O. Following at least two hours of ligation at room temperature, 1.5 ml of PBS (supplemented with inhibitors) was added to the sample. Next, the sample was concentrated on an Amicon ultra-4 centrifugal filter unit with ultracel-100 membrane (Millipore, UFC810024) for 15 minutes, and the Pac1 enzymatic reaction (NEB, R0547S) was performed in order to digest adaptor concatemers (adaptors were designed to form Pac1 restriction site in cases of self-ligation). Following Pac1 digestion, nucleosomes were separated on 10-30% glycerol gradients for 18 hours at 35,000 rpm. Fractions were collected and analyzed on 6% DNA retardation gels (ThermoFisher Scientific, EC6365BOX). Gels were imaged with Typhoon trio+imager (Amersham Biosciences), and fractions containing mono-nucleosomes were combined and concentrated on an Amicon Ultra-0.5 Centrifugal Filter Unit with Ultracel-100 membrane (Millipore, UFC510096). For preparation of biotinylated histones (FIG. 2E), histones were purified from ESCs using acid extraction and TCA precipitation as described previously (89). Histones biotinylation was carried out with EZ-Link Sulfo-NHS-Biotinylation Kit (Thermo Scientific, 21425) according to manufacturer's protocol.

Fluorescent, Biotinylated Adaptors.

The following oligonucleotides from Operon were used for ligation to nucleosomes (experiments in FIG. 1-3):

```
(1) [AminoC6 + Alexa647]
        (SEQ. ID Nos 1 and 11, respectively)
[ThiSS]AGATCGGAAGA[BioTEGi]GCGTCGTGTTAA
(red)

(2) [AminoC6 + Alexa555]
        (SEQ. ID Nos 2 and 12, respectively)
[ThiSS]AGATCGGAAGA[BioTEGi]GCGTCGTGTTAA
(green)

(3) Complementary sequence:
                           (SEQ. ID No. 3)
[Phos]TTAACACGACGCTCTTCCGATCT[Sp-3-Q].
```

The following oligonucleotides from IDT were used for ligation to nucleosomes in sequencing experiment (FIG. 4):

```
(1)
                           (SEQ. ID No. 4)
/5Phos/TTAACCGATCACTTCTACGATACCAAAGTATCT/3Bio/

(2) /5Alex647N//iThioMC6D/
                           (SEQ. ID No. 5)
AGArUACrUTrUGGrUATCGrUAGAAGrUGArUCGGTTAA.

(3) The primer sequence:
                           (SEQ. ID No. 6)
AGATACTTTGGTATCGTAGAAGTGATCGGTTA
```

The following oligonucleotide was used for sequencing validation experiment (FIG. 14A):

(SEQ. ID No. 7)
CTTGAGGCCGGTAATACGACTCACTATAGGGGTTCAGAGTTCTACAGTGG
AAAAAAAAAAAAAAAAAAAAAAAAAAAAAAAAAAAAAAAAAAA[Biotin-Q]

Primer used in control sequencing: poly T followed by C, to match the first G after the poly A on the oligonucleotide sequence.

Antibodies.

The following antibodies were purchased from Cell Signaling: (1) Tri-Methyl-Histone H3 (Lys4) (C42D8) Rabbit mAb (Alexa Fluor® 555 Conjugate) #11960. (2) Tri-Methyl-Histone H3 (Lys27) (C36B11) Rabbit mAb (Alexa Fluor® 647 Conjugate) #12158 (3) Acetyl-Histone H3 (Lys9) (C5B11) Rabbit mAb (Alexa Fluor®647 Conjugate) #4484 (4) Di-Methyl-Histone H3 (Lys27) (D18C8) XP® Rabbit mAb (Alexa Fluor® 647 Conjugate) #12244. (5) Acetyl-Histone H3 (Lys27) (D5E4) XP® Rabbit mAb #8173, custom conjugated to Alexa555 by Cell Signaling. (6) Tri-Methyl-Histone H3 (Lys4) (C42D8) Rabbit mAb (Alexa Fluor® 647 Conjugate) #12064. (7) Phospho-Histone H2A.X (Ser139) (20E3) Rabbit mAb (Alexa Fluor® 647 Conjugate) #9720. From Millipore: Anti-trimethyl Histone H3 (Lys27), Alexa Fluor® 555 Conjugate Antibody (07-449-AF555). From Abcam: Anti-Histone H3 (tri methyl K4) antibody [mAbcam1012] (Alexa Fluor® 647) (ab196703).

Antibodies Specificity Dot-Blot Assay.

To test for antibody specificity, Applicants used a peptide array with unlabeled antibodies (the same lots of antibodies that were labeled by Cell Signaling and used for the imaging) according to the following protocol: array is immersed in 4 ml blocking solution (TBST containing 5% non-fat dried milk) for 4 hours at room temperature. Next, array is washed 3 times with TBST, and primary antibody is added (diluted in TBST 1:25,000). Antibody is incubated over night at 4° C. on a rotor. Then the array is washed 3 times in TBST and the secondary antibody (Active Motif, 100612) is added for 1 hour at room temperature. Array is washed again 3 times in TBST and the signal is detected by FlourChemQ.

Imaging.

PEG-biotin microscope slides were purchased from Microsurfaces (www.proteinslides.com/biotin) and assembled into a flow cell. Streptavidin (Sigma, 85878) was added at a concentration of 0.2 mg/ml, and incubated for 10 minutes. Surface was washed with imaging buffer adapted from Deindl et al. (12) containing 10 mM MES pH 6.5 (BIOTANG INC BTBB122), 60 mM KCL, 0.32 mM EDTA, 3 mM MgCl2, 10% glycerol, 0.1 mg/ml acetylated BSA (Promega, R3961), 0.02% Igepal (Sigma, 18896). Biotinylated and dye-labeled mononucleosomes were anchored to the surface via the biotin-streptavidin interactions.

All experiments were performed on a total internal reflection (TIRF) microscope with two lasers, 532 nm/75 mW and 640 nm/40 mW, for fluorescence excitation (Compass 215M, Cube-40C, Coherent). Both laser beams are filtered through band pass filters (Chroma) and spectrally separated by a dichroic mirror (T:640 nm, R:532 nm). They then pass through the TIRF lens and total internal reflection is achieved through a 60×TIRF oil objective with index of refraction 1.49 (Nikon), and imaged onto a CCD camera. After imaging of nucleosomes, the fluorophore is cleaved via addition of TCEP (Bond-Breaker™ TCEP Solution, ThermoFisher Scientific, 77720) diluted 1:10 in imaging buffer. All positions are imaged again in order to discard residual spots from further analysis (less than 2% of spots remain). Next, antibodies are diluted in imaging buffer to a final concentration of 100 ng/ml, and images are taken every 15 minutes for a total incubation time of 3 hours.

All experiments presented herein were performed in at least three biological replicates, including: (1) Ligation of adaptors containing either a red (Alexa647) or a green (Alexa555) fluorophore—since this fluorophore is cleaved, it does not affect the results. (2) Time-lapse imaging of different antibodies sequentially or simultaneously (green-labeled and red-labeled antibodies can be imaged simultaneously with the two lasers, or one antibody can be imaged for 3 hours, washed, and then the second antibody is imaged). (3) For imaging of four marks—altering the order of imaging of the different antibodies. Under all these conditions, experiments are highly reproducible.

Image Analysis.

All image analysis was performed with CellProfiler cell image analysis software, free open-source software (www-.cellprofiler.org/). The pipeline for image analysis is available upon request. Briefly, image analysis is done in three steps: (1) Time-lapse images of antibody binding events are aligned and stacked, and all binding events are summed (spots are also assigned a number that corresponds to the number of binding events per nucleosome). (2) Stacked images are aligned to the initial images of the nucleosomes and to the cleave images. Only binding events that align with nucleosomes that were not present in the cleave image are filtered and saved for further analysis. (3) Filtered modified nucleosomes for each single mark are aligned to identify combinatorial marks on single nucleosomes. If four antibodies are imaged, additional images are taken after washing of the first two antibodies, so that residual binding events can be filtered out. Since the microscope stage is highly accurate, alignment of images results in shifts of less than 5 pixels. Nucleosomes are initially distributed on the surface in low density to minimize overlap between spots.

Single-Molecule Sequencing.

Following imaging of histone marks as described above, the flow cell is washed with 2M NaCl for 10 minutes, and temperature is increased to 37° C. Next, restriction with USER is performed on the surface according to the manufacturer's protocol (NEB, M5505), and incubated for 1 hour at 37° C. Following USER excision, flow cell is washed several times with $H_2O$ pre-heated to 55° C., and primer is added at a final concentration of 10 nM. The primer is allowed to hybridize for 20 minutes, followed by washing. Single-molecule DNA sequencing is carried out by applying Helicos True Single Molecule Sequencing (seqll.com/) as described previously (44).

Calculation of Genomic Coverage by ChIP-Seq.

(FIG. 11) ChIP-Seq on mouse ESCs was performed at the Broad Institute as described previously (90). Sequencing reads were aligned to the genome and peaks were called using HOMER. The fraction of the genome covered was calculated as the total area of enriched regions divided by the mouse genome size.

Preparation of Labeled Mononucleosomes for Imaging.

Harvest Cells and MNase Treatment:
1. Harvest 15 cm plate in PBS, freeze pellet or continue with protocol
2. Wash pellet with PBS+inhibitors
3. Resuspend pellet in 0.5-1 ml of Lysis Buffer X1 diluted in PBS. Add inhibitors.
   Add to lysis buffer MNase in a dilution of 1:2000.

4. Incubate 60 min with rocking in cold room
5. Incubate 20 min in 37° C. to allow MNase digestion
6. Stop reaction by adding EGTA to a final concentration of 20 mM (1:25 from stock of 0.5M, 36 μl for 1 ml reaction).
7. Centrifuge for 10 min at max speed, take supernatant (contains nucleosomes) to a new tube.
8. Remove ~50 μl to a new tube, purify DNA with PCR purification kit, run on Agarose/TBE gel to verify mononucleosomes Ligation of Biotin-Pac1 Oligos:
9. Take 100 μl of the clean sample above for ligation
10. Add 100 μl of 2× ligation buffer (to dilute sample 1:1), including annealed oligos at a concentration of 10 μM (SEQ ID NO 4 and SEQ ID NO 5), and including inhibitors
11. Incubate 2 hours in RT.

Restriction with Pac1:
12. Add to ligation reaction 1.5 ml of PBS+inhibitors, concentrate on column by centrifuging for 14 minutes, 4000 rcf
13. Pac1 reaction (100 μl final volume):
    10 μl NEB buffer 1
    4 μl Pac1
    2 μl Sodium Butyrate
    1 μl protease inhibitors
    1 μl phosphatase inhibitors
    Up to 82 μl of concentrated sample
    Add PBS of necessary
14. Incubate at 37° C. for 1 hour (or more).
15. Add to sample 100 μl of PBS+inhibitors. Take out 5-10 μl (PreG sample)

Glycerol Gradient:
16. When making the glycerol gradients, do the washes with regular glycerol buffers. Make also 50 ml tubes which contain glycerol solutions with the inhibitors in order to make the gradients.
17. Run the sample on a glycerol gradient (which contains inhibitors!) for 18 hours.
18. Collect fractions from gradient in a 96 well plate—8 drops per well
19. Analyze fractions on a 6% DNA retardation gel, collect relevant fractions of mononucleosomes
20. Concentrate mononucleosomes sample on a column, add to final volume the inhibitors.

2× Lysis Buffer (Total 100 ml)

| | |
|---|---|
| 100 mM Tris-HCl (1M, pH 7.5) | 10 ml |
| 300 mM NaCl(5M) | 6 ml |
| 2% Triton ® X-100 (10%) | 20 ml |
| 0.2% sodium deoxycholate(5%) | 4 ml |
| 10 mM CaCl2(1M) | 1 ml |
| H2O | 59 ml |

For each 3 ml of Lysis buffer add 1 μl of MNase (Thermo Scientific), PI (1:25), phosphatase inhibitors (1:25) and sodium butyrate (1:50 from 0.5M solution)
2× Ligation Buffer/Enzymatic Reaction (Total 100 μl)
Kits Used: End-it and Fast-Link DNA Ligation Kits from Epicentre
  20 μl ligase buffer
  5 μl dNTPs (10 mM)
  16 μl (10 Mm) ATP
  8 μl End-It (*2)
  8 μl ligase (*2)
  8 μl annealed Oligos (Final concentration of 10 μM)
  31 μl DDW
  1 μl Protease inhibitors (1:100)
  1 μl Phosphatase inhibitors (1:100)
  2 μl Sodium Butyrate (1:50)
Imaging Buffer

| | Stock | 10 ml | 50 ml |
|---|---|---|---|
| 10 mM MES, pH 6.5 | 0.5M | 200 μl | 1 ml |
| 60 mM KCL | 2M | 300 μl | 1.5 ml |
| 0.32 mM EDTA | 0.5M | 6.4 μl | 32 μl |
| 3 mM MgCl2 | 1M | 30 μl | 150 μl |
| 10% glycerol | 100% | 1 ml | 5 ml |
| 0.1 mg/ml BSA | 10 mg/ml | 100 μl | 500 μl |
| 0.02% Igepal | Make 10% | 20 μl | 100 μl |
| DDW | | 8.4 ml | 42 ml |

REFERENCES

1. D. G. Johnson, S. Y. Dent, Chromatin: receiver and quarterback for cellular signals. *Cell* 152, 685 (Feb. 14, 2013).
2. A. J. Bannister, T. Kouzarides, Regulation of chromatin by histone modifications. *Cell Res* 21, 381 (March, 2011).
3. E. I. Campos, D. Reinberg, Histones: annotating chromatin. *Annual review of genetics* 43, 559 (2009).
4. T. Jenuwein, C. D. Allis, Translating the histone code. *Science* 293, 1074 (Aug. 10, 2001).
5. J. S. Lee, E. Smith, A. Shilatifard, The language of histone crosstalk. *Cell* 142, 682 (Sep. 3, 2010).
6. H. R. Jung, D. Pasini, K. Helin, O. N. Jensen, Quantitative mass spectrometry of histones H3.2 and H3.3 in Suz12-deficient mouse embryonic stem cells reveals distinct, dynamic post-translational modifications at Lys-27 and Lys-36. *Mol Cell Proteomics* 9, 838 (May, 2010).
7. K. J. Ferrari et al., Polycomb-dependent H3K27me1 and H3K27me2 regulate active transcription and enhancer fidelity. *Mol Cell* 53, 49 (Jan. 9, 2014).
8. S. Sidoli, B. A. Garcia, Properly reading the histone code by MS-based proteomics. *Proteomics* 15, 2901 (September, 2015).
9. D. Gomez, L. S. Shankman, A. T. Nguyen, G. K. Owens, Detection of histone modifications at specific gene loci in single cells in histological sections. *Nat Methods* 10, 171 (February, 2013).
10. P. J. Murphy et al., Single-molecule analysis of combinatorial epigenomic states in normal and tumor cells. *Proc Natl Acad Sci USA* 110, 7772 (May 7, 2013).
11. W. J. Koopmans, T. Schmidt, J. van Noort, Nucleosome immobilization strategies for single-pair FRET microscopy. *Chemphyschem: a European journal of chemical physics and physical chemistry* 9, 2002 (Oct. 6, 2008).
12. S. Deindl et al., ISWI remodelers slide nucleosomes with coordinated multi-base-pair entry steps and single-base-pair exit steps. *Cell* 152, 442 (Jan. 31, 2013).
13. B. E. Bernstein et al., A bivalent chromatin structure marks key developmental genes in embryonic stem cells. *Cell* 125, 315 (Apr. 21, 2006).
14. V. Azuara et al., Chromatin signatures of pluripotent cell lines. *Nat Cell Biol* 8, 532 (May, 2006).
15. P. Voigt, W. W. Tee, D. Reinberg, A double take on bivalent promoters. *Genes Dev* 27, 1318 (Jun. 15, 2013).
16. S. Denissov et al., M112 is required for H3K4 trimethylation on bivalent promoters in embryonic stem cells, whereas M111 is redundant. *Development* 141, 526 (February, 2014).

17. D. Hu et al., The M112 branch of the COMPASS family regulates bivalent promoters in mouse embryonic stem cells. *Nat Struct Mol Biol* 20, 1093 (September, 2013).
18. P. Voigt et al., Asymmetrically modified nucleosomes. *Cell* 151, 181 (Sep. 28, 2012).
19. T. Y. Roh, S. Cuddapah, K. Cui, K. Zhao, The genomic landscape of histone modifications in human T cells. *Proc Natl Acad Sci USA* 103, 15782 (Oct. 24, 2006).
20. G. Pan et al., Whole-genome analysis of histone H3 lysine 4 and lysine 27 methylation in human embryonic stem cells. *Cell Stem Cell* 1, 299 (Sep. 13, 2007).
21. M. De Gobbi et al., Generation of bivalent chromatin domains during cell fate decisions. *Epigenetics Chromatin* 4, 9 (2011).
22. O. Alder et al., Ring1B and Suv39h1 delineate distinct chromatin states at bivalent genes during early mouse lineage commitment. *Development* 137, 2483 (Aug. 1, 2010).
23. J. Zhu et al., Genome-wide chromatin state transitions associated with developmental and environmental cues. *Cell* 152, 642 (Jan. 31, 2013).
24. R. D. Hawkins et al., Distinct epigenomic landscapes of pluripotent and lineage-committed human cells. *Cell Stem Cell* 6, 479 (May 7, 2010).
25. F. W. Schmitges et al., Histone methylation by PRC2 is inhibited by active chromatin marks. *Mol Cell* 42, 330 (May 6, 2011).
26. S. B. Baylin, P. A. Jones, A decade of exploring the cancer epigenome—biological and translational implications. *Nat Rev Cancer* 11, 726 (October, 2011).
27. A. A. Mills, Throwing the cancer switch: reciprocal roles of polycomb and trithorax proteins. *Nat Rev Cancer* 10, 669 (October, 2010).
28. S. J. Geisler, R. Paro, Trithorax and Polycomb group-dependent regulation: a tale of opposing activities. *Development* 142, 2876 (Sep. 1, 2015).
29. T. Ernst et al., Inactivating mutations of the histone methyltransferase gene EZH2 in myeloid disorders. *Nat Genet* 42, 722 (August, 2010).
30. D. B. Yap et al., Somatic mutations at EZH2 Y641 act dominantly through a mechanism of selectively altered PRC2 catalytic activity, to increase H3K27 trimethylation. *Blood* 117, 2451 (Feb. 24, 2011).
31. W. Beguelin et al., EZH2 is required for germinal center formation and somatic EZH2 mutations promote lymphoid transformation. *Cancer Cell* 23, 677 (May 13, 2013).
32. M. T. McCabe et al., EZH2 inhibition as a therapeutic strategy for lymphoma with EZH2-activating mutations. *Nature* 492, 108 (Dec. 6, 2012).
33. M. P. Creyghton et al., Histone H3K27ac separates active from poised enhancers and predicts developmental state. *Proc Natl Acad Sci USA* 107, 21931 (Dec. 14, 2010).
34. J. Ernst et al., Mapping and analysis of chromatin state dynamics in nine human cell types. *Nature* 473, 43 (May 5, 2010).
35. A. Rada-Iglesias et al., A unique chromatin signature uncovers early developmental enhancers in humans. *Nature* 470, 279 (Feb. 10, 2011).
36. E. Calo, J. Wysocka, Modification of enhancer chromatin: what, how, and why? *Mol Cell* 49, 825 (Mar. 7, 2013).
37. E. Meshorer, T. Misteli, Chromatin in pluripotent embryonic stem cells and differentiation. *Nat Rev Mol Cell Biol* 7, 540 (July, 2006).
38. O. Ram et al., Combinatorial Patterning of Chromatin Regulators Uncovered by Genome-wide Location Analysis in Human Cells. *Cell* 147, 1628 (Dec. 23, 2011).
39. N. T. Crump et al., Dynamic acetylation of all lysine-4 trimethylated histone H3 is evolutionarily conserved and mediated by p300/CBP. *Proc Natl Acad Sci USA* 108, 7814 (May 10, 2011).
40. T. Robert et al., HDACs link the DNA damage response, processing of double-strand breaks and autophagy. *Nature* 471, 74 (Mar. 3, 2011).
41. G. J. Narlikar, H. Y. Fan, R. E. Kingston, Cooperation between complexes that regulate chromatin structure and transcription. *Cell* 108, 475 (Feb. 22, 2002).
42. V. Turinetto, C. Giachino, Multiple facets of histone variant H2AX: a DNA double-strand-break marker with several biological functions. *Nucleic Acids Res* 43, 2489 (Mar. 11, 2015).
43. J. P. Banath et al., Explanation for excessive DNA single-strand breaks and endogenous repair foci in pluripotent mouse embryonic stem cells. *Exp Cell Res* 315, 1505 (May 1, 2009).
44. T. D. Harris et al., Single-molecule DNA sequencing of a viral genome. *Science* 320, 106 (Apr. 4, 2008).
45. Kouzarides, T. Chromatin modifications and their function. *Cell* 128, 693-705, doi:10.1016/j.cell.2007.02.005 (2007).
46. Zhou, V. W., Goren, A. & Bernstein, B. E. Charting histone modifications and the functional organization of mammalian genomes. *Nature reviews. Genetics* 12, 7-18, doi:10.1038/nrg2905 (2011).
47. Rivera, C. M. & Ren, B. Mapping human epigenomes. *Cell* 155, 39-55, doi:10.1016/j.cell.2013.09.011 (2013).
48. Schones, D. E. & Zhao, K. Genome-wide approaches to studying chromatin modifications. *Nature reviews. Genetics* 9, 179-191, doi:10.1038/nrg2270 (2008).
49. Mikkelsen, T. S. et al. Genome-wide maps of chromatin state in pluripotent and lineage-committed cells. *Nature* 448, 553-560, doi:10.1038/nature06008 (2007).
50. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nature methods* 10, 1213-1218, doi:10.1038/nmeth.2688 (2013).
51. Thurman, R. E. et al. The accessible chromatin landscape of the human genome. *Nature* 489, 75-82, doi:10.1038/nature11232 (2012).
52. Collas, P. The current state of chromatin immunoprecipitation. *Molecular biotechnology* 45, 87-100, doi:10.1007/s12033-009-9239-8 (2010).
53. Kuo, M. H. & Allis, C. D. In vivo cross-linking and immunoprecipitation for studying dynamic Protein:DNA associations in a chromatin environment. *Methods* 19, 425-433, doi:10.1006/meth.1999.0879 (1999).
54. Solomon, M. J., Larsen, P. L. & Varshavsky, A. Mapping protein-DNA interactions in vivo with formaldehyde: evidence that histone H4 is retained on a highly transcribed gene. *Cell* 53, 937-947 (1988).
55. Gilmour, D. S. & Lis, J. T. Detecting protein-DNA interactions in vivo: distribution of RNA polymerase on specific bacterial genes. *Proceedings of the National Academy of Sciences of the United States of America* 81, 4275-4279 (1984).
56. Strahl, B. D. & Allis, C. D. The language of covalent histone modifications. *Nature* 403, 41-45, doi:10.1038/47412 (2000).

57. Lara-Astiaso, D. et al. Immunogenetics. Chromatin state dynamics during blood formation. *Science* 345, 943-949, doi:10.1126/science.1256271 (2014).
58. Chabbert, C. D. et al. A high-throughput ChIP-Seq for large-scale chromatin studies. *Molecular systems biology* 11, 777, doi:10.15252/msb.20145776 (2015).
59. van Galen, P. et al. A Multiplexed System for Quantitative Comparisons of Chromatin Landscapes. *Molecular cell* 61, 170-180, doi:10.1016/j.molcel.2015.11.003 (2016).
60. Rotem, A. et al. Single-cell ChIP-seq reveals cell subpopulations defined by chromatin state. *Nature biotechnology* 33, 1165-1172, doi:10.1038/nbt.3383 (2015).
61. Liu, Z., Lavis, L. D. & Betzig, E. Imaging live-cell dynamics and structure at the single-molecule level. *Molecular cell* 58, 644-659, doi:10.1016/j.molcel.2015.02.033 (2015).
62. Reck-Peterson, S. L., Derr, N. D. & Stuurman, N. Imaging single molecules using total internal reflection fluorescence microscopy (TIRFM). *Cold Spring Harbor protocols* 2010, pdb top73, doi:10.1101/pdb.top73 (2010).
63. Tessler, L. A., Reifenberger, J. G. & Mitra, R. D. Protein quantification in complex mixtures by solid phase single-molecule counting. *Analytical chemistry* 81, 7141-7148, doi:10.1021/ac901068x (2009).
64. Ozsolak, F. et al. Direct RNA sequencing. *Nature* 461, 814-818, doi:10.1038/nature08390 (2009).
65. Eid, J. et al. Real-time DNA sequencing from single polymerase molecules. *Science* 323, 133-138, doi: 10.1126/science.1162986 (2009).
66. Rando, O. J. Combinatorial complexity in chromatin structure and function: revisiting the histone code. *Current opinion in genetics & development* 22, 148-155, doi:10.1016/j.gde.2012.02.013 (2012).
67. Schreiber, S. L. & Bernstein, B. E. Signaling network model of chromatin. *Cell* 111, 771-778 (2002).
68. Adli, M., Zhu, J. & Bernstein, B. E. Genome-wide chromatin maps derived from limited numbers of hematopoietic progenitors. *Nature methods* 7, 615-618, doi: 10.1038/nmeth.1478 (2010).
69. Goren, A. et al. Chromatin profiling by directly sequencing small quantities of immunoprecipitated DNA. *Nature methods* 7, 47-49, doi:10.1038/nmeth.1404 (2010).
70. Lipson, D. et al. Quantification of the yeast transcriptome by single-molecule sequencing. *Nature biotechnology* 27, 652-658, doi:10.1038/nbt.1551 (2009).
71. Kapranov, P. et al. New class of gene-termini-associated human RNAs suggests a novel RNA copying mechanism. *Nature* 466, 642-646, doi:10.1038/nature09190 (2010).
72. Meshorer, E. et al. Hyperdynamic plasticity of chromatin proteins in pluripotent embryonic stem cells. *Developmental cell* 10, 105-116, doi:10.1016/j.devcel.2005.10.017 (2006).
73. Egelhofer, T. A. et al. An assessment of histone-modification antibody quality. *Nature structural & molecular biology* 18, 91-93, doi:10.1038/nsmb.1972 (2011).
74. Schubeler, D. Function and information content of DNA methylation. *Nature* 517, 321-326, doi:10.1038/nature14192 (2015).
75. Kohli, R. M. & Zhang, Y. TET enzymes, TDG and the dynamics of DNA demethylation. *Nature* 502, 472-479, doi:10.1038/nature12750 (2013).
76. Koziol, M. J. et al. Identification of methylated deoxyadenosines in vertebrates reveals diversity in DNA modifications. *Nature structural & molecular biology*, doi: 10.1038/nsmb.3145 (2015).
77. Ulahannan, N. & Greally, J. M. Genome-wide assays that identify and quantify modified cytosines in human disease studies. *Epigenetics & chromatin* 8, 5, doi: 10.1186/1756-8935-8-5 (2015).
78. Brind'Amour, J. et al. An ultra-low-input native ChIP-seq protocol for genome-wide profiling of rare cell populations. *Nature communications* 6, 6033, doi:10.1038/ncomms7033 (2015).
79. O'Neill, L. P., VerMilyea, M. D. & Turner, B. M. Epigenetic characterization of the early embryo with a chromatin immunoprecipitation protocol applicable to small cell populations. *Nature genetics* 38, 835-841, doi: 10.1038/ng1820 (2006).
80. Zheng, X. et al. Low-Cell-Number Epigenome Profiling Aids the Study of Lens Aging and Hematopoiesis. *Cell reports* 13, 1505-1518, doi:10.1016/j.celrep.2015.10.004 (2015).
81. Buenrostro, J. D. et al. Single-cell chromatin accessibility reveals principles of regulatory variation. *Nature* 523, 486-490, doi:10.1038/nature14590 (2015).
82. Schmidl, C., Rendeiro, A. F., Sheffield, N. C. & Bock, C. ChIPmentation: fast, robust, low-input ChIPseq for histones and transcription factors. *Nature methods* 12, 963-965, doi:10.1038/nmeth.3542 (2015).
83. West, J. A. et al. Nucleosomal occupancy changes locally over key regulatory regions during cell differentiation and reprogramming. *Nature communications* 5, 4719, doi: 10.1038/ncomms5719 (2014).
84. Hsu, P. D., Lander, E. S. & Zhang, F. Development and applications of CRISPR-Cas9 for genome engineering. *Cell* 157, 1262-1278, doi:10.1016/j.cell.2014.05.010 (2014).
85. Knight, S. C. et al. Dynamics of CRISPR-Cas9 genome interrogation in living cells. *Science* 350, 823-826, doi: 10.1126/science.aac6572 (2015).
86. McCaffrey, J. et al. CRISPR-CAS9 D10A nickase target-specific fluorescent labeling of double strand DNA for whole genome mapping and structural variation analysis. *Nucleic Acids Res*, doi:10.1093/nar/gkv878 (2015).
87. Deng, W., Shi, X., Tjian, R., Lionnet, T. & Singer, R. H. CASFISH: CRISPR/Cas9-mediated in situ labeling of genomic loci in fixed cells. *Proc Natl Acad Sci USA* 112, 11870-11875, doi:10.1073/pnas.1515692112 (2015).
88. H. Wakimoto et al., Maintenance of primary tumor phenotype and genotype in glioblastoma stem cells. *Neuro-oncology* 14, 132 (February, 2012).
89. D. Shechter, H. L. Dormann, C. D. Allis, S. B. Hake, Extraction, purification and analysis of histones. *Nat Protoc* 2, 1445 (2007).
90. E. Rheinbay et al., An aberrant transcription factor network essential for Wnt signaling and stem cell maintenance in glioblastoma. *Cell reports* 3, 1567 (May 30, 2013).
91. K. Bouazoune, R. E. Kingston, Chromatin remodeling by the CHD7 protein is impaired by mutations that cause human developmental disorders. *P Natl Acad Sci USA* 109, 19238 (Nov. 20, 2012).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

SEQ ID NOS 1 and 11, respectively:
[AminoC6 + Alexa647]
[ThiSS]AGATCGGAAGA[BioTEGi]GCGTCGTGTTAA (red)

SEQ ID NOS 2 and 12, respectively:
[AminoC6 + Alexa555]
[ThiSS]AGATCGGAAGA[BioTEGi]GCGTCGTGTTAA (green)

SEQ ID NO 3:
[Phos]TTAACACGACGCTCTTCCGATCT[Sp-3-Q]

SEQ ID NO 4:
/5Phos/TTAACCGATCACTTCTACGATACCAAAGTATCT/3Bio/

SEQ ID NO 5:
/5Alex647N//iThioMC6D/AGArUACrUTrUGGrUATCGrUAGAAGr
UGArUCGGTTAA

SEQ ID NO 6:
AGATACTTTGGTATCGTAGAAGTGATCGGTTA

SEQ ID NO 7:
CTTGAGGCCGGTAATACGACTCACTATAGGGGTTCAGAGTTCTACAGTGG
AAAAAAAAAAAAAAAAAAAAAAAAAAAAAAAAAAAAAAAA[Biotin-Q]

What is claimed is:

1. A method for analyzing chromatin, the method comprising:
   (a) covalently linking an oligonucleotide sequence to a plurality of isolated chromatin fragments, wherein the oligonucleotide sequence is configured to bind to a capture molecule;
   (b) purifying mononucleosomes from the isolated chromatin fragments linked to an oligonucleotide sequence;
   (c) binding the mononucleosomes to a solid support comprising the capture molecule, wherein the positions of the mononucleosomes are fixed and spatially-distributed;
   (d) incubating the solid support with a labeling ligand with specific binding affinity for a target molecule on the mononucleosome; and
   (e) imaging the solid support at at least two time points, whereby an individual mononucleosome comprising the target molecule is visualized, and whereby repeated binding and dissociation events between the labeling ligand and the target molecule on the individual mononucleosome are monitored.

2. The method according to claim 1, wherein the oligonucleotide sequence comprises one strand that comprises at least one uracil base.

3. The method according to claim 1, wherein the isolated chromatin fragments are obtained by a method comprising:
   (a) separating single cells into droplets formed by an aqueous solution in oil emulsion, wherein each droplet comprises a single cell, a nuclease, a ligase and no more than one bead comprising a unique barcode sequence;
   (b) lysing cells within the droplet, whereby the nuclease digests the genomic DNA and the ligase ligates chromatin fragments to the unique barcode sequence;
   (c) breaking the emulsions; and
   (d) removing the barcode sequence from the bead,
whereby isolated chromatin fragments are generated comprising a unique barcode sequence that is configured to be further ligated to the oligonucleotide sequence.

4. The method according to claim 1, wherein the isolated chromatin fragments are obtained by a method comprising:
   (a) separating single cells into droplets formed by an aqueous solution in oil emulsion, wherein each droplet comprises a single cell, a nuclease, and a lysis buffer; and
   (b) lysing cells within the droplets, whereby the nuclease digests the chromatin released from the cells, and wherein the oligonucleotide sequence is introduced into each of said droplet and wherein the oligonucleotide sequence is covalently linked within the droplet.

5. The method according to claim 4, wherein after the step of covalently linking an oligonucleotide sequence to a plurality of isolated chromatin fragments the method further comprises breaking the emulsions.

6. The method according to claim 1, wherein the isolated chromatin fragments are obtained by a method comprising:
(a) separating single cells into individual wells;
(b) lysing cells within each well; and
(c) digesting the lysed cells with a nuclease,
wherein the oligonucleotide sequence is covalently linked within each well.

7. The method according to claim 1, wherein the isolated chromatin fragments are obtained by a method comprising:
(a) lysing at least one cell; and
(b) incubating the lysed cell with a Tn5-transposase loaded with two tagmentation adapters configured for ligation to the oligonucleotide sequence.

8. The method according to claim 1, wherein the target molecule comprises a histone modification, nucleotide modification, histone variant, chromatin remodeling factor, a methyl-transferase, an acetylase, a deacetylase, a kinase, a phosphatase, a ubiquitin ligase or a transcription factor.

9. The method of claim 1, wherein the chromatin fragments are obtained from a biological sample selected from the group consisting of sera, plasma, lymph, blood, blood fractions, urine, synovial fluid, spinal fluid, saliva, circulating tumor cells (CTC) and mucous.

10. The method according to claim 9, wherein the method is used to characterize a disease or risk for a disease associated with modified, cell-free nucleosomes selected from the group consisting of pre-malignant and malignant neoplasms, histiocytoma, glioma, astrocytoma, osteoma, lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma, leukemias, systemic lupus erythematosus, psoriasis, bone diseases, fibroproliferative disorders of connective tissue, cataracts and atherosclerosis.

11. The method according to claim 1, wherein the target molecule is a histone modification.

12. The method according to claim 11, wherein the histone modification is selected from the group consisting of H2B Ser 14 (Phos), H3 Ser 10 (Phos), H3 Lys 9 (Me), H3 Lys 27 (Me), H3 Lys 36 (Me), H3 Lys 79 (Me), H4 Lys 20 (Me), H3 Lys 4 (Me), H3 Lys 9 (Ac), H3 Lys 14 (Ac), H3 Lys 23 (Ac), H4 arg 3 (Me), H3 Lys 27 (Ac), H4 arg 3 (Me), H4 lys 5 (Ac), H4 Ser 2 (phos), H4 Arg 3(me), H4 Lys 5 (Ac) and H3 Lys 18 (Ac); the nucleotide modification is selected from the group consisting of 5-methyl- (5-mC), 5-hydroxymethyl- (5-hmC), 5-formyl- (5-fC) and 5-carboxy- (5-caC) cytosine; the histone variant is selected from the group consisting of macroH2A1.1, macroH2A1.2, H2AZ, H2AX, H3.1 and H3.3.

13. The method according to claim 12, wherein a bivalent histone modifications is detected on the individual mononucleosome.

14. The method according to claim 13, wherein the bivalent histone modification comprises H3K27me3 and H3K4me3.

15. The method according to claim 1, further comprising sequencing of the DNA associated with the individual mononucleosome following step (e), wherein the mononucleosome remains bound to the solid support during sequencing, and whereby nucleosome composition, modification and/or nucleotide sequence is determined for single nucleosomes obtained from cell-free chromatin fragments.

16. The method according to claim 15, wherein the sequencing comprises sequencing of bisulfite converted DNA.

17. The method according to claim 16, wherein active and inactive genes are determined by a method comprising analyzing gene sequences bound to nucleosomes comprising histone modifications indicative of active chromatin or inactive chromatin.

18. The method of claim 1 further comprising integrating images from step (e).

19. The method of claim 1, wherein binding and dissociation events are detected between the individual mononucleosome and each of multiple distinct labeling ligands, regardless of steric hindrance.

20. A method for the unbiased isolation and analysis of chromatin fragments from a biological sample, the method comprising:
(a) covalently linking an oligonucleotide sequence to a plurality of isolated chromatin fragments, wherein the oligonucleotide sequence is configured to bind to a capture molecule;
(b) purifying mononucleosomes from the isolated chromatin fragments linked to an oligonucleotide sequence;
(c) binding the mononucleosomes to a solid support comprising the capture molecule, wherein the positions of the mononucleosomes are fixed and spatially-distributed;
(d) incubating the solid support with a labeling ligand with specific binding affinity for a histone modification on the mononucleosomes; and
(e) imaging the solid support at at least two time points, whereby an individual mononucleosome comprising the histone modification is visualized, and whereby repeated binding and dissociation events between the labeling ligand and the histone modification on the individual mononucleosome are monitored.

21. The method of claim 20, wherein the imaging is single-molecule imaging, and wherein millions of individual mononucleosomes bound to the solid support are imaged.

22. The method of claim 21, wherein binding and dissociation events are detected in step (e) between the individual mononucleosome and each of multiple distinct labeling ligands, each with specific binding affinity for a different histone modification, regardless of steric hindrance.

23. The method of claim 1, wherein the time between each time point in (e) is at least one minute.

24. The method of claim 21, further comprising sequencing of DNA of the individual mononucleosome while the DNA remains bound to the solid support, wherein the sequencing is done following step (e).

* * * * *